United States Patent [19]
Sledziewski et al.

[11] Patent Number: 6,018,026
[45] Date of Patent: *Jan. 25, 2000

[54] BIOLOGICALLY ACTIVE DIMERIZED AND MULTIMERIZED POLYPEPTIDE FUSIONS

[75] Inventors: Andrzej Z. Sledziewski; Lillian Anne Bell; Wayne R. Kindsvogel, all of Seattle, Wash.

[73] Assignee: ZymoGenetics, Inc., Seattle, Wash.

[*] Notice: This patent is subject to a terminal disclaimer.

[21] Appl. No.: 08/980,400

[22] Filed: Nov. 26, 1997

Related U.S. Application Data

[62] Division of application No. 08/477,329, Jun. 7, 1995, Pat. No. 5,750,375, which is a continuation of application No. 08/180,195, Jan. 11, 1994, Pat. No. 5,567,584, which is a continuation of application No. 07/634,510, Dec. 27, 1990, abandoned, which is a continuation-in-part of application No. 07/347,291, May 2, 1989, Pat. No. 5,155,027, which is a continuation-in-part of application No. 07/146,877, Jan. 22, 1988, abandoned.

[51] Int. Cl.[7] .......................... C07K 19/00; C07K 16/46; C07K 14/71
[52] U.S. Cl. ................. 530/350; 530/387.3; 530/388.24; 530/399; 530/402
[58] Field of Search ................................ 530/350, 387.3, 530/388.24, 399, 402; 435/69.7, 172.3

[56] References Cited

U.S. PATENT DOCUMENTS

| | | | |
|---|---|---|---|
| 4,474,893 | 10/1984 | Reading ................................... | 436/547 |
| 4,599,311 | 7/1986 | Kawasaki ................................. | 435/71 |
| 4,761,371 | 8/1988 | Bell et al. ............................... | 435/68 |
| 4,766,073 | 8/1988 | Murray et al. ........................ | 435/172.3 |
| 4,816,397 | 3/1989 | Boss et al. .............................. | 435/68 |
| 4,816,567 | 3/1989 | Cabilly et al. .......................... | 530/387 |
| 5,015,571 | 5/1991 | Niman et al. ........................... | 435/7.92 |
| 5,098,833 | 3/1992 | Lasky et al. ............................ | 435/69.1 |
| 5,116,964 | 5/1992 | Capon et al. ............................ | 536/27 |
| 5,155,027 | 10/1992 | Sledziewski et al. ................. | 435/69.7 |
| 5,750,375 | 5/1998 | Sledziewski et al. ................. | 435/69.7 |

FOREIGN PATENT DOCUMENTS

| | | |
|---|---|---|
| 088 994 | 9/1983 | European Pat. Off. . |
| 116 201 | 8/1984 | European Pat. Off. . |
| 120 694 | 10/1984 | European Pat. Off. . |
| 162 319 | 11/1985 | European Pat. Off. . |
| 171 496 | 2/1986 | European Pat. Off. . |
| 173 494 | 3/1986 | European Pat. Off. . |
| 239 400 | 9/1987 | European Pat. Off. . |
| 244 221A1 | 11/1987 | European Pat. Off. . |
| 256 654 | 2/1988 | European Pat. Off. . |
| 315 062 | 5/1989 | European Pat. Off. . |
| 327 369A2 | 8/1989 | European Pat. Off. . |
| WO 86/01533 | 3/1986 | WIPO . |
| WO 90/06953 | 6/1990 | WIPO . |

OTHER PUBLICATIONS

Kuwana et al., *Biochemical and Biophysical Research Communications 149* (3) : 960–968, 1987.
Yarden et al., *Nature 323*:226–232, 1986.
Hart et al., *Science 240*:1529–1531, 1988.
Escobedo et al., *Science 240*:1532–1534, 1988.
Heldin et al., *Embo J. 7*:1387–1393, 1988.
Radeke et al., *Nature 325*593–597, 1987.
Ebina et al., *Cell 40*:747–758, 1985.
Rubin et al., *J. Immun. 135*:3172–3177, 1985.
Ellis et al., *J. Cell Biol. 150*:14a, 1987.
Smith et al., *Science 238*:1704–1707, 1987.
Livneh et al., *J. Biol. Chem. 261*: 12490–12497, 1986.
Boni–Schnetzler and Pilch, *Proc. Natl. Acad. Sci. USA 84*:7832–7836, 1987.
Claesson–Welsh et al., *Mol. Cell. Biol.* 8:3476–3486, 1988.
Ullrich et al., *Nature 309*:418–425, 1984.
Ullrich et al., *Nature 313*: 756–761, 1985.
Derynck et al., *Nature 316*:701–705, 1985.
Loh et al., *Cell 33*:85–93, 1983.
Honjo et al., *Cell 18*:559–568, 1979.
Alber and Kawasaki, *J. Mol. Appl. Genet. 1*: 419–434, 1982.
Russell et al., *Nature 304*: 652–654, 1983.
Grosschedl and Baltimore, *Cell 41*: 885–897, 1985.
Hieter et al., *Cell 22*: 197–207, 1980.
Treiger et al., *J. Immunol. 136*:4099–4105, 1986.
Roth et al., *J. Cell. Biol. 102*:1271–1283, 1986.
Riedel et al., *Science 236*:197–200, 1987.
Riedel et al., *Nature 324*:68–70, 1986.
Gascoigne et al., *Proc. Natl. Acad. Sci. USA 84*:2936–2940, 1987.
Maddon et al., *Cell 47*: 333–348, 1986.
Maddon et al., *Cell 42*: 93–104, 1985.
Capon et al., *Nature 337*:525–531, 1989.
Wood et al., *Nature 314*:446–449, 1985.
Carlson et al., *Mol. Cell. Biol. 3*:439–447, 1983.
Marx, *Science 229*:455–456, 1985.
Neuberger et al., *Nature 312*: 604–609, 1984.
Oi and Morrison *Biotechniques 4*:214–221, 1986.
Bailon et al., *Bio/Technology 5*:1195–1198, 1987.
Ballou et al., *J. Biol. Chem. 255*:5986–5991, 1980.

(List continued on next page.)

*Primary Examiner*—Lorraine Spector
*Assistant Examiner*—Claire M. Kaufman
*Attorney, Agent, or Firm*—Townsend and Townsend and Crew

[57] ABSTRACT

Methods for producing secreted receptor analogs and biologically active peptide dimers are disclosed. The methods for producing secreted receptor analogs and biologically active peptide dimers utilize a DNA sequence encoding a receptor analog or a peptide requiring dimerization for biological activity joined to a dimerizing protein. The receptor analog includes a ligand-binding domain. Polypeptides comprising essentially the extracellular domain of a human PDGF receptor fused to dimerizing proteins, the portion being capable of binding human PDGF or an isoform thereof, are also disclosed. The polypeptides may be used within methods for determining the presence of and for purifying human PDGF or isoforms thereof.

29 Claims, 21 Drawing Sheets

OTHER PUBLICATIONS

Munro and Pelham, *EMBO J. 3*:3087–3093, 1984.
von Heijne, *Nucl Acids Res. 14*: 4683–4690, 1986.
von Heijne, *Eur. J. Biochem. 133*:17–21, 1983.
Beggs, *Nature*: 104–108, 1978.
Clarke et al., *Meth. Enzym. 68*:436–442, 1979.
Struhl et al., *Proc. Natl. Acad. Sci. USA 76*:1035–1039, 1979.
Broach et al., *Gene 8*:121–133, 1979.
Mariuzza and Winter, *J. Biol. Chem. 264*:7310–7316, 1989.
Gronwald et al., *Proc. Natl. Acad. Sci. USA 85*:3435–3439, 1988.
Riedel et al., *Protein Engineering 1*(3):237, 1987.
Traunecker et al., Highly efficient neutralization of HIV with recombinant CD4–immunoglobulin molecules, Nature, 339: 68–70, May 4, 1989.

```
  1  GGCCCCTCAGCCCTGCTGCCCAGCACGAGAGCCTGTGCTGCGCCCTGCCCAACGCAGACAGCCAGACCCAGG                    69
 70  GCGGCCCCTCTGGCGCGCTCTGCTCCTCCCGAAGGATGCTTGGGGAGTGAGGCGAAGCTGAGGCGCTCCTC                   138
139  TCCCCTACAGCAGCCCCCCTTCCTCCATCCCTCTGTTCTCCCTGAGCCTTCAGGAGCCTGCACCAGTCCTG                   207
208  CCTGTCCTTCTACTCAGCTGTTACCCACTCTGGGACCAGCAGTCTTTCTGATAACTGGGAGAGGGCAGT                     276
277  AAGGAGGACTTCCTGGAGGGGTGACTGTCCAGAGCCTGGAACTGTGCCACCAGAAGCCATCAGCA                         345
346  GCAAGGACACCATGCGCTTCCGGGTGCCGATGCCAGCTCTGGCCCTCAAAGGCGAGCTGCTGTTGCTGT                     414
                    M   R   L   P   G   A   M   P   A   L   A   L   K   G   E   L   L   L   L   S    20
415  CTCTCCTGTTACTTCTGGAACCACAGATCTCTCAGGGCCTGGTCGTCACACCCCCCGGGCCAGAGCTTG                     483
      L   L   L   L   L   L   E   P   Q   I   S   Q   G   L   V   V   T   P   P   G   P   E   L   V    43
484  TCCTCAATGTCTCCAGCACCTTCGTTCTCTGACCTGCTCTCGGGTTCAGCTCCGGTGGTGTGGGAACGGATGT                 552
      L   N   V   S   S   T   F   V   L   T   C   S   G   S   A   P   V   V   W   E   R   M   S       66
553  CCCAGGAGCCCCCACAGGAAATGGCCAAGGCCCAGGATGGCACCTTCTCCAGCGTGCTGCTCACACTGACCA                  621
      Q   E   P   P   Q   E   M   A   K   A   Q   D   G   T   F   S   S   V   L   L   T   L   T   N    89
622  ACCTCACTGGGCTAGACACGGGAGAATACTTTTGCACCCACAATGACTCCCGTGGAGACCGATG                          690
      L   T   G   L   D   T   G   E   Y   F   C   T   H   N   D   S   R   G   L   E   T   D   E       112
691  AGCGGAAACGGCTCTACATCTTTGTGCCAGATCCCGATACCGTGGGCTTCCTCCCTAATGATGCCGAGGAAC                  759
      R   K   R   L   Y   I   F   V   P   D   P   D   T   V   G   F   L   P   N   D   A   E   E   L   135
760  TATTCATCTTTCTCACGGAAATAACTGAGATCACCATTCCATGCCGAGTAACAGACCCCACAGCTGGTGG                    828
      F   I   F   L   T   E   I   T   E   I   T   I   P   C   R   V   T   D   P   Q   L   V   V      158
```

Fig. 1A

```
 829  TGACACTGCACGAGAAGAAAGGGGACGTTGCACTGCCTGTCCCTATGATCACCAACGTGGCTTTTCTG  897
       T  L  H  E  K  K  G  D  V  A  L  P  V  P  Y  D  H  Q  R  G  F  S  G   181

898  GTATCTTTGAGGACAGAAGCTACATCTGCAAAACCACCATTGGGACAGGAGGTGGATTCTGATGCCT  966
       V  S  F  E  D  R  S  Y  I  C  K  T  T  I  G  D  R  E  V  D  S  D  A  Y  204

967  ACTATGTCTACAGACTCCAGGTGTCATCCATCAACGTCTCTGTGAACGCAGTGCAGACTGTGGTCCGCC 1035
       Y  Y  V  Y  R  L  Q  V  S  S  I  N  V  S  V  N  A  V  Q  T  V  V  R  Q  227

1036  AGGGTGAGAACATCACCCTCATGTGCATTGTGATCGGGAATGAGGTGGTCAACTTCGAGTGGACATACC 1104
       G  E  N  I  T  L  M  C  I  V  I  G  N  E  V  V  N  F  E  W  T  Y  P   250

1105  CCCGCAAAGAAAGTGGGCGGCCGGTTAGAAGACTCGGGAGACTACACCTGCAATGTGACGGAGA     1173
       R  K  E  S  G  R  L  V  E  P  V  T  D  F  L  L  D  H  P  Y  M  I  R   273

1174  GCTCCATCCTGCACATCCCCAGTGCCGAGTTAGAAGACTCGGGAGACCTACACCTGCAATGTGACGGAGA 1242
       S  I  L  H  I  P  S  A  E  L  E  D  S  G  T  Y  T  C  N  V  T  E  S   296

1243  GTGTGAATGACCATCAGGATGAAAAGGCCATCAACATCACCGTGGTTGAGAGCGGCTACGTGCGGCTCC 1311
       V  N  D  H  Q  D  E  K  A  I  N  I  T  V  V  E  S  G  Y  V  R  L  L   319

1312  TGGGAGAGGTGGGCACACTACAATTTGCTGAGCTGCATCGGAGCCGGACACTGCAGGTAGTGTTCGAGG 1380
       G  E  V  G  T  L  Q  F  A  E  L  H  R  S  R  T  L  Q  V  V  F  E  A   342

1381  CCTACCCCACCGCCCCACTGGTCCTGTGGTTCAAAGACAACACCCTGGGCGACTCCAGCGCTGGCGAAA 1449
       Y  P  P  T  V  L  W  F  K  D  N  R  T  L  G  D  S  S  A  G  E  I   365

1450  TCGCCCTGTCCACGCGCAACGTGTCGGAGACCCGGTATGTGTCAGAGCTGACACTGGTTCGCGTGAAGG 1518
       A  L  S  T  R  N  V  S  E  T  R  Y  V  S  E  L  T  L  V  R  V  K  V   388
```

Fig. 1B

```
1519  TGGCAGAGAGGCTGGCCACTACACCATGCGGGCCTTCCATGAGGATGCTGAGGTCCAGCTCTCCTTCCAGC  1587
       A  E  A  G  H  Y  T  M  R  A  F  H  E  D  A  E  V  Q  L  S  F  Q  L    411

1588  TACAGATCAATGTCCCTGTCCGAGTGCTGGAGCTAAGTGAGAGCCACCCTGACAGTGGGGAACAGACAG   1656
       Q  I  N  V  P  V  R  V  L  E  L  S  E  S  H  P  D  S  G  E  Q  T  V    434

1657  TCCGCTGTCGTGTGGCCGGGCATGCCCCAGCCGCCGAACATCATCTGGTCTGCCTGCAGAGACCTCAAAAAGGT  1725
       R  C  R  G  M  P  Q  P  P  N  I  I  W  S  A  C  R  D  L  K  R  C      457

1726  GTCCACGTGAGCTGCCGCCCCACGCTGCTGGGGAACAGTTCCGAAGAGAGAGAGCCAGTCCAGCTGGAGACTAACG  1794
       P  R  E  L  P  P  T  L  L  G  N  S  S  E  E  E  S  Q  L  E  T  N  V    480

1795  TGACGTACTGGGAGGAGGAGCAGGAGTTTGAGGTGGTGAGCACTCTGCTGCAGCACGTGGATCGGC       1863
       T  Y  W  E  E  E  Q  E  F  F  E  V  V  S  T  L  R  L  Q  H  V  D  R  P  503

1864  CACTGTCGGTGCGCTGCACGCTGCGCAACGCTGTGGGCCAGGACACGCAGGAGGTCATCGTGGTGCCAC     1932
       L  S  V  R  C  T  L  R  N  A  V  G  Q  D  T  Q  E  V  I  V  V  P  H    526

1933  ACTCCCTTGCCCTTTAAGGTGGTGGTGATCTCAGCCATCCTGGCCCTGGTGGTGCTCACCATCATCTCCC   2001
       S  L  P  F  K  V  V  V  I  S  A  I  L  A  L  V  V  L  T  I  I  S  L    549

2002  TTATCATCCTCATCATGCTTTGGCAGAAGAAGCCACGTTACGAGATCCGATGGAAGGTGATTGAGTCTG   2070
       I  I  L  I  M  L  W  Q  K  K  P  R  Y  E  I  R  W  K  V  I  E  S  V    572

2071  TGAGCTCTGACGGCCATGAGTACATCTACGTGGACCCCATGCAGCTGCCCTATGACTCCACGTGGGAGC   2139
       S  S  D  G  H  E  Y  I  Y  V  D  P  M  Q  L  P  Y  D  S  T  W  E  L    595

2140  TGCCGCGGGACCAGCTTGTGCTGGGACGCACCCTCGGCTCTGGGGCCTTTGGGCAGGTGGTGGAGGCCA    2208
       P  R  D  Q  L  V  L  G  R  T  L  G  S  G  A  F  G  Q  V  V  E  A  T    618
```

Fig. 1C

```
2209  CGGCTCATGGCCTGAGCCATTCTCAGGCCACGATGAAAGTGGCCGTCAAGATGCTTAAATCCACAGCCC  2277
       A  H  G  L  S  H  S  Q  A  T  M  K  V  A  V  K  M  L  K  S  T  A  R    641

2278  GCAGCAGTGAGAAGCAAGCCCTTATGTCGGAGCTGAAGATCATGAGTCACCTTGGGCCCACTGAACG    2346
       S  S  E  K  Q  A  L  M  S  E  L  K  I  M  S  H  L  G  P  H  L  N  V    664

2347  TGGTCAACCTGTTGGGGCCTGCACCAAAGGAGGACCCATCTATATCATCACTGAGTACTGCCGCTACG  2415
       V  N  L  L  G  A  C  T  K  G  G  P  I  Y  I  I  T  E  Y  C  R  Y  G    687

2416  GAGACCTGGTGGACTACCTGCACCGCAACAAACACACCTTCCTGCAGCACCACTCCGACAAGCGCCGCC 2484
       D  L  V  D  Y  L  H  R  N  K  H  T  F  L  Q  H  H  S  D  K  R  R  P    710

2485  CGCCCAGCGCGGAGCTCTACAGCAATGCTCTGCCCGTTGGGCTCCCCCTGCCCAGCCATGTGTCCTTGA 2553
       P  S  A  E  L  Y  S  N  A  L  P  V  G  L  P  L  P  S  H  V  S  L  T    733

2554  CCGGGGAGAGCGACGGTGGCTACATGGACATGAGCAAGGACGAGTCGGTGGACTATGTGCCCATGCTGG 2622
       G  E  S  D  G  G  Y  M  D  M  S  K  D  E  S  V  D  Y  V  P  M  L  D    756

2623  ACATGAAAGGAGACGTCAAATATGCAGACATCGAGTCCTCCAACTACATGGCCCCTTACGATAACTACG 2691
       M  K  G  D  V  K  Y  A  D  I  E  S  S  N  Y  M  A  P  Y  D  N  Y  V    779

2692  TTCCCTCTGCCCCTGAGAGGACGTGCCGAGCAACTTTGATCAACGAGTCTCCAGTGCTAAGCTACATGG 2760
       P  S  A  P  E  R  T  C  R  A  T  L  I  N  E  S  P  V  L  S  Y  M  D    802

2761  ACCTCGTGGGCTTCAGCTACCAGGTGCCAATGGCCGTCCAAGAACTGGAGTTTCTGGCCTCCACA    2829
       L  V  G  F  S  Y  Q  V  A  N  G  M  E  F  L  A  S  K  N  C  V  H  R    825

2830  GAGACCTGGCGGCTAGGAACGTGCTCATCTGTGAAGGCAAGCTGGTCAAGATCTGTGACTTTGGCCTGG 2898
       D  L  A  A  R  N  V  L  I  C  E  G  K  L  V  K  I  C  D  F  G  L  A    848
```

Fig. 1D

```
2899  CTCGAGACATCATGCGGGACTCGAATTACATCTCCAAAGGCAGCACCTTTTTGCCTTTAAAGTGGATGG  2967
       R   D   I   M   R   D   S   N   Y   I   S   K   G   S   T   F   L   P   L   K   W   M   A    871

2968  CTCCGGAGAGCATCTTCAACAGCCTCTACACCACCCTGAGCGACGTGTGGTCCTTCGGGATCCTGCTCT  3036
       P   E   S   I   F   N   S   L   Y   T   T   L   S   D   V   W   S   F   G   I   L   L   W    894

3037  GGGAGATCTTCACCTTGGGTGGCACCCCTTACCCAGAGCTGCCCATGAACGAGCAGTTCTACAATGCCA  3105
       E   I   F   T   L   G   G   T   P   Y   P   E   L   P   M   N   E   Q   F   Y   N   A   I    917

3106  TCAAACGGGTTACCGCATGGCCCAGCCTGCCCATGCCTCCGACGAGATCTATGAGATCATGCAGAAGT  3174
       K   R   G   Y   R   M   A   Q   P   A   H   A   S   D   E   I   Y   E   I   H   Q   K   C    940

3175  GCTGGGAAGAGAAGTTTGAGATTCGGCCCCCCTTCTCTCCCAGCTGGTGGATGAGGAGTTTCTGAGGAG  3243
       W   E   E   K   F   E   I   R   P   P   F   S   Q   L   V   L   L   E   R   L   L   G    963

3244  GCGAAGGTTACAAAAGAAGTACCAGCAGGTGGATGAGGAGTTTCTGAGGAGTGACCACCAGCCATCC  3312
       E   G   Y   K   K   K   Y   Q   Q   V   D   E   E   F   L   R   S   D   H   P   A   I   L    986

3313  TTCGGTCCCAGGCCCGCTTGCCTGGGTTCCATGGCCTCCGATCTCCCCTGGACACCAGCTCCGTCCTCT  3381
       R   S   Q   A   R   L   P   G   F   H   G   L   R   S   P   L   D   T   S   S   V   L   Y   1009

3382  ATACTGCCGTGCAGCCCAATGAGGGTGACAACGACTATATCATCCCCCTGCCTGACCCCAAACCCGAGG  3450
       T   A   V   Q   P   N   E   G   D   N   D   Y   I   I   P   L   P   D   D   P   K   P   E   V   1032

3451  TTGCTGACGAGGGCCCACTGGAGGGTCCCCCAGGGTTCCCCAGCTCCACCCTGAATGAAGTCAACACCT  3519
       A   D   E   G   P   L   E   G   P   S   L   A   S   S   T   L   N   E   V   N   T   S   1055

3520  CCTCAACCATCTCCTGTGACAGCCCCCTGGAGCCCCAGGACGAACCAGAGCCCCAGAGCCCCAGCTTGAGC  3588
       S   T   I   S   C   D   S   P   L   E   P   Q   D   E   P   E   P   Q   L   E   L   1078
```

Fig. 1E

```
3589  TCCAGGTGGAGCCGGAGCCAGAGCTGGAACAGTTGCCGGATTCGGGGTGCCTGGCGCCTCGGGCGGAAG  3657
       Q  V  E  P  E  P  E  L  E  Q  L  P  D  S  G  C  P  A  P  R  A  E  A    1101

3658  CAGAGGATAGCTTCCTGTAGGGGGCTGGCCCCTACCCCTGCCCCTGAAGCTCCCCCCTGCCAGCAC     3726
       E  D  S  F  L                                                          1106

3727  CCAGCATCTCCTGGCCTGGCCTTCCTGTCAGCCAGGCTGCCCTTATCAGCTGTCCCCTTC          3795

3796  TGGAAGCTTTCTGCTCCTGACGTGTGTGCCCCAAACCCTGGGGCTGGCTTAGGAGGCAAGAAAACTGC  3864

3865  AGGGGCCGTGACCAGCCCCTCTGCCTCCAGGGAGGCCAACTGACTCTGAGCCAGGGTTCCCCAGGGAAC 3933

3934  TCAGTTTTCCCATATGTAAGATGGGAAAGTTAGGCTTGATGACCCAGAATCTAGGATTCTCTCCCTGGC 4002

4003  TGACACGGTGGGGAGACCCGAATCCCCTGGGAAGATTCTTGAGTTACTGAGGTGGTAAATTAACAT     4071

4072  TTTTTCTGTTCAGCCAGCTACCCCTCCCTGGCTCCTCCTCGCACTTTTTATCCACCAGGA          4140

4141  GCTAGGGAAGAGACCCCTAGCCTGCCTCCCTGGCTTGAGCTTGAGCAGTGTTGCCTC             4209

4210  ATCCAGAAGAAAGCCAGTCTCCCTGCCCTATGATGCCAGTCCCTGCCGTTCCCTGGCCCGAGCTGGTCTGGG 4278

4279  GCCATTAGGCAGCCCTAATTAATGCTGGAGGCTGAGCCAAGTGCCTGTCCCTGTCCTCAGCCTGCAGCCCTTG 4347

4348  CCCAGGGCACTTGGAGCACACGCAGCCATAGCAAGCTTAATCCATTCACCAGAGTCTAGAAGGCCAGACGGGCCCCG 4416

4417  TGGGGCTTTTTCTTTATCACCCTCAGTCTTAATGTGCCAGTGTGGAGTGGCCACGTGTGTGCCAGTATATGGCCCTGG 4485

4486  CATCTGTGATGAGAATGTAAATGTAAATGTAAATGT... 4554
```
Fig. 1F

| | | |
|---|---|---|
| 4555 | CTCTGCATTGGACCTGCTATGAGGCTTTGGAGGAATCCCTCACCCTCTCTGGGCCTCAGTTTCCCCTTC | 4623 |
| 4624 | AAAAAATGAATAAGTCGGACTTATTAACTCTGAGTGCCTTGCCAGCACTAACATTCTAGAGTATTCCAG | 4692 |
| 4693 | GTGGTGCACATTTGTCCAGATGAAGCAAGGCCTATACCCTAAACTTCATCCTGGGGGTCAGCTGGGCTC | 4761 |
| 4762 | CTGGGAGATTCCAGATCACACATCTGGGACTCAGGAACCATGCCCCTTCCCCAGGCCCCCAG | 4830 |
| 4831 | CAAGTCTCAAGAACACAGCTGCACAGGCCTTGACTTAGAGTGACAGCCGGTGTCCTGGAAAGCCCCAAG | 4899 |
| 4900 | CAGCTGCCCCAGGGACATGGGAAGACCACGGGACCTCTTTCACTACCCACGATGACCTCCGGGGTATC | 4968 |
| 4969 | CTGGGCAAAAGGGACAAATGAGATCACCTCCTGCAGCCCACCACTCCAGCACCTGTGCCG | 5037 |
| 5038 | AGGTCTGCGTCGAAGAAGGATGTGAGAGGTGGCTGCTTTGGAGTTTGCCCCCTCACCCAGCTGCCCCAT | 5106 |
| 5107 | GGTACCCCAAGAAGGATGTGAGAGGTGGCTGCTTTGGAGTTTGCCCCCTCACCCAGCTGCCCCAT | 5175 |
| 5176 | CCCTGAGGCATGCGCTCCATGGGGCATTGGAGGTGCCAGGGAGTCAGGGTTGTAGCCAAGACGCCCCGCACGGGGA | 5244 |
| 5245 | CCCCAGCCCAGTGGGCATTGGAGGTGCAGGGAAGCTCAACCCCTGCATTGCAGGTTGGCACCTT | 5313 |
| 5314 | GGGTTGGGAAGGGGGTGCAGGAAGCTCAACCCCTGCATTGCAGGTTGGCACCTT | 5382 |
| 5383 | ACTTCCCTGGGATCCCCAGAGTTGGTCCAAGGAGGGAGAGTGGGTTCTCAATACGGTACCAAAGATATA | 5451 |
| 5452 | ATCACCTAGGTTTACAAATATTTTAGGACTCACGTTAACTCACATTTATACAGCAGAAATGCTATTTT | 5520 |
| 5521 | GTATGCTGTTAAGTTTTTCTATCTGTACTTTTTTTTAAGGAAAGATTTT | 5572 |

Fig. 1G

Figure 10
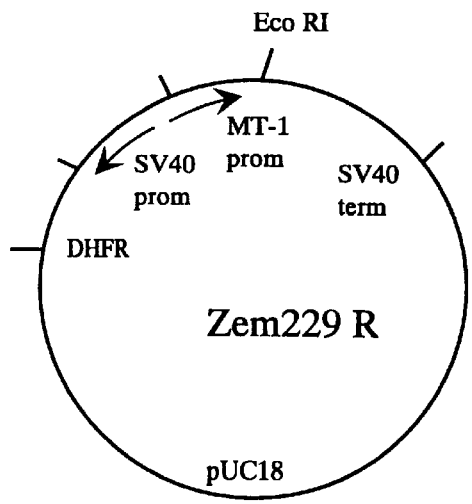
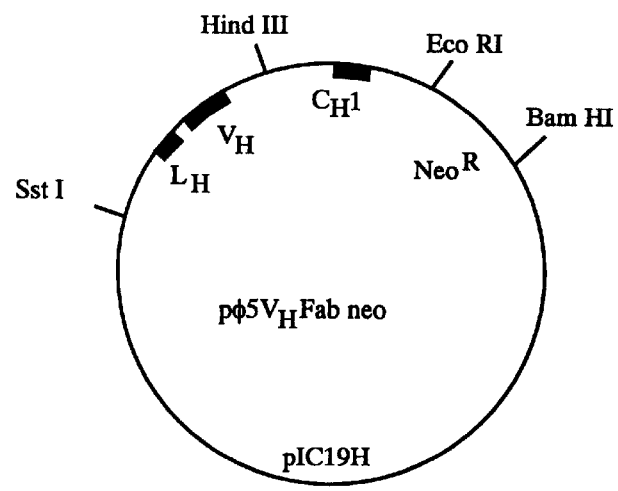
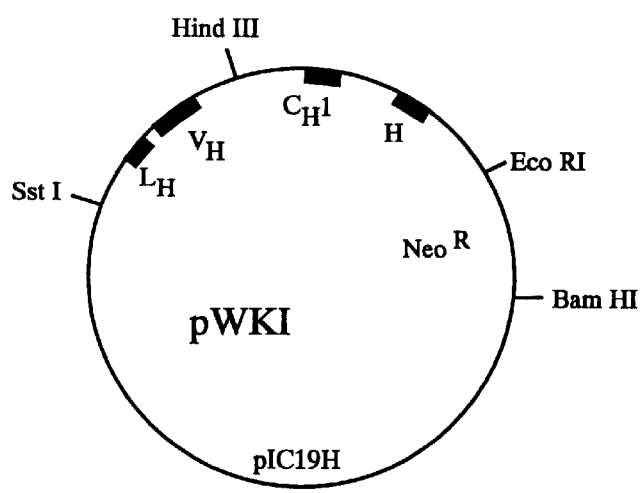

Figure 11A

```
  1  GCCCTGGGGACGGACCGTGGGCGGCGCGCAGCGGCGGGACGCGTTTTGGGGACGTGGTGGCCAGCGCCT
 70  TCCTGCAGACCCACAGGGAAGTACTCCCTTTGACCTCCGGGGAGCTGCGACCAGGTTATACGTTGCTGG

139  TGGAAAAGTGACAATTCTAGGAAAAGAGCTAAAAGCCGGATCGGTGACCGAAAGTTTCCCAGAGCTATG
                                                                        M
                                                                        1

208  GGGACTTCCCATCCGGCGTTCCTGGTCTTAGGCTGTCTTCTCACAGGGCTGAGCCTAATCCTCTGCCAG
      G  T  S  H  P  A  F  L  V  L  G  C  L  L  T  G  L  S  L  I  L  C  Q

277  CTTTCATTACCCTCTATCCTTCCAAATGAAAATGAAAAGGTTGTGCAGCTGAATTCATCCTTTTCTCTG
      L  S  L  P  S  I  L  P  N  E  N  E  K  V  V  Q  L  N  S  S  F  S  L

346  AGATGCTTTGGGGAGAGTGAAGTGAGCTGGCAGTACCCCATGTCTGAAGAAGAGAGCTCCGATGTGGAA
      R  C  F  G  E  S  E  V  S  W  Q  Y  P  M  S  E  E  E  S  S  D  V  E

415  ATCAGAAATGAAGAAAACAACAGCGGCCTTTTTGTGACGGTCTTGGAAGTGAGCAGTGCCTCGGCGGCC
      I  R  N  E  E  N  N  S  G  L  F  V  T  V  L  E  V  S  S  A  S  A  A

484  CACACAGGGTTGTACACTTGCTATTACAACCACACTCAGACAGAAGAGAATGAGCTTGAAGGCAGGCAC
      H  T  G  L  Y  T  C  Y  Y  N  H  T  Q  T  E  E  N  E  L  E  G  R  H

553  ATTTACATCTATGTGCCAGACCCAGATGTAGCCTTTGTACCTCTAGGAATGACGGATTATTTAGTCATC
      I  Y  I  Y  V  P  D  P  D  V  A  F  V  P  L  G  M  T  D  Y  L  V  I

622  GTGGAGGATGATGATTCTGCCATTATACCTTGTCGCACAACTGATCCCGAGACTCCTGTAACCTTACAC
      V  E  D  D  D  S  A  I  I  P  C  R  T  T  D  P  E  T  P  V  T  L  H

691  AACAGTGAGGGGGTGGTACCTGCCTCCTACGACAGCAGACAGGGCTTTAATGGGACCTTCACTGTAGGG
      N  S  E  G  V  V  P  A  S  Y  D  S  R  Q  G  F  N  G  T  F  T  V  G

760  CCCTATATCTGTGAGGCCACCGTCAAAGGAAAGAAGTTCCAGACCATCCCATTTAATGTTTATGCTTTA
      P  Y  I  C  E  A  T  V  K  G  K  K  F  Q  T  I  P  F  N  V  Y  A  L

829  AAAGCAACATCAGAGCTGGATCTAGAAATGGAAGCTCTTAAAACCGTGTATAAGTCAGGGGAAACGATT
      K  A  T  S  E  L  D  L  E  M  E  A  L  K  T  V  Y  K  S  G  E  T  I

898  GTGGTCACCTGTGCTGTTTTTAACAATGAGGTGGTTGACCTTCAATGGACTTACCCTGGAGAAGTGAAA
      V  V  T  C  A  V  F  N  N  E  V  V  D  L  Q  W  T  Y  P  G  E  V  K
```

Figure 11B

```
 967  GGCAAAGGCATCACAATACTGGAAGAAATCAAAGTCCCATCCATCAAATTGGTGTACACTTTGACGGTC
       G  K  G  I  T  I  L  E  E  I  K  V  P  S  I  K  L  V  Y  T  L  T  V

1036  CCCGAGGCCACGGTGAAAGACAGTGGAGATTACGAATGTGCTGCCCGCCAGGCTACCAGGGAGGTCAAA
       P  E  A  T  V  K  D  S  G  D  Y  E  C  A  A  R  Q  A  T  R  E  V  K

1105  GAAATGAAGAAAGTCACTATTTCTGTCCATGAGAAAGGTTTCATTGAAATCAAACCCACCTTCAGCCAG
       E  M  K  K  V  T  I  S  V  H  E  K  G  F  I  E  I  K  P  T  F  S  Q

1174  TTGGAAGCTGTCAACCTGCATGAAGTCAAACATTTTGTTGTAGAGGTGCGGGCCTACCCACCTCCCAGG
       L  E  A  V  N  L  H  E  V  K  H  F  V  V  E  V  R  A  Y  P  P  R

1243  ATATCCTGGCTGAAAAACAATCTGACTCTGATTGAAAATCTCACTGAGATCACCACTGATGTGGAAAAG
       I  S  W  L  K  N  N  L  T  L  I  E  N  L  T  E  I  T  T  D  V  E  K

1312  ATTCAGGAAATAAGGTATCGAAGCAAATTAAAGCTGATCCGTGCTAAGGAAGAAGACAGTGGCCATTAT
       I  Q  E  I  R  Y  R  S  K  L  K  L  I  R  A  K  E  E  D  S  G  H  Y

1381  ACTATTGTAGCTCAAAATGAAGATGCTGTGAAGAGCTATACTTTTGAACTGTTAACTCAAGTTCCTTCA
       T  I  V  A  Q  N  E  D  A  V  K  S  Y  T  F  E  L  L  T  Q  V  P  S

1450  TCCATTCTGGACTTGGTCGATGATCACCATGGCTCAACTGGGGGACAGACGGTGAGGTGCACAGCTGAA
       S  I  L  D  L  V  D  D  H  H  G  S  T  G  G  Q  T  V  R  C  T  A  E

1519  GGCACGCCGCTTCCTGATATTGAGTGGATGATATGCAAAGATATTAAGAAATGTAATAATGAAACTTCC
       G  T  P  L  P  D  I  E  W  M  I  C  K  D  I  K  K  C  N  N  E  T  S

1588  TGGACTATTTTGGCCAACAATGTCTCAAACATCATCACGGAGATCCACTCCCGAGACAGGAGTACCGTG
       W  T  I  L  A  N  N  V  S  N  I  I  T  E  I  H  S  R  D  R  S  T  V

1657  GAGGGCCGTGTGACTTTCGCCAAAGTGGAGGAGACCATCGCCGTGCGATGCCTGGCTAAGAATCTCCTT
       E  G  R  V  T  F  A  K  V  E  E  T  I  A  V  R  C  L  A  K  N  L  L

1726  GGAGCTGAGAACCGAGAGCTGAAGCTGGTGGCTCCCACCCTGCGTTCTGAACTCACGGTGGCTGCTGCA
       G  A  E  N  R  E  L  K  L  V  A  P  T  L  R  S  E  L  T  V  A  A  A

1795  GTCCTGGTGCTGTTGGTGATTGTGATCATCTCACTTATTGTCCTGGTTGTCATTTGGAAACAGAAACCG
       V  L  V  L  L  V  I  V  I  I  S  L  I  V  L  V  V  I  W  K  Q  K  P
```

Figure 11C

```
1864  AGGTATGAAATTCGCTGGAGGGTCATTGAATCAATCAGCCCGGATGGACATGAATATATTTATGTGGAC
       R  Y  E  I  R  W  R  V  I  E  S  I  S  P  D  G  H  E  Y  I  Y  V  D

1933  CCGATGCAGCTGCCTTATGACTCAAGATGGGAGTTTCCAAGAGATGGACTAGTGCTTGGTCGGGTCTTG
       P  M  Q  L  P  Y  D  S  R  W  E  F  P  R  D  G  L  V  L  G  R  V  L

2002  GGGTCTGGAGCGTTTGGGAAGGTGGTTGAAGGAACAGCCTATGGATTAAGCCGGTCCCAACCTGTCATG
       G  S  G  A  F  G  K  V  V  E  G  T  A  Y  G  L  S  R  S  Q  P  V  M

2071  AAAGTTGCAGTGAAGATGCTAAAACCCACGGCCAGATCCAGTGAAAAACAAGCTCTCATGTCTGAACTG
       K  V  A  V  K  M  L  K  P  T  A  R  S  S  E  K  Q  A  L  M  S  E  L

2140  AAGATAATGACTCACCTGGGGCCACATTTGAACATTGTAAACTTGCTGGGAGCCTGCACCAAGTCAGGC
       K  I  M  T  H  L  G  P  H  L  N  I  V  N  L  L  G  A  C  T  K  S  G

2209  CCCATTTACATCATCACAGAGTATTGCTTCTATGGAGATTTGGTCAACTATTTGCATAAGAATAGGGAT
       P  I  Y  I  I  T  E  Y  C  F  Y  G  D  L  V  N  Y  L  H  K  N  R  D

2278  AGCTTCCTGAGCCACCACCCAGAGAAGCCAAAGAAAGAGCTGGATATCTTTGGATTGAACCCTGCTGAT
       S  F  L  S  H  H  P  E  K  P  K  K  E  L  D  I  F  G  L  N  P  A  D

2347  GAAAGCACACGGAGCTATGTTATTTTATCTTTTGAAAACAATGGTGACTACATGGACATGAAGCAGGCT
       E  S  T  R  S  Y  V  I  L  S  F  E  N  N  G  D  Y  M  D  M  K  Q  A

2416  GATACTACACAGTATGTCCCCATGCTAGAAAGGAAAGAGGTTTCTAAATATTCCGACATCCAGAGATCA
       D  T  T  Q  Y  V  P  M  L  E  R  K  E  V  S  K  Y  S  D  I  Q  R  S

2485  CTCTATGATCGTCCAGCCTCATATAAGAAGAAATCTATGTTAGACTCAGAAGTCAAAAACCTCCTTTCA
       L  Y  D  R  P  A  S  Y  K  K  K  S  M  L  D  S  E  V  K  N  L  L  S

2554  GATGATAACTCAGAAGGCCTTACTTTATTGGATTTGTTGAGCTTCACCTATCAAGTTGCCCGAGGAATG
       D  D  N  S  E  G  L  T  L  L  D  L  L  S  F  T  Y  Q  V  A  R  G  M

2623  GAGTTTTTGGCTTCAAAAAATTGTGTCCACCGTGATCTGGCTGCTCGCAACGTCCTCCTGGCACAAGGA
       E  F  L  A  S  K  N  C  V  H  R  D  L  A  A  R  N  V  L  L  A  Q  G

2692  AAAATTGTGAAGATCTGTGACTTTGGCCTGGCCAGAGACATCATGCATGATTCGAACTATGTGTCGAAA
       K  I  V  K  I  C  D  F  G  L  A  R  D  I  M  H  D  S  N  Y  V  S  K

2761  GGCAGTACCTTTCTGCCCGTGAAGTGGATGGCTCCTGAGAGCATCTTTGACAACCTCTACACCACACTG
       G  S  T  F  L  P  V  K  W  M  A  P  E  S  I  F  D  N  L  Y  T  T  L
```

Figure 11D

```
2830 AGTGATGTCTGGTCTTATGGCATTCTGCTCTGGGAGATCTTTTCCCTTGGTGGCACCCCTTACCCCGGC
      S  D  V  W  S  Y  G  I  L  L  W  E  I  F  S  L  G  G  T  P  Y  P  G

2899 ATGATGGTGGATTCTACTTTCTACAATAAGATCAAGAGTGGGTACCGGATGGCCAAGCCTGACCACGCT
      M  M  V  D  S  T  F  Y  N  K  I  K  S  G  Y  R  M  A  K  P  D  H  A

2968 ACCAGTGAAGTCTACGAGATCATGGTGAAATGCTGGAACAGTGAGCCGGAGAAGAGACCCTCCTTTTAC
      T  S  E  V  Y  E  I  M  V  K  C  W  N  S  E  P  E  K  R  P  S  F  Y

3037 CACCTGAGTGAGATTGTGGAGAATCTGCTGCCTGGACAATATAAAAAGAGTTATGAAAAAATTCACCTG
      H  L  S  E  I  V  E  N  L  L  P  G  Q  Y  K  K  S  Y  E  K  I  H  L

3106 GACTTCCTGAAGAGTGACCATCCTGCTGTGGCACGCATGCGTGTGGACTCAGACAATGCATACATTGGT
      D  F  L  K  S  D  H  P  A  V  A  R  M  R  V  D  S  D  N  A  Y  I  G

3175 GTCACCTACAAAAACGAGGAAGACAAGCTGAAGGACTGGGAGGGTGGTCTGGATGAGCAGAGACTGAGC
      V  T  Y  K  N  E  E  D  K  L  K  D  W  E  G  G  L  D  E  Q  R  L  S

3244 GCTGACAGTGGCTACATCATTCCTCTGCCTGACATTGACCCTGTCCCTGAGGAGGAGGACCTGGGCAAG
      A  D  S  G  Y  I  I  P  L  P  D  I  D  P  V  P  E  E  E  D  L  G  K

3313 AGGAACAGACACAGCTCGCAGACCTCTGAAGAGAGTGCCATTGAGACGGGTTCCAGCAGTTCCACCTTC
      R  N  R  H  S  S  Q  T  S  E  E  S  A  I  E  T  G  S  S  S  T  F

3382 ATCAAGAGAGAGGACGAGACCATTGAAGACATCGACATGATGGACGACATCGGCATAGACTCTTCAGAC
      I  K  R  E  D  E  T  I  E  D  I  D  M  M  D  D  I  G  I  D  S  S  D

3451 CTGGTGGAAGACAGCTTCCTGTAACTGGCGGATTCGAGGGGTTCCTTCCACTTCTGGGGCCACCTCTGG
      L  V  E  D  S  F  L
                       1089

3520 ATCCCGTTCAGAAAACCACTTTATTGCAATGCGGAGGTTGAGAGGAGGACTTGGTTGATGTTTAAAGAG
3589 AAGTTCCCAGCCAAGGGCCTCGGGGAGCGTTCTAAATATGAATGAATGGGATATTTTGAAATGAACTTT
3658 GTCAGTGTTGCCTCTTGCAATGCCTCAGTAGCATCTCAGTGGTGTGTGAAGTTTGGAGATAGATGGATA
3727 AGGGAATAATAGGCCACAGAAGGTGAACTTTGTGCTTCAAGGACATTGGTGAGAGTCCAACAGACACAA
3796 TTTATACTGCGACAGAACTTCAGCATTGTAATTATGTAAATAACTCTAACCAAGGCTGTGTTTAGATTG
3865 TATTAACTATCTTCTTTGGACTTCTGAAGAGACCACTCAATCCATCCTGTACTTCCCTCTTGAAACCTG
3934 ATGTAGCTGCTGTTGAACTTTTTAAAGAAGTGCATGAAAAACCATTTTTGAACCTTAAAAGGTACTGGT
4003 ACTATAGCATTTTGCTATCTTTTTTAGTGTTAAAGAGATAAAGAATAATAAG
```

BIOLOGICALLY ACTIVE DIMERIZED AND MULTIMERIZED POLYPEPTIDE FUSIONS

CROSS REFERENCE TO RELATED APPLICATION

This application is a divisional of U.S. application Ser. No. 8/477,329, filed Jun. 7, 1995, now U.S. Pat. No. 5,750,375 which is a continuation of U.S. application Ser. No. 180,195, filed Jan. 11, 1994,now U.S. Pat. No. 5,567,584, which is a continuation of U.S. application Ser. No. 07/634,510 filed Dec. 27, 1990, now abandoned, which is a continuation-in-part of U.S. application Ser. No. 7/347,291, filed May 2, 1989, now U.S. Pat. No. 5,155,027 which is a continuation-in-part of U.S. application Ser. No/7/146,877, filed Jan. 22, 1988, now abandoned.

TECHNICAL FIELD Technical Field

The present invention is generally directed toward the expression of proteins, and more specifically, toward the expression of growth factor receptor analogs and biologically active dimerized polypeptide fusions.

BACKGROUND OF THE INVENTION

In higher eucaryotic cells, the interaction between receptors and ligands (e.g., hormones) is of central importance in the transmission of and response to a variety of extracellular signals. It is generally accepted that hormones and growth factors elicit their biological functions by binding to specific recognition sites (receptors) in the plasma membranes of their target cells. Upon ligand binding, a receptor undergoes a conformational change, triggering secondary cellular responses that result in the activation or inhibition of intracellular processes. The stimulation or blockade of such an interaction by pharmacological means has important therapeutic implications for a wide variety of illnesses.

Ligands fall into two classes: those that have stimulatory activity, termed agonists; and those that block the effects elicited by the original ligands, termed antagonists. The discovery of agonists that differ in structure and composition from the original ligand may be medically useful. In particular, agonists that are smaller than the original ligand may be especially useful. The bioavailability of these smaller agonists may be greater than that of the original ligand. This may be of particular importance for topical applications and for instances when diffusion of the agonist to its target sites is inhibited by poor circulation. Agonists may also have slightly different spectra of biological activity and/or different potencies, allowing them to be used in very specific situations. Agonists that are smaller and chemically simpler than the native ligand may be produced in greater quantity and at lower cost. The identification of antagonists which specifically block, for example, growth factor receptors has important pharmaceutical applications. Antagonists that block receptors against the action of endogenous, native ligand may be used as therapeutic agents for conditions including atherosclerosis, autocrine tumors, fibroplasia and keloid formation.

The discovery of new ligands that may be used in pharmaceutical applications has centered around designing compounds by chemical modification, complete synthesis, and screening potential ligands by complex and costly screening procedures. The process of designing a new ligand usually begins with the alteration of the structure of the original effector molecule. If the original effector molecule is known to be chemically simple, for example, a catecholamine or prostaglandin, the task is relatively straightforward. However, if the ligand is structurally complex, for example, a peptide hormone or a growth factor, finding a molecule which is functionally equivalent to the original ligand becomes extremely difficult.

Currently, potential ligands are screened using radioligand binding methods (Lefkowitz et al., *Biochem, Biophys. Res. Comm.* 60: 703–709, 1974; Aurbach et al., *Science* 186: 1223–1225, 1974; Atlas et al., *Proc. Natl. Acad. Sci. USA* 71: 4246–4248, 1974). Potential ligands can be directly assayed by binding the radiolabeled compounds to responsive cells, to the membrane fractions of disrupted cells, or to solubilized receptors. Alternatively, potential ligands may be screened by their ability to compete with a known labeled ligand for cell surface receptors.

The success of these procedures depends on the availability of reproducibly high quality preparations of membrane fractions or receptor molecules, as well as the isolation of responsive cell lines. The preparation of membrane fractions and soluble receptor molecules involves extensive manipulations and complex purification steps. The isolation of membrane fractions requires gentle manipulation of the preparation, a procedure which does not lend itself to commercial production. It is very difficult to maintain high biological activity and biochemical purity of receptors when they are purified by classical protein chemistry methods. Receptors, being integral membrane proteins, require cumbersome purification procedures, which include the use of detergents and other solvents that interfere with their biological activity. The use of these membrane preparations in ligand binding assays typically results in low reproducibility due to the variability of the membrane preparations.

As noted above, ligand binding assays require the isolation of responsive cell lines. Often, only a limited subset of cells is responsive to a particular agent, and such cells may be responsive only under certain conditions. In addition, these cells may be difficult to grow in culture or may possess a low number of receptors. Currently available cell types responsive to platelet-derived growth factor (PDGF), for example, contain only a low number (up to $4 \times 10^5$; see Bowen-Pope and Ross, *J. Biol. Chem.* 257: 5161–5171, 1982) of receptors per cell, thus requiring large numbers of cells to assay PDGF analogs or antagonists.

Presently, only a few naturally-occurring secreted receptors, for example, the interleukin-2 receptor (IL-2-R) have been identified. Rubin et al. (*J. Immun.* 135: 3172–3177, 1985) have reported the release of large quantities of IL-2-R into the culture medium of activated T-cell lines. Bailon et al. (*Bio/Technology* 5: 1195–1198, 1987) have reported the use of a matrix-bound interleukin-2 receptor to purify recombinant interleukin-2.

Three other receptors have been secreted from mammalian cells. The insulin receptor (Ellis et al., *J. Cell Biol.* 150: 14a, 1987), the HIV-1 envelope glyco-protein cellular receptor CD4 (Smith et al., *Science* 238: 1704–1707, 1987), the murine IL-7 receptor (*Cell* 60: 941–951, 1990) and the epidermal growth factor (EGF) receptor (Livneh et al., *J. Biol. Chem.* 261: 12490–12497, 1986) have been secreted from mammalian cells using truncated cDNAs that encode portions of the extracellular domains.

Naturally-occurring, secreted receptors have not been widely identified, and there have been only a limited number of reports of secreted recombinant receptors. Secreted receptors may be used in a variety of assays, which include assays to determine the presence of ligand in biological fluids and assays to screen for potential agonists and antagonists.

Current methods for ligand screening and ligand/receptor binding assays have been limited to those using preparations of whole cells or cell membranes for as a source for receptor molecules. The low reproducibility and high cost of producing such preparations does not lend itself to commercial production. There is therefore a need in the art for a method of producing secreted receptors. There is a further need in the art for an assay system that permits high volume screening of compounds that may act on higher eucaryotic cells via specific surface receptors. This assay system should be rapid, inexpensive and adaptable to high volume screening. The present invention discloses such a method and assay system, and further provides other related advantages.

DISCLOSURE OF INVENTION

Briefly stated, the present invention discloses methods for producing secreted receptor analogs, including receptor analogs and secreted platelet-derived growth factor receptor (PDGF-R) analogs. In addition, the present invention discloses methods for producing secreted biologically active dimerized polypeptide fusions.

Within one aspect of the invention a method for producing a secreted PDGF-R analog is disclosed, comprising (a) introducing into a eukaryotic host cell a DNA construct comprising a transcriptional promoter operatively linked to a secretory signal sequence followed downstream of and in proper reading frame with a DNA sequence encoding at least a portion of the ligand-binding domain of a PDGF-R, the portion including a ligand-binding domain; (b) growing the host cell in an appropriate growth medium under physiological conditions to allow the secretion of a PDGF-R analog encoded by said DNA sequence; and (c) isolating the PDGF-R analog from the host cell.

Within one embodiment of the present invention, a PDGF-R analog comprising the amino acid sequence of FIGS. 1A–1B (Sequence ID Numbers 1 and 2) from isoleucine, number 29, to methionine, number 441, is secreted. Within another embodiment, a PDGF-R analog comprising the amino acid sequence of FIGS. 1A–1B (Sequence ID Numbers 1 and 2) from isoleucine, number 29 to lysine, number 531 is secreted. Within yet another embodiment of the invention, a PDGF-R analog comprising the amino acid sequence of FIGS. 11A–11B (Sequence ID Numbers 35 and 36) from glutamine, number 24 to glutamic acid, number 524 is secreted.

Yet another aspect of the present invention discloses a method for producing a secreted, biologically active dimerized polypeptide fusion. The method generally comprises a) introducing into a eukaryotic host cell a DNA construct comprising a transcriptional promoter operatively linked to a secretory signal sequence followed downstream by and in proper reading frame with a DNA sequence encoding a non-immunoglobulin polypeptide requiring dimerization for biological activity joined to a dimerizing protein; (b) growing the host cell in an appropriate growth medium under physiological conditions to allow the secretion of a dimerized polypeptide fusion encoded by said DNA sequence; and (c) isolating the biologically active dimerized polypeptide fusion from the host cell.

Within one embodiment, the dimerizing protein is yeast invertase. Within another embodiment, the dimerizing protein is at least a portion of an immunoglobulin light chain. Within another embodiment, the dimerizing protein is at least a portion of an immunoglobulin heavy chain.

In another aspect of the invention, a method is disclosed for producing a secreted, biologically active dimerized polypeptide fusion, comprising (a) introducing into a eukaryotic host cell a first DNA construct comprising a transcriptional promoter operatively linked to a first secretory signal sequence followed downstream by and in proper reading frame with a first DNA sequence encoding a non-immunoglobulin polypeptide requiring dimerization for biological activity joined to an immunoglobulin light chain constant region; (b) introducing into the host cell a second DNA construct comprising a transcriptional promoter operatively linked to a second secretory signal sequence followed downstream by and in proper reading frame with a second DNA sequence encoding an immunoglobulin heavy chain constant region domain selected from the group consisting of $C_H1$, $C_H2$, $C_H3$, and $C_H4$; (c) growing the host cell in an appropriate growth medium under physiological conditions to allow the secretion of a dimerized polypeptide fusion encoded by said first and second DNA sequences; and (d) isolating the dimerized polypeptide fusion from the host cell. In one embodiment, the second DNA sequence further encodes an immuunoglobulin heavy chain hinge region wherein the hinge region is joined to the heavy chain constant region domain. In a preferred embodiment, the second DNA sequence further encodes an immunoglobulin variable region joined upstream of and in proper reading frame with the immunoglobulin heavy chain constant region.

In another aspect of the invention, a method is disclosed for producing a secreted, biologically active dimerized polypeptide fusion, comprising (a) introducing into a eukaryotic host cell a first DNA construct comprising a transcriptional promoter operatively linked to a first secretory signal sequence followed downstream by and in proper reading frame with a first DNA sequence encoding a non-immunoglobulin polypeptide requiring dimerization for biological activity joined to an immunoglobulin heavy chain constant region domain selected from the group consisting of $C_H1$, $C_H2$, $C_H3$, and $C_H4$; (b) introducing into the host cell a second DNA construct comprising a transcriptional promoter operatively linked to a second secretory signal sequence followed downstream by and in proper reading frame with a second DNA sequence encoding an immunoglobulin light chain constant region; (c) growing the host cell in an appropriate growth medium under physiological conditions to allow the secretion of a dimerized polypeptide fusion encoded by said first and second DNA sequences; and (d) isolating the dimerized polypeptide fusion from the host cell. In one embodiment, the first DNA sequence further encodes an immunoglobulin heavy chain hinge region wherein the hinge region is joined to the heavy chain constant region domain. In a preferred embodiment, the second DNA sequence further encodes an immunoglobulin variable region joined upstream of and in proper reading frame with the immunoglobulin light chain constant region.

In another aspect of the invention, a method is disclosed for producing a secreted, biologically active dimerized polypeptide fusion, comprising (a) introducing into a eukaryotic host cell a DNA construct comprising a transcriptional promoter operatively linked to a secretory signal sequence followed downstream by and in proper reading frame with a DNA sequence encoding a non-immunoglobulin polypeptide requiring dimerization for biological activity joined to an immunoglobulin heavy chain constant region domain selected from the group consisting of $C_H1$, $C_H2$, $C_H3$, and $C_H4$; (b) growing the host cell in an appropriate growth medium under physiological conditions to allow the secretion of a dimerized polypeptide fusion encoded by said first and second DNA sequences; and (c)

isolating the biologically active dimerized polypeptide fusion from the host cell. In one embodiment, the DNA sequence further encodes an immunoglobulin heavy chain hinge region wherein the hinge region is joined to the heavy chain constant region domain.

In another aspect of the invention, a method is disclosed for producing a secreted, biologically active dimerized polypeptide fusion, comprising (a) introducing into a eukaryotic host cell a first DNA construct comprising a transcriptional promoter operatively linked to a first secretory signal sequence followed downstream by and in proper reading frame with a first DNA sequence encoding a first polypeptide chain of a non-immunoglobulin polypeptide dimer requiring dimerization for biological activity joined to an immunoglobulin heavy chain constant region domain, selected from the group consisting of $C_H1$, $C_H2$, $C_H3$, and $C_H4$; (b) introducing into the host cell a second DNA construct comprising a transcriptional promoter operatively linked to a second secretory signal sequence followed downstream by and in proper reading frame with a second DNA sequence encoding a second polypeptide chain of the non-immunoglobulin polypeptide dimer joined to an immunoglobulin light chain constant region domain; (c) growing the host cell in an appropriate growth medium under physiological conditions to allow the secretion of a dimerized polypeptide fusion encoded by said first and second DNA sequences wherein said dimerized polypeptide fusion exhibits biological activity characteristic of said non-immunoglobulin polypeptide dimer; and (d) isolating the dimerized polypeptide fusion from the host cell. In one embodiment the first DNA sequence further encodes an immunoglobulin heavy chain hinge region domain wherein the hinge region is joined to the immunoglobulin heavy chain constant region domain.

Within one embodiment of the present invention, a biologically active dimerized polypeptide fusion comprising the amino acid sequence of FIGS. 1A–1B (Sequence ID Numbers 1 and 2) from isoleucine, number 29, to methionine, number 441, is secreted. Within another embodiment, a biologically active dimerized polypeptide fusion comprising the amino acid sequence of FIGS. 1A–1B (Sequence ID Numbers 1 and 2) from isoleucine, number 29 to lysine, number 531 is secreted. Within another embodiment of the invention, a biologically active dimerized polypeptide fusion comprising the amino acid sequence of FIGS. 11A–11B (Sequence ID Numbers 35 and 36) from glutamine, number 24 to glutamic acid, number 524 is secreted. Within yet another embodiment of the invention, a biologically active dimerized polypeptide fusion comprising the amino acid sequence of FIGS. 1A–1B (Sequence ID Numbers 1 and 2) from isoleucine, number 29 to lysine, number 531 dimerized to the amino acid sequence of FIGS. 11A–11B (sequence ID Numbers 35 and 36) from glutamine, number 24 to glutamic acid, number 524 is secreted.

In yet another aspect of the invention, a method is disclosed for producing a secreted receptor analog, comprising (a) introducing into a eukaryotic host cell a DNA construct comprising a transcriptional promoter operatively linked to at least one secretory signal sequence followed downstream by and in proper reading frame with a DNA sequence encoding a ligand-binding domain of a receptor requiring dimerization for biological activity joined to a dimerizing protein; (b) growing the host cell in an appropriate growth medium under physiological conditions to allow the secretion of a receptor analog encoded by said DNA sequence; and (c) isolating the receptor analog from the host cell.

In yet another aspect of the invention, a method is disclosed for producing a secreted receptor analog, comprising (a) introducing into a eukaryotic host cell a first DNA construct comprising a transcriptional promoter operatively linked to a first secretory signal sequence followed downstream by and in proper reading frame with a first DNA sequence encoding a ligand-binding domain of a receptor requiring dimerization for biological activity joined to an immunoglobulin light chain constant region; (b) introducing into the host cell a second DNA construct comprising a transcriptional promoter operatively linked to a second secretory signal sequence followed downstream by and in proper reading frame with a second DNA sequence encoding an immunoglobulin heavy chain constant region domain, selected from the group consisting of $C_H1$, $C_H2$, $C_H3$, and $C_H4$; (c) growing the host cell in an appropriate growth medium under physiological conditions to allow the secretion of a receptor analog encoded by said first and second DNA sequences; and (d) isolating the receptor analog from the host cell. In one embodiment, the second DNA sequence further encodes an immunoglobulin heavy chain hinge region wherein the hinge region is joined to the heavy chain constant region domain. In a preferred embodiment, the second DNA sequence further encodes an immunoglobulin variable region joined upstream of and in proper reading frame with the immunoglobulin heavy chain constant region.

In another aspect of the invention, a method is disclosed for producing a secreted receptor analog, comprising (a) introducing into a eukaryotic host cell a DNA construct comprising a transcriptional promoter operatively linked to a secretory signal sequence followed downstream by and in proper reading frame with a DNA sequence encoding a ligand-binding domain of a receptor requiring dimerization for biological activity joined to an immunoglobulin heavy chain constant region domain, selected from the group $C_H1$, $C_H2$, $C_H3$, and $C_H4$; (b) growing the host cell in an appropriate growth medium under physiological conditions to allow the secretion of the receptor analog; and (c) isolating the receptor analog from the host cell. In one embodiment, the DNA sequence further encodes an immunoglobulin heavy chain hinge region wherein the hinge region is joined to the heavy chain constant region domain.

In another aspect of the invention, a method is disclosed for producing a secreted receptor analog, comprising (a) introducing into a eukaryotic host cell a first DNA construct comprising a transcriptional promoter operatively linked to a first secretory signal sequence followed downstream of and in proper reading frame with a first DNA sequence encoding a ligand-binding domain of a receptor requiring dimerization for biological activity joined to an immunoglobulin heavy chain constant region domain, selected from the group $C_H1$, $C_H2$, $C_H3$, and $C_H4$; (b) introducing into the host cell a second DNA construct comprising a transcriptional promoter operatively linked to a second secretory signal sequence followed downstream by and in proper reading frame with a second DNA sequence encoding an immunoglobulin light chain constant region; (c) growing the host cell in an appropriate growth medium under physiological conditions to allow the secretion of a receptor analog encoded by said first and second DNA sequences; and (d) isolating the receptor analog from the host cell. In one embodiment, the first DNA sequence further encodes an immunoglobulin heavy chain hinge region wherein the hinge region is joined to the heavy chain constant region domain. In a preferred embodiment, the second DNA sequence further encodes an immunoglobulin variable region joined upstream of and in proper reading frame with the immunoglobulin light chain constant region.

In another aspect of the invention, a method is disclosed for producing a secreted receptor analog, comprising (a) introducing into a eukaryotic host cell a first DNA construct comprising a transcriptional promoter operatively linked to a first secretory signal sequence followed downstream in proper reading frame by a first DNA sequence encoding a first polypeptide chain of a ligand-binding domain of a receptor requiring dimerization for biological activity joined to an immunoglobulin heavy chain constant region domain, selected from the group $C_H1$, $C_H2$, $C_H3$, and $C_H4$; (b) introducing into the host cell a second DNA construct comprising a transcriptional promoter operatively linked to a second secretory signal sequence followed downstream by and in proper reading frame with a second DNA sequence encoding a second polypeptide chain of the ligand-binding domain of said receptor joined to an immunoglobulin light chain constant region domain; (c) growing the host cell in an appropriate growth medium under physiological conditions to allow the secretion of a receptor analog encoded by said first and second DNA sequences; and (d) isolating the receptor analog from the host cell. In one embodiment the first DNA sequence further encodes an immunoglobulin heavy chain hinge region domain wherein the hinge region is joined to the immunoglobulin heavy chain constant region domain.

Host cells for use in the present invention include cultured mammalian cells and fungal cells. In a preferred embodiment strains of the yeast *Saccharomyces cerevisiae* are used as host cells. Within another preferred embodiment cultured rodent myeloma cells are used as host cells.

Within one embodiment of the present invention, a receptor analog is a PDGF-R analog comprising the amino acid sequence of FIG. 1 (Sequence ID Numbers 1 and 2) from isoleucine, number 29, to methionine, number 441. Within another embodiment a PDGF-R analog comprises the amino acid sequence of FIG. 1 (Sequence ID Numbers 1 and 2) from isoleucine, number 29, to lysine, number 531. Within another embodiment of the invention, a PDGF-R analog comprises the amino acid sequence of FIG. 11 (Sequence ID Numbers 35 and 36) from glutamine, number 24 to glutamic acid, number 524 is secreted. Within yet another embodiment of the invention, a PDGF-R analog comprises the amino acid sequence of FIG. 1 (Sequence ID Numbers 1 and 2) from isoleucine, number 29 to lysine, number 531 and the amino acid sequence of FIG. 11 (Sequence ID Numbers 35 and 36) from glutamine, number 24 to glutamic acid, number 524 is secreted.

PDGF-R analogs produced by the above-disclosed methods may be used, for instance, within a method for determining the presence of human PDGF or an isoform thereof in a biological sample.

A method for determining the presence of human PDGF or an isoform thereof in a biological sample is disclosed and comprises (a) incubating a polypeptide comprising a PDGF receptor analog fused to a dimerizing protein with a biological sample suspected of containing PDGF or an isoform thereof under conditions that allow the formation of receptor/ligand complexes; and (b) detecting the presence of receptor/ligand complexes, and therefrom determining the presence of PDGF or an isoform thereof. Suitable biological samples in this regard include blood, urine, plasma, serum, platelet and other cell lysates, platelet releasates, cell suspensions, cell-conditioned culture media, and chemically or physically separated portions thereof.

These and other aspects of the present invention will become evident upon reference to the following detailed description and attached drawings.

BRIEF DESCRIPTION OF THE DRAWINGS

FIGS. 1A–1D (Sequence ID Numbers 1 and 2) illustrate the nucleotide sequence of a representative PDGF β-receptor cDNA and the derived amino acid sequence of the primary translation product and corresponds to Sequence ID Number 1). Numbers above the lines refer to the nucleotide sequence; numbers below the lines refer to the amino acid sequence.

FIG. 10 illustrates the constructions Zem229R, p$\phi$5V$_H$Fab-neo and pWKI. Symbols used are set forth in FIG. 9.

FIGS. 11A–11D illustrate the sequence of a representative PDGF α-receptor CDNA and the deduced amino acid sequence (using standard one-letter codes) encoded by the CDNA and corresponds to Sequence ID Numbers 35 and 36. Numbers at the ends of the lines refer to nucleotide positions. Numbers below the sequence refer to amino acid positions.

DETAILED DESCRIPTION OF THE INVENTION

Figure 2:
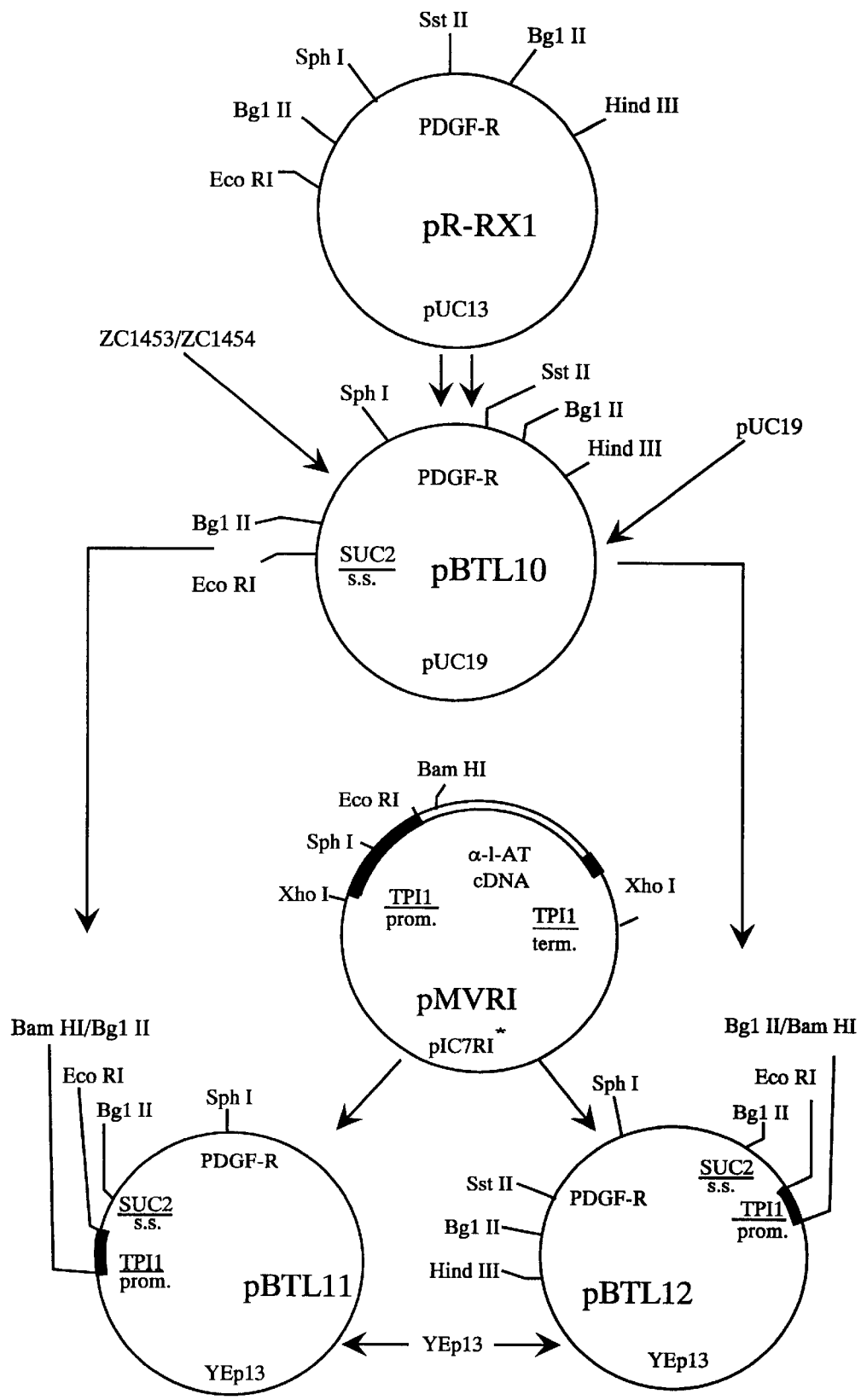
FIG. 2 illustrates the construction of pBTL10, pBTL11 and pBTL12.

Prior to setting forth the invention, it may be helpful to an understanding thereof to set forth definitions of certain terms to be used hereinafter.

DNA Construct

A DNA molecule, or a clone of such a molecule, either single- or double-stranded that has been modified through human intervention to contain segments of DNA combined and juxtaposed in a manner that as a whole would not otherwise exist in nature.

DNA constructs contain the information necessary to direct the expression and/or secretion of DNA sequences encoding polypeptides of interest. DNA constructs will generally include promoters, enhancers and transcription terminators. DNA constructs containing the information necessary to direct the secretion of a polypeptide will also contain at least one secretory signal sequence.

Secretory Signal Sequence

A DNA sequence encoding a secretory peptide. A secretory peptide is an amino acid sequence that acts to direct the secretion of a mature polypeptide or protein from a cell. Secretory peptides are characterized by a core of hydrophobic amino acids and are typically (but not exclusively) found at the amino termini of newly sythesized proteins. Very often the secretory peptide is cleaved from the mature protein during secretion. Such secretory peptides contain processing sites that allow cleavage of the signal peptides from the mature proteins as it passes through the secretory pathway. Processing sites may be encoded within the signal peptide or may be added to the signal peptide by, for example, in vitro mutagenesis. Certain secretory peptides may be used in concert to direct the secretion of polypeptides and proteins. One such secretory peptide that may be used in combination with other secretory peptides is the third domain of the yeast Barrier protein.

Receptor Analog

A non-immunoglobulin polypeptide comprising a portion of a receptor which is capable of binding ligand and/or is recognized by anti-receptor antibodies. The amino acid sequence of the receptor analog may contain additions, substitutions or deletions as compared to the native receptor sequence. A receptor analog may be, for example, the ligand-binding domain of a receptor joined to another protein. Platelet-derived growth factor receptor (PDGF-R) analogs may, for example, comprise a portion of a PDGF receptor capable of binding anti-PDGF receptor antibodies, PDGF, PDGF isoforms, PDGF analogs, or PDGF antagonists.

Dimerizing Protein

A polypeptide chain having affinity for a second polypeptide chain, such that the two chains associate under physiological conditions to form a dimer. The second polypeptide chain may be the same or a different chain.

Biological Activity

A function or set of activities performed by a molecule in a biological context (i.e., in an organism or an in vitro facsimile thereof). biological activities may include the induction of extracellular matrix secretion from responsive cell lines, the induction of hormone secretion, the induction of chemotaxis, the induction of mitogenesis, the induction of differentiation, or the inhibition of cell division of responsive cells. A recombinant protein or peptide is considered to be biologically active if it exhibits one or more biological activities of its native counterpart.

Ligand

A molecule capable of being bound by the ligand-binding domain of a receptor or by a receptor analog. The molecule may be chemically synthesized or may occur in nature. Ligands may be grouped into agonists and antagonists. Agonists are those molecules whose binding to a receptor induces the response pathway within a cell. Antagonists are those molecules whose binding to a receptor blocks the response pathway within a cell.

Joined

Two or more DNA coding sequences are said to be joined when, as a result of in-frame fusions between the DNA coding sequences or as a result of the removal of intervening sequences by normal cellular processing, the DNA coding sequences are translated into a polypeptide fusion.

As noted above, the present invention provides methods for producing biologically active dimerized polypeptide fusions and secreted receptor analogs, which include, for example, PDGF receptor analogs. Secreted receptor analogs may be used to screen for new compounds that act as agonists or antagonists when interacting with cells containing membrane-bound receptors. In addition, the methods of the present invention provide dimerized non-immunoglobulin polypeptide fusions of therapeutic value that are biologically active only as diners. Moreover, the present invention provides methods of producing polypeptide dimers that are biologically active only as non-covalently associated diners. Secreted, biologically active dimers that may be produced using the resent invention include nerve growth factor, colony stimulating factor-1, factor XIII, and transforming growth factor β.

As used herein, the ligand-binding domain of a receptor is that portion of the receptor that is involved with binding the natural ligand. While not wishing to be bound by theory, the binding of a natural ligand to a receptor is believed to induce a conformational change which elicits a response to the change within the response pathway of the cell. For membrane-bound receptors, the ligand-binding domain is generally believed to comprise the extracellular domain for the receptor. The structure of receptors may be predicted from the primary translation products using the hydrophobicity plot function of, for example, P/C Gene or Intelligenetics Suite (Intelligenetics, Mt. View, Calif.) or may be predicted according to the methods described, for example, by Kyte and Doolittle, *J. Mol. Biol.* 157:105–132, 1982). The ligand-binding domain of the PDGF β-receptor, for example, has been predicted to include amino acids 29–531 of the published sequence (Gronwald et al., ibid.). The ligand-binding domain of the PDGF α-receptor has been predicted to include amino acids 25–500 of the published α-receptor sequence (Matsui et al., ibid.). As used herein, the ligand-binding domain of the PDGF β-receptor includes amino acids 29–441 of the sequence of FIGS. 1A–1D (Sequence ID Number 1) and C-terminal extensions up to and including amino acid 531 (FIG. 1B). The ligand-binding domain of the PDGF α-receptor is understood to include amino acids 24–524 of FIGS. 11A & 11B (Sequence ID Numbers 35 and 36).

Receptor analogs that may be used in the present invention include the ligand-binding domains of the epidermal growth factor receptor (EGF-R) and the insulin receptor. As used herein, a ligand-binding domain is that portion of the receptor that is involved in binding ligand and is generally a portion or essentially all of the extracellular domain that extends from the plasma membrane into the extracellular space. The ligand-binding domain of the EGF-R, for example, resides in the extracellular domain. EGF-R diners have been found to exhibit higher ligand-binding affinity than EGF-R monomers (Boni-Schnetzler and Pilch, *Proc. Natl. Acad. Sci. USA §A:*7832–7836, 1987). The insulin receptor (Ullrich et al., *Nature* 313:756–761, 1985) requires dimerization for biological activity.

Another example of a receptor that may be secreted from a host cell is a platelet-derived growth factor receptor (PDGF-R). Two classes of PDGF-Rs, which recognized different isoforms of PDGF, have been identified. (PDGF is a disulfide-bonded, two-chain molecule, which is made up of an A chain and a B chain. These chains may be combined as AB heterodimers, AA homodimers or BB homodimers. These dimeric molecules are referred to herein as "isoforms".) The β-receptor (PDGFβ-R), which recognizes only the BB isoform of PDGF (PDGF-BB), has been described (Claesson-Welsh et al., *Mol. Cell, Biol.* 8:3476–3486, 1988; Gronwald et al., *Proc. Natl. Acad. Sci. USA* 85:3435–3439, 1988). The α-receptor (PDGFα-R), which recognizes all three PDGF isoforms (PDGF-AA, PDGF-AB and PDGF-BB), has been described by Matsui et al. (*Science* 243:800–804, 1989) and Kelly and Murray (pending commonly assigned U.S. patent application Ser. No. 07/355,018, which is incorporated herein by reference). The primary translation products of these receptors indicate that each includes an extracellular domain implicated in the ligand-binding process, a transmembrane domain, and a cytoplasmic domain containing a tyrosine kinase activity.

The present invention provides a standardized assay system, not previously available in the art, for determining the presence of PDGF, PDGF isoforms, PDGF agonists or PDGF antagonists using a secreted PDGF receptor analogs. Such an assay system will typically involve combining the secreted PDGF receptor analog with a biological sample under physiological conditions which permit the formation of receptor-ligand complexes, followed by detecting the presence of the receptor-ligand complexes. The term physiological conditions is meant to include those conditions found within the host organism and include, for example, the conditions of osmolarity, salinity and pH. Detection may be achieved through the use of a label attached to the PDGF receptor analog or through the use of a labeled antibody which is reactive with the receptor analog or the ligand. A wide variety of labels may be utilized, such as radionuclides, fluorophores, enzymes and luminescers. Receptor-ligand complexes may also be detected visually, i.e., in immunoprecipitation assays which do not require the use of a label. This assay system provides secreted PDGF receptor analogs that may be utilized in a variety of screening assays for, for example, screening for analogs of PDGF. The present invention also provides a methods for measuring the level of PDGF and PDGF isoforms in biological fluids.

As noted above, the present invention provides methods for producing dimerized polypeptide fusions that require dimerization for biological activity or enhancement of biological activity. Polypeptides requiring dimerization for biological activity include, in addition to certain receptors, nerve growth factor, colony-stimulating factor-1 (CSF-1), transforming growth factor β (TGF-β), PDGF, and factor XIII. Nerve growth factor is a non-covalently linked diner (Harper et al., *J. Biol. Chem.* 257: 8541–8548, 1982). CSF-1, which specifically stimulates the proliferation and differentiation of cells of mononuclear phagocytic lineage, is a disulfide-bonded homodimer (Retternmier et al., *Mol. Cell. Biol.* 7: 2378–2387, 1987). TGF-β is biologically active as a disulfide-bonded dimer (Assoian et al., *J. Biol. Chem.* 258: 7155–7160, 1983). Factor XIII is a plasma protein that exists as a two chain homodimer n its activated form (Ichinose et al., *Biochem.* 25: 6900– 6906, 1986). PDGF, as noted above, is a disulfide-bonded, two chain molecule (Murray et al., U.S. Pat. No. 4,766,073).

The present invention provides methods by which receptor analogs, including receptor analogs and PDGF-R analogs, requiring dimerization for activity may be secreted from host cells. The methods described herein are particularly advantageous in that they allow the production of large quantities of purified receptors. The receptors may be used in assays for the screening of potential ligands, in assays for binding studies, as imaging agents, and as agonists and antagonists within therapeutic agents.

A DNA sequence encoding a human PDGF receptor may be isolated as a cDNA using techniques known in the art (see, for example, Okayama and Berg, *Mol. Cell. Biol.* 2:161–170, 1982; *Mol. Cell. Biol.* 3: 280–289, 1983) from a library of human genomic or cDNA sequences. Such libraries may be prepared by standard procedures, such as those disclosed by Gubler and Hoffman (*Gene* 25: 263–269, 1983). It is preferred that the molecule is a CDNA molecule because CDNA lack introns and are therefore more suited to manipulation and expression in transfected or transformed cells. Sources of mRNA for use in the preparation of a CDNA library include the MG-63 human osteosarcoma cell line (available from ATCC under accession number CRL 1427), diploid human dermal fibroblasts and human embryo fibroblast and brain cells (Matsui et al., ibid.). A CDNA encoding a PDGFβ-R has been cloned from a diploid human dermal fibroblast cDNA library using oligonucleotide probes complementary to sequences of the mouse PDGF receptor (Gronwald et al., ibid.). A PDGFα-R cDNA has been isolated by Matsui et al. (ibid.) from human embryo fibroblast and brain cells. Alternatively, a cDNA encoding a PDGFα-R may be isolated from a library prepared from MG-63 human osteosarcoma cells using a cDNA probe containing sequences encoding the transmembrane and cytoplasmic domains of the PDGFβ-R (described by Kelly and Murray, ibid.). Partial CDNA clones (fragments) can be extended by re-screening of the library with the cloned CDNA fragment until the full sequence is obtained. In one embodiment, a ligand-binding domain of a PDGF receptor is encoded by the sequence of FIGS. 1A & 1B (Sequence ID Number 1) from amino acid 29 through amino acid 441. In another embodiment, a ligand-binding domain of a PDGF receptor is encoded by the sequence of FIGS. 1A & 1B (Sequence ID Number 1) from amino acid 29 through amino acid 531. In yet another embodiment, a ligand-binding domain of a PDGF receptor is encoded by the sequence of FIGS. 11A & 11B (Sequence ID Numbers 35 and 36) from amino acid 24 through amino acid 524. One skilled in the art may envision the use of a smaller DNA sequence encoding the ligand-binding domain of a PDGF receptor containing at least 400 amino acids of the extracellular domain.

DNA sequences encoding EGF-R (Ullrich et al., *Nature* 3: 418–425, 1984), the insulin receptor (Ullrich et al., *Nature* 313: 756–761, 1985), nerve growth factor (Ullrich et al. *Nature* 303: 821–825, 1983), colony stimulating factor-1 (Rettenmier et al., ibid.), transforming growth factor β (Derynck et al., *Nature* 3: 701–705, 1985), PDGF (Murray et al., ibid.), and factor XIII (Ichinose et al., ibid.) may also be used within the present invention.

To direct polypeptides requiring dimerization for biological activity or receptor analogs into the secretory pathway of the host cell, at least one secretory signal sequence is used in conjunction with the DNA sequence of interest. Preferred secretory signals include the alpha factor signal sequence (pre-pro sequence) (Kurjan and Herkowitz, *Cell* 30: 933–943, 1982; Kurjan et al., U.S. Pat. No. 4,546,082;

Brake, EP 116,201, 1983), the PHO5 signal sequence (Beck et al., WO 86/00637), the BAR1 secretory signal sequence (MacKay et al., U.S. Pat. No. 4,613,572; MacKay, WO 87/002670), immunoglobulin $V_H$ signal sequences (Loh et al., *Cell* 33: 85–93, 1983; Watson *Nuc, Acids, Res.* 12: 5145–5164, 1984) and immunoglobulin $V_\kappa$ signal sequences (Watson, ibid.). Particularly preferred signal sequences are the SUC2 signal sequence (Carlson et al., *Mol. Cell. Biol.* 3: 439–447, 1983) and PDGF receptor signal sequences. Alternatively, secretory signal sequences may be synthesized according to the rules established, for example, by von Heinje (*Eur. J. Biochem.* 133: 17–21, 1983; *J. Mol. Biol,* 184: 99–105, 1985; *Nuc. Acids. Res.* 14: 4683–3690, 1986).

Secretory signal sequences may be used singly or may be combined. For example, a first secretory signal sequence may be used singly or combined with a sequence encoding the third domain of Barrier (described in co-pending commonly assigned U.S. patent application Ser. No. 07/104,316, which is incorporated by reference herein in its entirety). The third domain of Barrier may be positioned in proper reading frame 3' of the DNA sequence of interest or 5' to the DNA sequence and in proper reading frame with both the secretory signal sequence and the DNA sequence of interest.

In one embodiment of the present invention, a sequence encoding a dimerizing protein is joined to a sequence encoding a polypeptide chain of a polypeptide dimer or a receptor analog, and this fused sequence is joined in proper reading frame to a secretory signal sequence. As shown herein, the present invention utilizes such an arrangement to drive the association of the polypeptide or receptor analog to form a biologically active molecule upon secretion. Suitable dimerizing proteins include the *S. cerevisiae* repressible acid phosphatase (Mizunaga et al., *J. Biochem.* (Tokyo) 103: 321–326, 1988), the *S. cerevisiae* type 1 killer preprotoxin (Sturley et al., *EMBO J.* 5: 3381–3390, 1986), the *S. calsbergensis* alpha galactosidase melibiase (Sumner-Smith et al., *Gene* 36: 333–340, 1985), the *S. cerevisiae* invertase (Carlson et al., *Mol. Cell. Biol.* 3: 39–447, 1983), the *Neurospora crassa* ornithine decarboxylase (Digangi et al., *J. Biol. Chem.* 6: 7889–7893, 1987), immunoglobulin heavy chain hinge regions (Takahashi et al., *Cell* 29: 671–679, 1982), and other dimerizing immunoglobulin sequences. In a preferred embodiment, *S. cerevisiae* invertase is used to drive the association of polypeptides into dimers. Portions of dimerizing proteins, such as those mentioned above, may be used as dimerizing proteins where those portions are capable of associating as a dimer in a covalent or noncovlent manner. Such portions may be determined by, for example, altering a sequence encoding a dimerizing protein through In vitro mutagenesis to delete portions of the coding sequence. These deletion mutants may be expressed in the appropriate host to determine which portions retain the capability of associating as dimers. Portions of immunoglobulin gene sequences may be used to drive the association of non-immunoglobulin polypeptides. These portions correspond to discrete domains of immunoglobulins. Immunoglobulins comprise variable and constant regions, which in turn comprise discrete domains that show similarity in their three-dimensional conformations. These discrete domains correspond to immunoglobulin heavy chain constant region domain exons, immunoglobulin heavy chain variable region domain exons, immunoglobulin light chain varable region domain exons and immunoglobulin light chain constant region domain exons in immunoglobulin genes (Hood et al., in *Immunology,* The Benjamin/Cummings Publishing Company, Inc., Menlo Park, Calif.; Honjo et al., *Cell* 18: 559–568, 1979; Takahashi et al., *Cell* 29: 671–679, 1982; and Honjo, *Ann. Rev. Immun.* 1:499–528, 1983)). Particularly preferred portions of immunoglobulin heavy chains include Fab and Fab' fragments. (An Fab fragment is a portion of an immunoglobulin heavy chain that includes a heavy chain variable region domain and a heavy chain constant region omain. An Fab' fragment is a portion of an mmunoglobulin heavy chain that includes a heavy chain variable region domain, a heavy chain constant region domain and a heavy chain hinge region domain.)

It is preferred to use an immunoglobulin light chain constant region in association with at least one immunoglobulin heavy chain constant region domain. In a another embodiment, an immunoglobulin light chain constant region is associated with at least one immunoglobulin heavy chain constant region domain joined to an immunoglobulin hinge region. In one set of embodiments, an immunoglobulin light chain constant region joined in frame with a polypeptide chain of a non-immunoglobulin polypeptide dimer or receptor analog and is associated with at least one heavy chain constant region. In a preferred set of embodiments a variable region is joined upstream of and in proper reading frame with at least one immunoglobulin heavy chain constant region. In another set of embodiments, an immunoglobulin heavy chain is joined in frame with a polypeptide chain of a non-immunoglobulin polypeptide dimer or receptor analog and is associated with an immunoglobulin light chain constant region. In yet another set of embodiments, a polypeptide chain of a non-immunoglobulin polypeptide dimer or receptor analog is joined to at least one immunoglobulin heavy chain constant region which is joined to an immunoglobulin hinge region and is associated with an immunoglobulin light chain constant region. In a preferred set of embodiments an immunoglobulin variable region is joined upstream of and in proper reading frame with the immunoglobulin light chain constant region.

Immunoglobulin heavy chain constant region domains include $C_H1$, $C_H2$, $C_H3$, and $C_H4$ of any class of immunoglobulin heavy chain including γ, α, ε, μ, and δ classes (Honjo, ibid., 1983) A particularly preferred immunoglobulin heavy chain constant region domain is human $C_H1$. Immunoglobulin variable regions include $V_H$, $V_\kappa$, or $V_\lambda$.

DNA sequences encoding immunoglobulins may be cloned from a variety of genomic or CDNA libraries known in the art. The techniques for isolating such DNA sequences using probe-based methods are conventional techniques and are well known to those skilled in the art. Probes for isolating such DNA sequences may be based on published DNA sequences (see, for example, Hieter et al., *Cell* 2: 197–207, 1980). Alternatively, the polymerase chain reaction (PCR) method disclosed by Mullis et al. (U.S. Pat. No. 4,683,195) and Mullis (U.S. Pat. No. 4,683,202), incorporated herein by reference may be used. The choice of library and selection of probes for the isolation of such DNA sequences is within the level of ordinary skill in the art.

Host cells for use in practicing the present invention include eukaryotic cells capable of being transformed or transfected with exogenous DNA and grown in culture, such as cultured mammalian and fungal cells. Fungal cells, including species of yeast (e.g., Saccharomyces spp., Schizosaccharomyces spp.), or filamentous fungi (e.g., Aspergillus spp., Neurospora spp.) may be used as host cells within the present invention. Strains of the yeast *Saccharomyces cerevisiae* are particularly preferred.

Expression units for use in the present invention will generally comprise the following elements, operably linked in a 5' to 3' orientation: a transcriptional promoter, a secretory signal sequence a DNA sequence encoding nonimmunoglobulin polypeptide requiring dimerization for biological activity joined to a dimerizing protein and a transcriptional terminator. The selection of suitable promoters, signal sequences and terminators will be determined by the selected host cell and will be evident to one skilled in the art and are discussed more specifically below.

Suitable yeast vectors for use in the present invention include YRp7 (Struhl et al., *Proc. Natl. Acad. Sci. USA* 7: 1035–1039, 1978), YEp13 (Broach et al., *Gene* 8: 121–133, 1979), pJDB249 and pJDB219 (Beggs, *Nature* 275:104–108, 1978) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al. ibid.), URA3 (Botstein et al., *Gene p:* 17, 1979), HIS3 (Struhl et al., ibid.) or POT1 (Kawasaki and Bell, EP 171,142). Other suitable selectable markers include the CAT gene, which confers chloramphenicol resistance on yeast cells.

Preferred promoters for use in yeast include promoters from yeast glycolytic genes (Hitzeman et al., *J. Biol. Chem.* 255: 12073–12080, 1980; Alber and Kawasaki, *J. Mol. A Genet.* 1: 419–434, 1982; Kawasaki, U.S. Pat. No. 4,599, 311) or alcohol dehydrogenase genes (Young et al., in *Genetic Engineering of Microorganisms for Chemicals*, Hollaender et al., (eds.), p. 355, Plenum, New York, 1982; Ammerer, *Meth. Enzymol.* 101: 192–201, 1983). In this regard, particularly preferred promoters are the TPI1 promoter (Kawasaki, U.S. Pat. No. 4,599,311, 1986) and the ADH2-4$^c$ promoter (Russell et al., *Nature* 304: 652–654, 1983 and Irani and Kilgore, described in pending, commonly assigned U.S. patent application Ser. No. 07/183,130, which is incorporated herein by reference). The expression units may also include a transcriptional terminator. A preferred transcriptional terminator is the TPI1 terminator (Alber and Kawasaki, ibid.).

In addition to yeast, proteins of the present invention can be expressed in filamentous fungi, for example, strains of the fungi Aspercillus (McKnight and Upshall, described in commonly assigned U.S. Pat. No. 4,935,349, which is incorporated herein by reference). Examples of useful promoters include those derived from *Aspergillus nidulans* glycolytic genes, such as the ADH3 promoter (McKnight et al., *EMBO J.* 4: 2093–2099, 1985) and the tpiA promoter. An example of a suitable terminator is the ADH3 terminator (McKnight et al., ibid.). The expression units utilizing such components are cloned into vectors that are capable of insertion into the chromosomal DNA of Aspergillus.

Techniques for transforming fungi are well known in the literature, and have been described, for instance, by Beggs (ibid.), Hinnen et al. (*Proc. Natl. Acad. Sci. USA* 75: 1929–1933, 1978), Yelton et al., (*Proc. Natl. Acad. Sci. USA* 81: 1740–1747, 1984), and Russell (*Nature* 301: 167–169, 1983). The genotype of the host cell will generally contain a genetic defect that is complemented by the selectable marker present on the expression vector. Choice of a particular host and selectable marker is well within the level of ordinary skill in the art.

In a preferred embodiment, a *Saccharomyces cerevisiae* host cell that contains a genetic deficiency in a gene required for asparagine-linked glycosylation of glycoproteins is used. Preferably, the *S. cerevisiae* host cell contains a genetic deficiency in the MNN9 gene (described in pending, commonly assigned U.S. patent application Ser. Nos. 116,095 and 189,547 which are incorporated by reference herein in their entirety). Most preferably, the *S. cerevisiae* host cell contains a disruption of the MNN9 gene. *S. cerevisiae* host cells having such defects may be prepared using standard techniques of mutation and selection. Ballou et al. (*J. Biol. Chem.* 255: 5986–5991, 1980) have described the isolation of mannoprotein biosynthesis mutants that are defective in genes which affect asparagine-linked glycosylation. Briefly, mutagenized *S. cerevisiae* cells were screened using fluoresceinated antibodies directed against the outer mannose chains present on wild-type yeast. Mutant cells that did not bind antibody were further characterized and were found to be defective in the addition of asparagine-linked oligosaccharide moieties. To optimize production of the heterologous proteins, it is preferred that the host strain carries a mutation, such as the S. cerevisiae pep4 mutation (Jones, *Genetics* 85: 23–33, 1977), which results in reduced proteolytic activity.

In addition to fungal cells, cultured mammalian cells may be used as host cells within the present invention. Preferred cell lines are rodent myeloma cell lines, which include p3X63Ag8 (ATCC TIB 9), OF (ATCC CRL 1646), NS-1 (ATCC TIB 18) and 210-RCY-Agl (Galfre et al., *Nature* 277: 131, 1979). A particularly preferred rodent rmyeloma cell line is SP2/0-Ag14 (ATCC CRL 1581). In addition, a number of other cell lines may be used within the present invention, including COS-1 (ATCC CRL 1650), BHK, p363.Ag.8.653 (ATCC CRL 1580) Rat Hep I (ATCC CRL 1600), Rat Hep II (ATCC CRL 1548), TCMK (ATCC CCL 139), Human lung (ATCC CCL 75.1), Human hepatoma (ATCC HTB-52), Hep G2 (ATCC HB 8065), Mouse liver (ATCC CC 29.1), 293 (ATCC CRL 1573; Graham et al., *J. Gen. Virol.* 36: 59–72, 1977) and DUKX cells (Urlaub and Chasin, *Proc. Patl. Acad. Sci USA* 77: 4216–4220, 1980) A preferred BHK cell line is the tk$^-$ts13 BHK cell line (Waechter and Baserga, *Proc. Natl. Acad. Sci USA* 79: 1106–1110, 1982). A preferred BHK cell line is the tk-ts13 BHK cell line (Waechter and Baserga, *Proc. Natl. Acad. Sci. USA* 79: 1106–1110, 1982). A tk$^-$ BHK cell line is available from the American Type Culture Collection, Rockville, Md., under accession number CRL 1632. A particularly preferred tk$^-$ BHK cell line is BHK 570 which is available from the American Type Culture Collection under accession number 10314.

Mammalian expression vectors for use in carrying out the present invention will include a promoter capable of directing the transcription of a cloned gene or cDNA. referred promoters include viral promoters and cellular promoters. Preferred viral promoters include the major late promoter from adenovirus 2 (Kaufman and Sharp, *Mol. Cell. Biol.* 2: 1304–13199, 1982) and the SV40 promoter (Subramani et al., *Mol. Cell. Biol,* 1: 854–864, 1981). Preferred cellular promoters include the mouse metallothionein 1 promoter (Palmiter et al., *Science* 222: 809–814, 1983) and a mouse $V_\kappa$ promoter (Grant et al., *Nuc. Acids Res.* 11: 5496, 1987). A particularly preferred promoter is a mouse $V_H$ promoter (Loh et al., ibid.). Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the adenovirus 5 E1B region and the human growth hormone gene terminator (DeNoto et al., *Nuc. Acids Res.* 2: 3719–3730, 1981). A particularly preferred polyadenylation signal is the $V_H$ gene terminator (Loh et al., ibid.). The expression vectors may include a noncoding viral leader sequence, such as the adenovirus 2 tripartite leader, located between the promoter and the RNA splice sites. Preferred vectors may also include enhancer sequences, such as the SV40 enhancer and the mouse $\mu$ enhancer (Gillies, *Cell* 33: 717–728, 1983). Expression vectors may also include sequences encoding the adenovirus VA RNAs.

Cloned DNA sequences may be introduced into cultured mammalian cells by, for example, calcium phosphate-mediated transfection (Wigler et al., *Cell* 14: 725, 1978; Corsaro and Pearson, *Somatic Cell Genetics* 7: 603, 1981; Graham and Van der Eb, *Virology* 52: 456, 1973.) Other techniques for introducing cloned DNA sequences into mammalian cells, such as electroporation (Neumann et al., *EMBO J.* 1: 841–845, 1982), may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. A preferred amplifiable selectable marker is the DHFR gene. A particularly preferred amplifiable marker is the DHFR$^r$ CDNA (Simonsen and Levinson, *Proc. Natl. Adac. Sci. USA* 80: 2495–2499, 1983). Selectable markers are reviewed by Thilly (*Mammalian Cell Technology*, Butterworth Publishers, Stoneham, Mass.) and the choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA" to the mixture which is introduced into the cells.

Transfected mammalian cells are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

Host cells containing DNA constructs of the resent invention are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals and growth factors. The growth medium will generally select for cells containing the DNA construct by, for example, drug selection or deficiency in an essential nutrient which are complemented by the selectable marker on the DNA construct or co-transfected with the DNA construct. Yeast cells, for example, are preferably grown in a chemically defined medium, comprising a non-amino acid nitrogen source, inorganic salts, vitamins and essential amino acid supplements. The pH of the medium is preferably maintained at a pH greater than 2 and less than 8, preferably at pH 6.5. Methods for maintaining a stable pH include buffering and constant pH control, preferably through the addition of sodium hydroxide. Preferred buffering agents include succinic acid and Bis-Tris (Sigma Chemical Co., St. Louis, Mo.). Yeast cells having a defect in a gene required for asparagine-linked glycosylation are preferably grown in a medium containing an osmotic stabilizer. A preferred osmotic stabilizer is sorbitol supplemented into the medium at a concentration between 0.1 M and 1.5 M., preferably at 0.5 M or 1.0 M. Cultured mammalian cells are generally grown in commercially available serum-containing or serum-free media. Selection of a medium appropriate for the particular cell line used is within the level of ordinary skill in the art.

The culture medium from appropriately grown transformed or transfected host cells is separated from the cell material, and the presence of dimerized polypeptide fusions or secreted receptor analogs is demonstrated. A preferred method of detecting receptor analogs, for example, is by the binding of the receptors or portions of receptors to a receptor-specific antibody. An anti-receptor antibody may be a monoclonal or polyclonal antibody raised against the receptor in question, for example, an anti-PDGF receptor monoclonal antibody may be used to assay for the presence of PDGF receptor analogs. Another antibody, which may be used for detecting substance P-tagged peptides and proteins, is a commercially available rat anti-substance P monoclonal antibody which may be utilized to visualize peptides or proteins that are fused to the C-terminal amino acids of substance P. Ligand binding assays may also be used to detect the presence of receptor analogs. In the case of PDGF receptor analogs, it is preferable to use fetal foreskin fibroblasts, which express PDGF receptors, to compete against the PDGF receptor analogs of the present invention for labeled PDGF and PDGF isoforms.

Assays for detection of secreted, biologically active peptide dimers and receptor analogs may include Western transfer, protein blot or colony filter. A Western transfer filter may be prepared using the method described by Towbin et al. (*Proc. Hatl. Acad. Sci. USA* 76: 4350–4354, 1979). Briefly, samples are electrophoresed in a sodium dodecyl-sulfate polyacrylamide gel. The proteins in the gel are electrophoretically transferred to nitrocellulose paper. Protein blot filters may be prepared by filtering supernatant samples or concentrates through nitrocellulose filters using, for example, a Minifold (Schleicher & Schuell, Keene, N.H.). Colony filters may be prepared by growing colonies on a nitrocellulose filter that has been laid across an appropriate growth medium. In this method, a solid medium is preferred. The cells are allowed to grow on the filters for at least 12 hours. The cells are removed from the filters by washing with an appropriate buffer that does not remove the proteins bound to the filters. A preferred buffer comprises 25 mM Tris-base, 19 mM glycine, pH 8.3, 20% methanol.

The dimerized polypeptide fusions and receptor analogs present on the Western transfer, protein blot or colony filters may be visualized by specific antibody binding using methods known in the art. For example, Towbin et al. (ibid.) describe the visualization of proteins immobilized on nitrocellulose filters with a specific antibody followed by a labeled second antibody, directed against the first antibody. Kits and reagents required for visualization are commercially available, for example, from Vector Laboratories, (Burlingame, Calif.), and Sigma Chemical Company (St. Louis, Mo.).

Secreted, biologically active dimerized polypeptide fusions and receptor analogs may be isolated from the medium of host cells grown under conditions that allow the secretion of the biologically active dimerized polypeptide fusions and receptor analogs. The cell material is removed from the culture medium, and the biologically active dimerized polypeptide fusions and receptor analogs are isolated using isolation techniques known in the art. Suitable isolation techniques include precipitation and fractionation by a variety of chromatographic methods, including gel filtration, ion exchange chromatography and immunoaffinity chromatography. A particularly preferred purification method is immunoaffinity chromatography using an antibody directed against the receptor analog or dimerized polypeptide fusion. The antibody is preferably immobilized or attached to a solid support or substrate. A particularly preferred substrate is CNBr-activated Sepharose (Pharmacia LKB Technologies, Inc., Piscataway, N.J.). By this method, the medium is combined with the antibody/substrate under conditions that will allow binding to occur. The complex may be washed to remove unbound material, and the receptor analog or peptide dimer is released or eluted through the use of conditions unfavorable to complex formation. Particularly useful methods of elution include changes in pH, wherein the immobilized antibody has a high affinity for the ligand at a first pH and a reduced affinity at a second (higher or lower) pH; changes in concentration of certain chaotropic agents; or through the use of detergents.

The secreted PDGF receptor analogs of the present invention can be used within a variety of assays for detecting the presence of and/or screening for native PDGF, PDGF isoforms or PDGF-like molecules. These assays will typically involve combining PDGF receptor analogs, which may be bound to a solid substrate such as polymeric microtiter plate wells, with a biological sample under conditions that permit the formation of receptor/ligand complexes. Screening assays for the detection of PDGF, PDGF isoforms or PDGF-like molecules will typically involve combining soluble PDGF receptor analogs with a biological sample and incubating the mixture with a PDGF isoform or mixture of PDGF isoforms bound to a solid substrate such as polymeric microtiter plates, under conditions that permit the formation of receptor/ligand complexes. Detection may be achieved through the use of a label attached to the receptor or through the use of a labeled antibody which is reactive with the receptor. Alternatively, the labeled antibody may be reactive with the ligand. A wide variety of labels may be utilized, such as radionuclides, fluorophores, enzymes and luminescers. Complexes may also be detected visually, i.e., in immunoprecipitation assays, which do not require the use of a label.

Secreted PDGF receptor analogs of the present invention may also be labeled with a radioisotope or other imaging agent and used for in vivo diagnostic purposes. Preferred radioisotope imaging agents include iodine-125 and technetium-99, with technetium-99 being particularly preferred. Methods for producing protein-isotope conjugates are well known in the art, and are described by, for example, Eckelman et al. (U.S. Pat. No. 4,652,440), Parker et al. (WO 87/05030) and Wilber et al. (EP 203,764). Alternatively, the secreted receptor analogs may be bound to spin label enhancers and used for magnetic resonance (MR) imaging. Suitable spin label enhancers include stable, sterically hindered, free radical compounds such as nitroxides. Methods for labeling ligands for MR imaging are disclosed by, for example, Coffman et al. (U.S. Pat. No. 4,656,026). For administration, the labeled receptor analogs are combined with a pharmaceutically acceptable carrier or diluent, suchEs sterile saline or sterile water. Administration is preferably by bolus injection, preferably intravenously. These imaging agents are particularly useful in identifying the locations of atherosclerotic plaques, PDGF-producing tumors, and receptor-bound PDGF.

The secreted PDGF receptor analogs of the present invention may also be utilized within diagnostic kits. Briefly, the subject receptor analogs are preferably provided in a lyophilized form or immobilized onto the walls of a suitable container, either alone or in conjunction with antibodies capable of binding to native PDGF or selected PDGF isoform(s) or specific ligands. The antibodies, which may be conjugated to a label or unconjugated, are generally included in the kits with suitable buffers, such as phosphate, stabilizers, inert proteins or the like. Generally, these materials are present in less than about 5% weight based upon the amount of active receptor analog, and are usually present in an amount of at least about 0.001% weight. It may also be desirable to include an inert excipient to dilute the active ingredients. Such an excipient may be present from about 1% to 99% weight of the total composition. In addition, the kits will typically include other standard reagents, instructions and, depending upon the nature of the label involved, reactants that are required to produce a detectable product. Where an antibody capable of binding to the receptor or receptor/ligand complex is employed, this antibody will usually be provided in a separate vial. The antibody is typically conjugated to a label and formulated in an analogous manner with the formulations briefly described above. The diagnostic kits, including the containers, may be produced and packaged using conventional kit manufacturing procedures.

As noted above, the secreted PDGF receptor analogs of the present invention may be utilized within methods for purifying PDGF from a variety of samples. Within a preferred method, the secreted PDGF receptor analogs are immobilized or attached to a substrate or support material, such as polymeric tubes, beads, polysaccharide particulates, polysaccharide-containing materials, polyacrylamide or other water insoluble polymeric materials. Methods for immobilization are well known in the art (Mosbach et al., U.S. Pat. No. 4,415,665; Clarke et al., *Meth. Enzymology*: 436–442, 1979). A common method of immobilization is CNBr activation. Activated substrates are commercially available from a number of suppliers, including Pharmacia (Piscataway, N.J.), Pierce chemical Co. (Rockford, Ill.) and Bio-Rad Laboratories (Richmond, Calif.). A preferred substrate is CNBr-activated Sepharose (Pharmacia, Piscataway, N.J.). Generally, the substrate/receptor analog complex will be in the form of a column. The sample is then combined with the immobilized receptor analog under conditions that allow binding to occur. The substrate with immobilized receptor analog is first equilibrated with a buffer solution of a composition in which the receptor analog has been previously found to bind its ligand. The sample, in the solution used for equilibration, is then applied to the substrate/receptor analog complex. Where the complex is in the form of a column, it is preferred that the sample be passed over the column two or more times to permit full binding of ligand to receptor analog. The complex is then washed with the same solution to elute unbound material. In addition, a second wash solution may be used to minimize nonspecific binding. The bound material may then be released or eluted through the use of conditions unfavorable to complex formation. Particularly useful methods include changes in pH, wherein the immobilized receptor has a high affinity for PDGF at a first pH and reduced affinity at a second (higher or lower) pH; changes in concentration of certain chaotropic agents; or through the use of detergents.

The secreted PDGF receptor analogs fused to dimerizing proteins of the present invention may be used in pharmaceutical compositions for topical or intravenous application. The secreted PDGF receptor analogs of the present invention may be useful in the treatment of atherosclerosis by, for example, binding endogenous PDGF to prevent smooth muscle cell proliferation. The PDGF receptor analogs fused to dimerizing proteins are used in combination with a physiologically acceptable carrier or diluent. Preferred carriers and diluents include saline and sterile water. Pharmaceutical compositions may also contain stabilizers and adjuvants. The resulting aqueous solutions may be packaged for use or filtered under aseptic conditions and lyophilized, the lyophilized preparation being combined with a sterile aqueous solution prior to administration.

The following examples are offered by way of illustration and not by way of limitation.

EXAMPLES

Enzymes, including restriction enzymes, DNA polymerase I (Klenow fragment), T4 DNA polymerase, T4 DNA ligase and T4 polynucleotide kinase, were obtained from New England Biolabs (Beverly, Mass.), GIBCO-BRL (Gaithersburg, Md.) and Boerhinger-Mannheim Biochemicals (Indianapolis, Ind.) and were used as directed by the manufacturer or as described in Maniatis et al. (*Molecular Cloning: A Laboratory Manual,* Cold Spring Harbor Laboratory, NY, 1982) and Sambrook et al. (*Molecular Cloning: A Laboratory Manual*/Second Edition, Cold Spring Harbor Laboratory, NY, 1989).

Example 1

Cloning PDGF Receptor cDNAs

A. Cloning the PDGF β-Receptor

A cDNA encoding the PDGF β-receptor was cloned as follows. Complementary DNA (cDNA) libraries were prepared from poly(A) RNA from diploid human dermal fibroblast cells, prepared by explant from a normal adult, essentially as described by Hagen et al. (*Proc, Natl. Acad. Sci. USA* 83: 2412–2416, 1986). Briefly, the poly(A) RNA was primed with oligo d(T) and cloned into λgt11 using Eco RI linkers. The random primed library was screened for the presence of human PDGF receptor cDNA's using three oligonucleotide probes complementary to sequences of the mouse PDGF receptor (Yarden et al., *Nature* 323: 226–232, 1986). Approximately one million phage from the random primed human fibroblast cell library were screened using oligonucleotides ZC904, ZC905 and ZC906 (Table 1; Sequence ID Numbers 5, 6 and 7, respectively). Eight positive clones were identified and plaque purified. Two clones, designated RP41 and RP51, were selected for further analysis by restriction enzyme mapping and DNA sequence analysis. RP51 was found to contain 356 bp of 5'-noncoding sequence, the ATG translation initiation codon and 738 bp of the amino terminal coding sequence. RP41 was found to overlap clone RP51 and contained 2649 bp encoding amino acids 43–925 of the β-receptor protein.

TABLE 1

Oligonucleotide Sequences

ZC871 (Sequence ID Number 3)
5' CTC TCT TCC TCA GGT AAA TGA GTG CCA GGG CCG GCA AGC CCC CGC TCC 3'

ZC872 (Sequence ID Number 4)
5' CCG GGG AGC GGG GGC TTG CCG GCC CTG GCA CTC ATT TAC CTG AGG AAG AGA CAG CT 3'

ZC904 (Sequence ID Number 5)
5' CAT GGG CAC GTA ATC TAT AGA TTC ATC CTT GCT CAT ATC CAT GTA 3'

ZC905 (Sequence ID Number 6)
5' TCT TGC CAG GGC ACC TGG GAC ATC TGT TCC CAC ATC ACC GG 3'

ZC906 (Sequence ID Number 7)
5' AAG CTG TCC TCT GCT TCA GCC AGA GGT CCT GGG CAG CC 3'

ZC1380 (Sequence ID Number 8)
5' CAT GGT GGA ATT CCT GCT GAT 3'

ZC1447 (Sequence ID Number 9)
5' TG GTT GTG CAG AGC TGA GGA AGA GAT GGA 3'

ZC1453 (Sequence ID Number 10)
5' AAT TCA TTA TGT TGT TGC AAG CCT TCT TGT TCC TGC TAG CTG GTT TCG CTG TTA A 3'

ZC1454 (Sequence ID Number 11)
5' GAT CTT AAC AGC GAA ACC AGC TAG CAG GAA CAA GAA GGC TTG CAA CAA CAT AAT G 3'

ZC1478 (Sequence ID Number 12)
5' ATC GCG AGC ATG CAG ATC TGA 3'

ZC1479 (Sequence ID Number 13)
5' AGC TTC AGA TCT GCA TGC TGC CGA T 3'

ZC1776 (Sequence ID Number 14)
5' AGC TGA GCG CAA ATG TTG TGT CGA GTG CCC ACC GTG CCC AGC TTA GAA TTC T 3'

ZC1777 (Sequence ID Number 15)
5' CTA GAG AAT TCT AAG CTG GGC ACG GTG GGC ACT CGA CAC AAC ATT TGC GCT C 3'

ZC1846 (Sequence ID Number 16)
5' GAT CGG CCA CTG TCG GTG CGC TGC ACG CTG CGC AAC GCT GTG GGC CAG GAC ACG CAG GAG GTC ATC GTG GTG CCA CAC TCC TTG CCC TTT AAG CA 3'

ZC1847 (Sequence ID Number 17)
5' AGC TTG CTT AAA GGG CAA GGA GTG TGG CAC CAC GAT GAC CTC CTG CGT GTC CTG GCC CAC AGC GTT GCG CAG CGT GCA GCG CAC CGA CAG TGG CC 3'

ZC1886 (Sequence ID Number 18)
5' CCA GTG CCA AGC TTG TCT AGA CTT ACC TTT AAA GGG CAA GGA G 3'

ZC1892 (Sequence ID Number 19)
5' AGC TTG AGC GT 3'

ZC1893 (Sequence ID Number 20)
5' CTA GAC GCT CA 3'

ZC1894 (Sequence ID Number 21)
5' AGC TTC CAG TTC TTC GGC CTC ATG TCA GTT CTT CGG CCT CAT GTG AT 3'

ZC1895 (Sequence ID Number 22)
5' CTA GAT CAC ATG AGG CCG AAG AAC TGA CAT GAG GCC GAA GAA CTG GA 3'

ZC2181 (Sequence ID Number 23)

TABLE 1-continued

Oligonucleotide Sequences

5' AAT TCG GAT CCA CCA TGG GCA CCA GCC ACC CGG CGT
TCC TGG TGT TAG GCT GCC TGC TGA CCG GCC 3'

ZC2182 (Sequence ID Number 24)
5' TGA GCC TGA TCC TGT GCC AAC TGA GCC TGC CAT CGA
TCC TGC CAA ACG AGA ACG AGA AGG TTG TGC AGC TA 3'

ZC2183 (Sequence ID Number 25)
5' AAT TTA GCT GCA CAA CCT TCT CGT TCT CGT TTG GCA
GGA TCG ATG GCA GGC TCA GTT GGC ACA GGA TCA 3'

ZC2184 (Sequence ID Number 26)
5' GGC TCA GGC CGG TCA GCA GGC AGC CTA ACA CCA GGA
ACG CCG GGT GGC TGG TGC CCA TGG TGG ATC CG 3'

ZC2311 (Sequence ID Number 27)
5' TGA TCA CCA TGG CTC AAC TG 3'

ZC2351 (Sequence ID Number 28)
5' CGA ATT CCA C 3'

ZC2352 (Sequence ID Number 29)
5' CAT GGT GGA ATT CGA GCT 3'

ZC2392 (Sequence ID Number 30)
5' ACG TAA GCT TGT CTA GAC TTA CCT TCA GAA CGC AGG
GTG GG 3'

The 3'-end of the CDNA was not isolated in the first cloning and was subsequently isolated by screening 6×10⁵ phage of the oligo d(T)-primed CDNA library with a 630 bp Sst I-Eco RI fragment derived from the 3'-end of clone RP41. One isolate, designated TO91, was further analyzed by restriction enzyme mapping and DNA sequencing. This clone was found to comprise the 3'-end of the receptor coding region and 1986 bp of 3' untranslated sequence.

Clones RP51, RP41 and TO91 were ligated together to construct a full-length CDNA encoding the entire PDGF β-receptor. RP41 was digested with Acc I and Bam HI to isolate the 2.12 kb fragment. RP51 was digested with Eco RI and Acc I to isolate the 982 bp fragment. The 2.12 kb RP41 fragment and the 982 bp RP51 fragment were joined in a three-part ligation with pUC13, which had been linearized by digestion with Eco RI and Bam HI. The resultant plasmid was designated 51/41. Plasmid 51/41 was digested with Eco RI and Bam HI to isolate the 3 kb fragment comprising the partial PDGF receptor cDNA. OT91 was digested with Bam HI and Xba I to isolate the 1.4 kb fragment containing the 3' portion of the PDGF receptor cDNA. The Eco RI-Bam HI 51/41 fragment, the Bam HI-Xba I TO91 fragment and the Eco RI-Xba I digested pUC13 were joined in a three-part ligation. The resultant plasmid was designated pR-RX1 (FIG. 2).

B. Cloning the PDGF-α Receptor

A cDNA encoding to PDGF α-receptor was cloned as follows. RNA was prepared by the method of Chirgwin et al. (*Biochemistry* 18: 5294, 1979) and twice purified on oligo d(T) cellulose to yield poly(A)+RNA. Complementary DNA was prepared in lgt10 phage using a kit purchased from Invitrogen (San Diego, CA). The resulting λ phage DNA was packaged with a coat particle mixture from Stratagene Cloning Systems (La Jolla, Calif.), infected into *E. coli* strain C600 Hfl⁻ and titered.

Approximately 1.4×10⁶ phage recombinants were plated to produce plaques for screening. Nitrocellulose filter lifts were prepared according to standard methods and were hybridized to a radiolabeled PDGF β-receptor DNA fragment (Gronwald et al., ibid.) comprising the 1.9 kb Fsp I-Hind III fragment that encodes the transmembrane and cytoplasmic domains of the PDGF β-receptor cDNA. Hybridization was performed for 36 hours at 42° C. in a mixture containing 40% formamide, 5×SSCP (SSC containing 25 mM phosphate buffer, pH 6.5), 200 μg/ml denatured salmon sperm DNA, 3×Denhardt's, and 10% dextran sulfate. Following hybridization, the filters were washed extensively at room temperature in 2×SSC, then for 15 minutes at 47–48° C. Following an exposure to X-ray film, the filters were treated to increasingly stringent wash conditions followed by film recording until a final wash with 0.1×SSC at 65° C. was reached. Film analysis showed that a "family" of plaques that hybridized at lower wash stringency but not at the highest stringency. This "family" was selected for further analysis.

Two λ phage clones from the "family" obtained from the initial screening were subcloned into the Not I site of the pUCtype plasmid vector pBluescript SK⁺ (obtained from Stratagene Cloning Systems, La Jolla, Calif.) and were analyzed by restriction mapping and sequence analysis. Restriction enzyme analysis of a phage clone, designated α1-1, revealed a restriction fragment pattern dissimilar from that of the PDGF β-receptor CDNA with the exception of a common Bgl II-Bgl II band of approximately 160 bp. The PDGF β-receptor cDNA contains two similarly spaced Bgl II sites within the region coding for the second tyrosine kinase domain.

Restriction analysis of a second plasmid subclone (designated α1-7) revealed an overlap of the 5' approximately 1.2 kb of clone α1-1, and an additional approximately 2.2 kb of sequence extending in the 5' direction. Sequence analysis revealed that the 3' end of this clone encodes the second tyrosine kinase domain, which contains regions of near sequence identity to the corresponding regions in the PDGF β-receptor. The 5' end of clone α1-7 contained non-receptor sequences. Two additional β-receptor clones were obtained by probing with α1-1 sequences. Clone α1-1 was digested with Not I and Spe I, and a 230 bp fragment was recovered. Clone α1-1 was also digested with Bam HI and Not I, and a 550 bp fragment was recovered. A clone that hybridized to the 230 bp probe was designated α5-1. This clone contained the 5'-most coding sequence for the PDGF α-receptor. Another clone, designated α6-3, hybridized to the 550 bp probe and was found to contain 3' coding and non-coding sequences, including the poly(A) tail.

Clone α1-1 was radiolabeled ($^{32}$p) and used to probe a northern blot (Thomas, *Methods Enzymol,* 100: 225–265, 1983) of the MG-63 poly(A)+RNA used to prepare the cDNA library. A single band of approximately 6.6 kb was observed. RNA prepared from receptor-positive cell lines including the human fibroblast SK4, WI-38 and 7573 cell lines; the mouse fibroblast line DI 3T3; the U2-OS human osteosarcoma cell line and baboon aortic smooth muscle cells, and RNA prepared from receptor-negative lines including A431 (an epithelial cell line) and VA 13 (SV40-transformed WI-38 cells) were probed by northern format with the α1-1 cDNA. In all cases, the amount of the 6.6 kb band detected in these RNA correlated well with the relative levels of α-receptor detected on the respective cell surfaces. The 6.6 kb RNA was not detected in RNA prepared from any tested cell line of hematopoietic origin, in agreement with a lack of PDGF α-receptor protein detected on these cell types.

Figure 12:
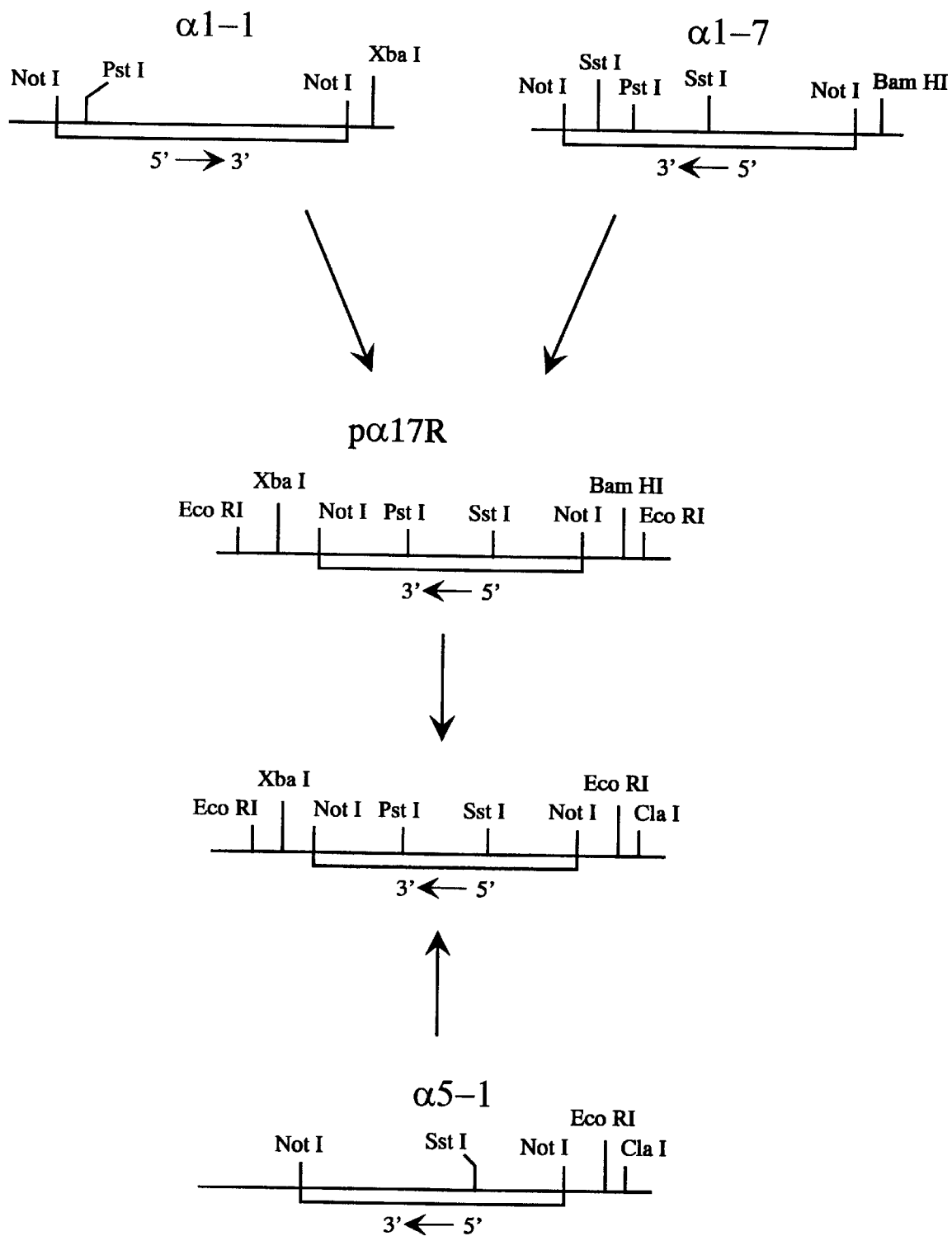
FIG. 12 illustrates the assembly of a cDNA molecule encoding a PDGF α-receptor. Complementary DNA sequences are shown as lines. Only those portions of the vectors adjacent to the cDNA inserts are shown.

Clones α1-1 and and α1-7 were joined at a unique Pst I site in the region encoding the transmembrane portion of the receptor. Clone α1-1 was digested with Xba I and Pst I and the receptor sequence fragment was recovered. Clone α1-7 was digested with Pst I and Bam HI and the receptor fragment was recovered. The two fragments were ligated with Xba I+Bam HI-digested pIC19R (Marsh et al. *Gene* 32: 481–486, 1984) to construct plasmid pα17R (FIG. 12).

The remainder of the 5=-most α-receptor sequence was obtained from clone α5-1 as an Sst I-Cla I fragment. This fragment was joined to the Eco RI-Sst I receptor fragment of pα17R and cloned into Eco RI+Cla I-digested pBluescript SK+plasmid to construct plasmid pα17B (FIG. 12). FIGS. 11A–11D (Sequence ID Numbers 35 and 36) shows the nucleotide sequence and deduced amino acid sequence of the cDNA present in pα17B.

Example 2

Construction of a SUC2 Signal Sequence-PDGF β-Receptor Fusion

To direct the PDGF β-receptor into the yeast secretory pathway, the PDGF β-receptor cDNA was joined to a sequence encoding the *Saccharomyces cerevisiae* SUC2 signal sequence. Oligonucleotides ZC1453 and ZC1454 (Sequence ID Numbers 10 and 11; Table 1) were designed to form an adapter encoding the SUC2 secretory signal flanked by a 5' Eco RI adhesive end and a 3' Bgl II adhesive end. ZC1453 and ZC1454 were annealed under conditions described by Maniatis et al. (ibid.). Plasmid pR-RX1 was digested with Bgl II and Sst II to isolate the 1.7 kb fragment comprising the PDGF β-receptor coding sequence from amino acids 28 to 596. Plasmid pR-RX1 was also cut with Sst II and Hind III to isolate the 1.7 kb fragment comprising the coding sequence from amino acids 597 through the translation termination codon and 124 bp of 3' untranslated DNA. The two 1.7 kb pR-RX1 fragments and the ZC1453/ZC1454 adapter were joined with pUC19, which had been linearized by digestion with Eco RI and Hind III. The resultant plasmid, comprising the SUC2 signal sequence fused in-frame with the PDGF β-receptor cDNA, was designated pBTL10 (FIG. 2).

Example 3

Construction of pCBS22

The BAR1 gene product, Barrier, is an exported protein that has been shown to have three domains. When used in conjunction with a first signal sequence, the third domain of Barrier protein has been shown to aid in the secretion of proteins into the medium (MacKay et al., U.S. patent application Ser. No. 104,316).

Figure 3:
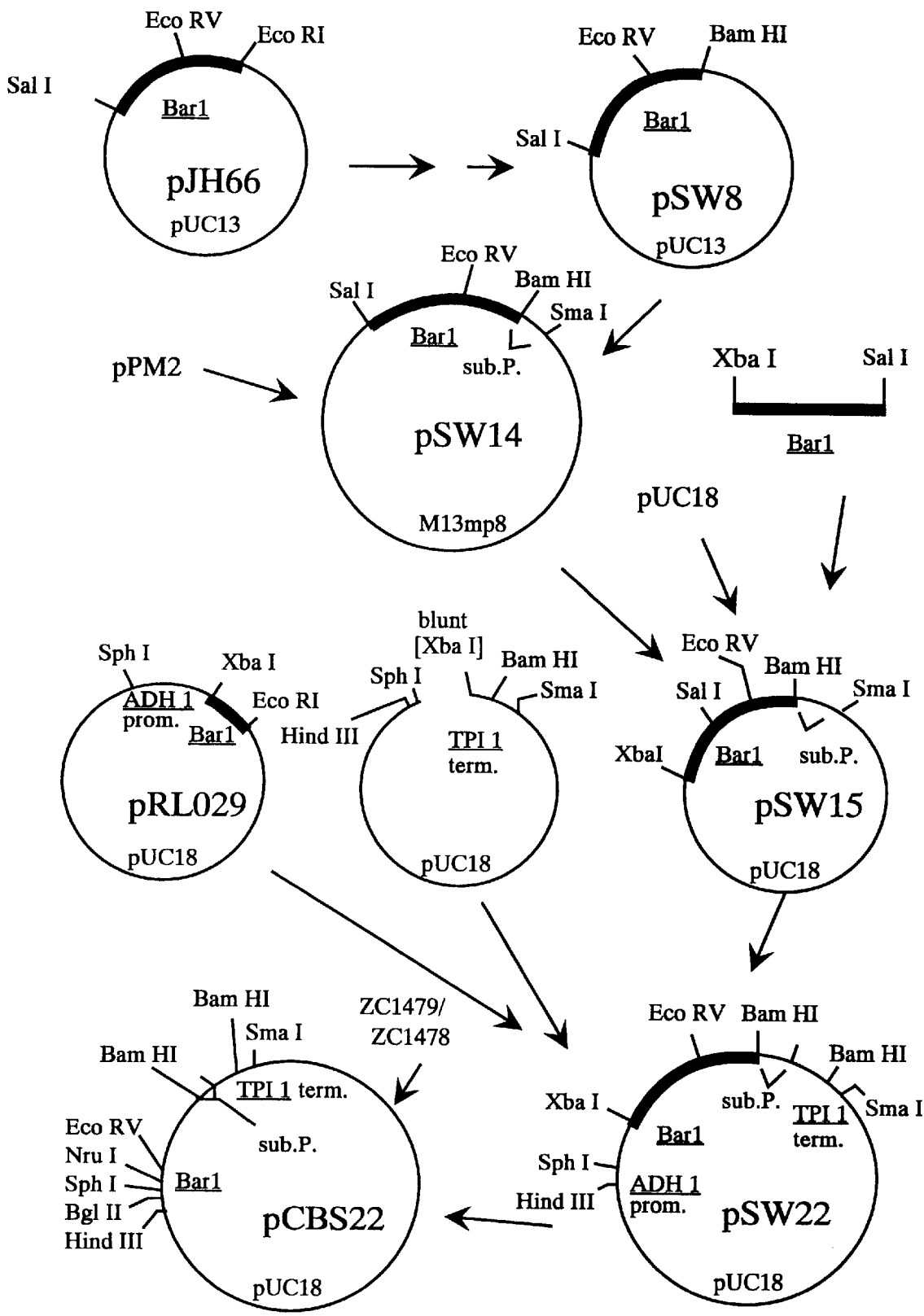
FIG. 3 illustrates the construction of pCBS22.

The portion of the BAR1 gene encoding the third domain of Barrier was joined to a sequence encoding the C-terminal portion of substance P (subP; Munro and Pelham, *EMBO J*. 3: 3087–3093, 1984). The presence of the substance P amino acids on the terminus of the fusion protetn allowed the protein to be detected using commercially available anti-substance P antibodies. Plasmid pZV9 (deposited as a transformant in *E. coli* strain RR1, ATCC accession no. 53283), comprising the entire BAR2 coding region and its associated flanking regions, was cut with Sal I and Bam HI to isolate the 1.3 kb BAR1 fragment. This fragment was subcloned into pUC13, which had been cut with Sal I and Bam HI, to generate the plasmid designated pZV17. Plasmid pZV17 was digested with Eco RI to remove the 3'-most 0.5 kb of the BAR1 coding region. The vector-BAR1 fragment was religated to create the plasmid designated pJH66 (FIG. 3). Plasmid pJH66 was linearized with Eco RI and blunt-ended with DNA polymerase I (Klenow fragment). Kinased Bam HI linkers (5'CCG GAT CCG G 3') were added and excess linkers were removed by digestion with Bam HI before religation. The resultant plasmid was designated pSW8 (FIG. 3).

Plasmid pSW81, comprising the TPI1 promoter, the BAR1 coding region fused to the coding region of the C-terminal portion of substance P (Munro and Pelhamr, *EMBO J*. 3: 3087–3093, 1984) and the TPI1 terminator, was derived from pSW8. Plasmid pSW8 was cut with Sal I and Bam HI to isolate the 824 bp fragment encoding amino acids 252 through 526 of BAR1. Plasmid pPM2, containing the synthetic oligonucleotide sequence encoding the dimer form of the C-terminal portion of substance P (subP) in M13mp8, was obtained from Hugh Pelham (MRC Laboratory of Molecular Biology, Cambridge, England). Plasmid pPM2 was linearized by digestion with Bam HI and Sal I and ligated with the 824 bp BAR1 fragment from pSW8. The resultant plasmid, pSW14, was digested with Sal I and Sma I to isolate the 871 bp BAR1-substance P fragment. Plasmid pSW16, comprising a fragment of BAR1 encoding amino acids 1 through 250, was cut with Xba I and Sal I to isolate the 767 bp BAR1 fragment. This fragment was ligated with the 871 bp BAR1-substance P fragment in a three-part ligation with pUC18 cut with Xba I and Sma I. The resultant plasmid, designated pSW15, was digested with Xba I and Sma I to isolate the 1.64 kb BAR1-substance P fragment. The ADH1 promoter was obtained from pRL029. Plasmid pRL029, comprising the ADH1 promoter and the BAR1 5' region encoding amino acids 1 to 33 in pUC18, -was digested with Sph I and Xba I to isolate the 0.42 kb ADH1 promoter fragment. The TPI1 terminator (Alber and Kawasaki, ibid.) was provided as a linearized fragment containing the TPI1 terminator and pUC18 with a Klenow-filled Xba I end and an Sph I end. This fragment was ligated with the 0.42 kb ADH1 promoter fragment and the 1.64 kb BAR1-substance P fragment in a three-part ligation to produce plasmid pSW22.

The ADH1 promoter and the coding region of BAR1, from the translation initiation ATG through the Eco RV site present in pSW22, were removed by digestion with Hind III and Eco RV. The 3.9 kb vector fragment, comprising the 401 bp between the Eco RV and the Eco RI sites of the BAR1 gene fused to subp and the TPI1 terminator, was isolated by gel electrophoresis. Oligonucleotide ZC1478 (Sequence ID Number 12; Table 1) was kinased and annealed with oligonucleotide ZC1479 (Sequence ID Number 13; Table 1) using conditions described by Maniatis et al. (ibid.). The annealed oligonucleotides formed an adapter comprising a Hind III adhesive end and a polylinker encoding Bgl II, Sph I, Nru I and Eco RV restriction sites. The ZC1479/ZC1478 adapter was ligated with the gel-purified pSW22 fragment. The resultant plasmid was designated pCBS22 (FIG. 3).

Example 4

Construction of pBTL13

Figure 4:
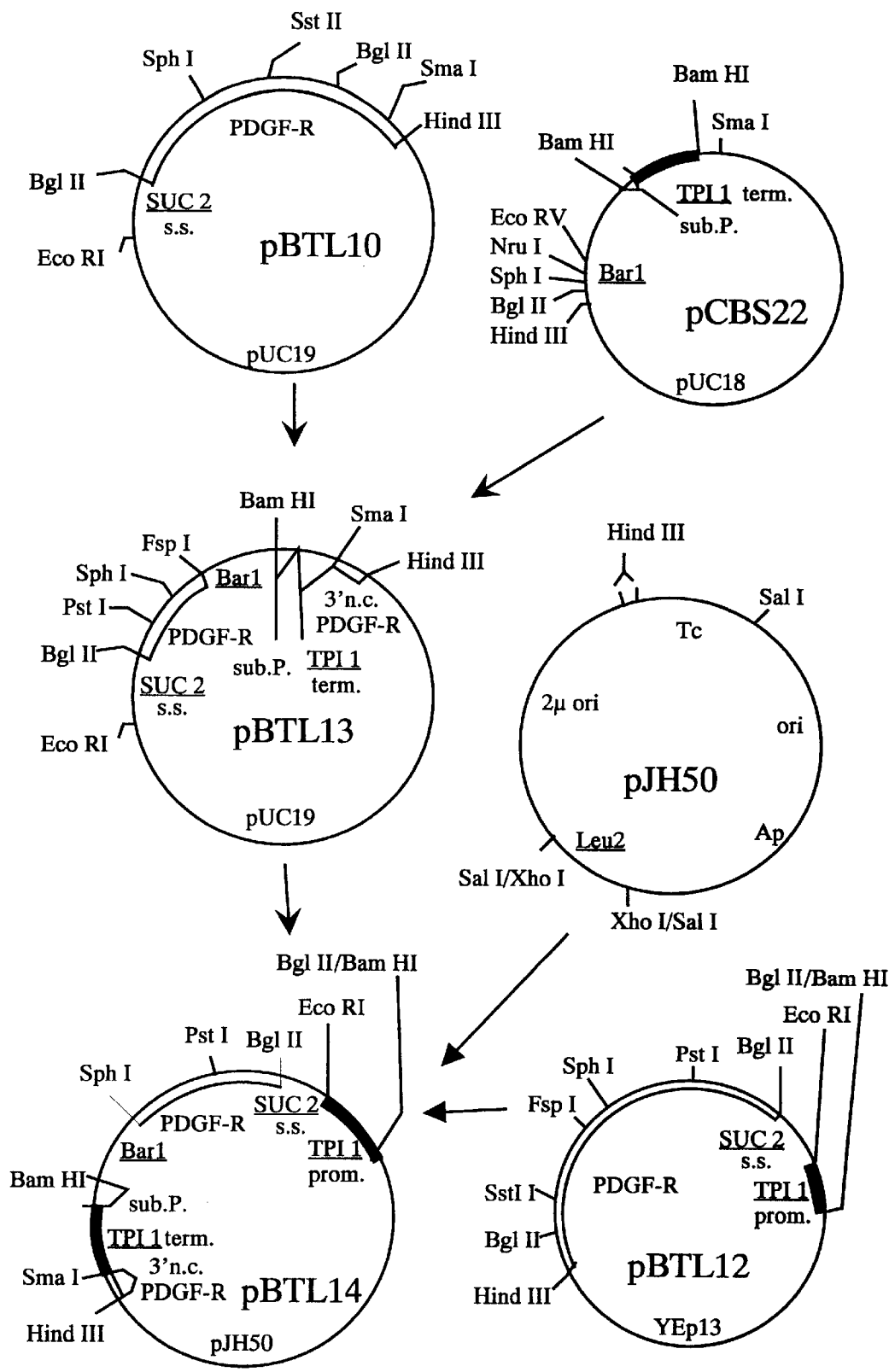
FIG. 4 illustrates the construction of pBTL13 and pBTL14.

In order to enhance the secretion of the β-receptor and to facilitate the identification of the secreted protein, a sequence encoding the third domain of BAR1 fused to the C-terminal amino acids of substance P was fused in frame with the 5' 1240 bp of the PDGF β-receptor. Plasmid pBTL10 (Example 2) was digested with Sph I and Sst I to isolate the 4 kb fragment comprising the SUC2 signal sequence, a portion of the PDGF β-receptor CDNA and the pUC19 vector sequences. Plasmid pCBS22 was digested with Sph I and Sst I to isolate the 1.2 kb fragment comprising the BAR1-subp fusion and the TPI1 terminator. These two fragments were ligated, and the resultant plasmid was designated pBTL13 (FIG. 4).

Example 5

Construction of an Expression Vector Encoding the Entire PDGF β-Receptor

The entire PDGF β-receptor was directed into the secretory pathway by fusing a SUC2 signal sequence to the 5' end of the PDGF β-receptor coding sequence. This fusion was placed behind the TPIL promoter and inserted into the vector YEp13 for expression in yeast.

The TPI1 promoter was obtained from plasmid pTPIC10 (Alber and Kawasaki, *J. Mol. Apnl. Genet.* 1: 410–434, 1982), and plasmid PFATPOT (Kawasaki and Bell, EP 171,142; ATCC 20699). Plasmid pTPIC10 was cut at the unique Kpn I site, the TPI1 coding region was removed with Bal-31 exonuclease, and an Eco RI linker (sequence: GGA ATT CC) was added to the 3' end of the promoter. Digestion with Bgl II and Eco RI yielded a TPI1 promoter fragment having Bgl II and Eco RI sticky ends. This fragment was then joined to plasmid YRp7' (Stinchcomb et al., *Nature* 282: 39–43, 1979) that had been cut with Bgl II and Eco RI (partial). The resulting plasmid, TE32, was cleaved with Eco RI (partial) and Bam HI to remove a portion of the tetracycline resistance gene. The linearized plasmid was then recircularized by the addition of an Eco RI-Bam HI linker to produce plasmid TEA32. Plasmid TEA32 was digested with Bgl II and Eco RI, and the 900 bp partial TPI1 promoter fragment was gel-purified. Plasmid pIC19H (Marsh et al., *Gene* 32:481–486, 1984) was cut with Bgl II and Eco RI and the vector fragment was gel purified. The TPI1 promoter fragment was then ligated to the linearized pIC19H and the mixture was used to transform *E. coli* RR1. Plasmid DNA was prepared and screened for the presence of a ~900 bp Bgl II-Eco RI fragment. A correct plasmid was selected and designated PICTPIP.

The TPI1 promoter was then subcloned to place convenient restriction sites at its ends. Plasmid pIC7 (Marsh et al., ibid.) was digested with Eco RI, the fragment ends were blunted with DNA polymerase I (Klenow fragment), and the linear DNA was recirculatized using T4 DNA ligase. The resulting plasmid was used to transform *E. coli* RR1. Plasmid DNA was prepared from the transformants and was screened for the loss of the Eco RI site. A plasmid having the correct restriction pattern was designated pIC7RI*. Plasmid pIC7RI* was digested with Hind III and Nar I, and the 2500 bp fragment was gel-purified. The partial TPI1 promoter fragment (ca. 900 bp) was removed from pICTPIP using Nar I and Sph I and was gel-purified. The remainder of the TPI1 promoter was obtained from plasmid pFATPOT by digesting the plasmid with Sph I and Hind III, and a 1750 bp fragment, which included a portion of the TPI1 promoter fragment from PICTPIP, and the fragment from pFATPOT were then combined in a triple ligation to produce pMVR1 (FIG. 2).

The TPI1 promoter was then joined to the SUC2-PDGF β-receptor fusion. Plasmid PBTL10 (Example 2) was digested with Eco RI and Hind III to isolate the 3.4 kb fragment comprising the SUC2 signal sequence and the entire PDGF β-receptor coding region. Plasmid pMVR1 was digested with Bgl II and Eco RI to isolate the 0.9 kb TPI1 promoter fragment. The TPI1 promoter fragment and the fragment derived from pBTL10 were joined with YEp13, which had been linearized by digestion with Bam HI and Hind III, in a three-part ligation. The resultant plasmid was designated pBTL12 (FIG. 2).

Example 6

Construction of an Expression Vector Encoding the 5' Extracellular Portion of the PDGF β-Receptor The extracellular portion of the PDGF β-receptor was directed into the secretory pathway by fusing the coding sequence to the SUC2 signal sequence. This fusion was placed in an expression vector behind the TPI1 promoter. Plasmid pBTL10 (Example 2) was digested with Eco RI and Sph I to isolate the approximately 1.3 kb fragment comprising the SUC2 signal sequence and the PDGF β-receptor extracellular domain coding sequence. Plasmid pMVR1 (Example 5) was digested with Bgl II and Eco RI to isolate the 0.9 kb TPI1 promoter fragment. The TPI1 promoter fragment was joined with the fragment derived from pBTL10 and YEp13, which had been linearized by digestion with Bam HI and Sph I, in a three-part ligation. The resultant plasmid was designated pBTL11 (FIG. 2).

Example 7

Construction of Yeast Expression Vectors pBTL14 and pBTL15, and The Expression of PDGF β-Receptor-BAR1-subP Fusions A. Construction of pBTL14

The SUC2-PDGFβ-R fusion was joined with the third domain of BAR1 to enhance the secretion of the receptor, and the expression unit was cloned into a derivative of YEp13 termed pJH50. YEp13 was modified to destroy the Sal I site near the LEU2 gene. This was achieved by partially digesting YEp13 with Sal I followed by a complete digestion with Xho I. The 2.0 kb Xho I-Sal I fragment comprising the LEU2 gene and the 8.0 kb linear YEp13 vector fragment were isolated and ligated together. The ligation mixture was transformed into *E. coli* strain RR1. DNA was prepared from the transformants and was analyzed by digestion with Sal I and Xho I. A clone was isolated which showed a single Sal I site and an inactive Xho I site indicating that the LEU2 fragment had inserted in the opposite orientation relative to the parent plasmid YEp13. The plasmid was designated pJH50.

Referring to FIG. 4, plasmid pBTL12 (Example 5) was digested with Sal I and Pst I to isolate the 2.15 kb fragment comprising 270 bp of YEp13 vector sequence, the TPI1 promoter, the SUC2 signal sequence, and 927 bp of PDGF β-receptor cDNA. Plasmid pBTL13 (Example 4) was digested with Pst I and Hind III to isolate the 1.48 kb fragment comprising 313 bp of PDGF β-receptor CDNA, the BAR1-subP fusion and the TPI1 terminator. The fragments derived from pBTL12 and pBTL13 were joined with pJH50, which had been linearized by digestion with Hind III and Sal I, in a three-part ligation. The resultant plasmid was designated pBTL14.

B. Construction of pBTL15

Figure 5:
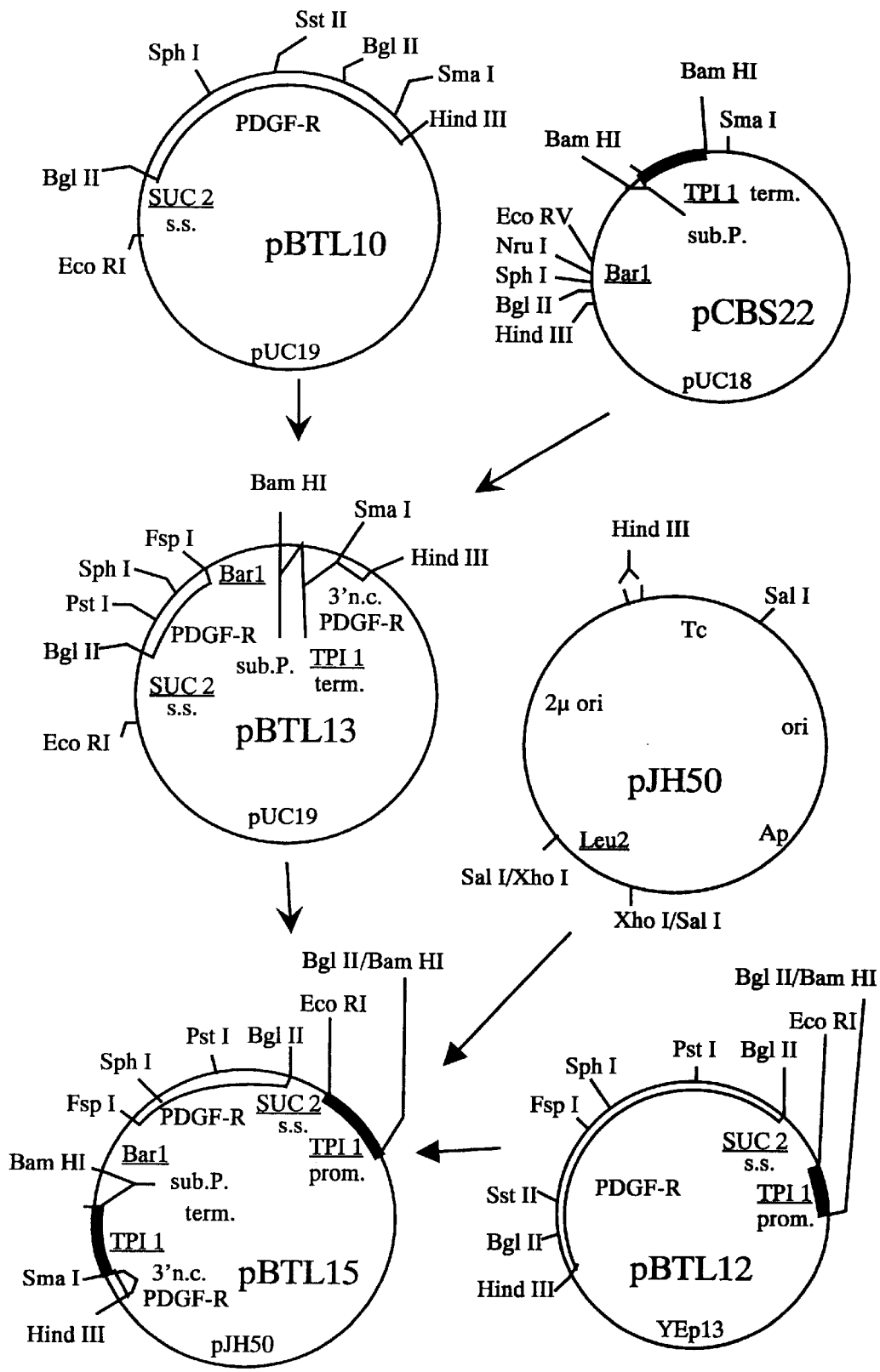
FIG. 5 illustrates the construction of pBTL15.

Referring to FIG. 5, a yeast expression vector was constructed comprising the TPI1 promoter, the SUC2 signal sequence, 1.45 kb of PDGF β-receptor CDNA sequence fused to the BAR1-subP fusion and the TPI1 terminator. Plasmid pBTL12 (Example 5) was digested with Sal I and Fsp I to isolate the 2.7 kb fragment comprising the TPI1 promoter, the SUC2 signal sequence, the PDGFβ-R coding sequence, and 270 bp of YEp13 vector sequence. Plasmid pBTL13 (Example 4) was digested with Nru I and Hind III to isolate the 1.4 kb fragment comprising the BAR1-subP fusion, the TPI1 terminator and 209 bp of 3' PDGF β-receptor cDNA sequence. The fragments derived from pBTL12 and pBTL13 were joined in a three-part ligation with pJH50, which had been linearized by digestion with Hind III and Sal I. The resultant plasmid was designated pBTL15.

C. Expression of PDGFβ-R-subP Fusions from pBTL14 and pBTL15

Yeast expression vectors pBTL14 and pBTL15 were transformed into Saccharomyces cerevisiae strains ZY100 (MATa leu2-3,112 ade2-101 suc2-Δ9 ca12 pep4::TPI1prom-CAT) and ZY400 (MATa leu2-3.112 ade2-101 suc2-Δ9 gal2 pep4::TPI1irom-CAT Δmnn9::URA3). Transformations were carried out using the method essentially described by Beggs (ibid.). Transformants were selected for their ability to grow on –LEUDS (Table 2).

TABLE 2

Media Recipes

-LeuThrTrp Amino Acid Mixture 4 g adenine
3 g L-arginine
5 g L-aspartic acid
2 g L-histidine free base
6 g L-isoleucine
4 g L-lysine-mono hydrochloride
2 g L-methionine
6 g L-phenylalanine
5 g L-serine
5 g L-tyrosine
4 g uracil
6 g L-valine Mix all the ingredients and grind with a mortar and pestle until the mixture is finely ground.

–LEUDS 20 g glucose
6.7 g Yeast Nitrogen Base without amino acids (DIFCO Laboratories Detroit, Mich.)
0.6 g –LeuThrTrp Amino Acid Mixture
182.2 g sorbitol
18 g Agar Mix all the ingredients in distilled water. Add distilled water to a final volume of 1 liter. Autoclave 15 minutes. After autoclaving add 150 mg L-threonine and 40 mg L-tryptophan. Pour plates and allow to solidify.

–LEUDS+sodium succinate. pH 6.5

20 g Yeast Nitrogen Base without amino acids
0.6 g –LeuTrpThr Amino Acid Mixture
182.2 g sorbitol
11.8 g succinic acid Mix all ingredients in distilled water to a final volume of 1 liter. Adjust the pH of the solution to pH 6.5. Autoclave 15 minutes. After autoclaving add 150 mg L-threonine and 40 mg L-tryptophan.

Fermentation Medium 7 g/l yeast nitrogen base without amino acids or ammonium sulfate (DIFCO Laboratories)
0.6 g/l ammonium sulfate
0.5 M sorbitol
0.39 g/l adenine sulfate
0.01% polypropylene glycol Mix all ingredients in distilled water. Autoclave 15 minutes. Add 80 ml 50% glucose for each liter of medium.

Super Synthetic –LEUD. pH 6.5 [liquid or solid medium]

6.7 g Yeast Nitrogen Base without amino acids or ammonium sulfate (DIFCO)
6 g ammonium sulfate
160 g adenine
0.6 g –LeuThrTrp Amino Acid Mixture
20 g glucose
11.8g succinic acid Mix all ingredients and add distilled water to a final volume of 800 ml. Adjust the pH of the solution to pH 6.4. Autoclave 15 minutes. For solid medium, add 18 g agar before autoclaving, autoclave and pour plates.

Super Synthetic –LEUDS, pH 6,4 (liquid or solid medium)

Use the same recipe as Super Synthetic –LEUD, pH 6.4, but add 182.2 g sorbitol before autoclaving.

YEPD 20 g glucose
20 g Bacto Peptone (DIFCO Laboratories)
10 g Bacto Yeast Extract (DIFCO Labloratories)
18 g agar
4 ml adenine 1%
8 ml 1% L-leucine Mix all ingredients in distilled water, and bring to a final volume of 1 liter. Autoclave 25 minutes and pour plates.

The transformants were assayed for binding to an anti-PDGF β-receptor monoclonal antibody (PR7212) or an anti-substance P antibody by protein blot assay. ZY100 [pBTL14] and ZY100[pBTL15] transformants were grown overnight at 30° C. in 5 ml Super Synthetic -LEUD, pH 6.4 (Table 2). ZY400[pBTL14] and ZY400[pBTL15] transformants were grown overnight at 30° C. in 5 ml Super Synthetic-LEUDS, pH 6.4 (Table 2). The cultures were pelleted by centrifugation and the supernatants were assayed for the presence of secreted PDGF β-receptor anlogs by protein blot assay using methods described in Example 18. Results of assays using PR7212 are shown in Table 3.

TABLE 3

Results of a protein blot probed with PR7212

| Transformant: | |
|---|---|
| ZY100[pBTL14] | + |
| ZY400[pBTL14] | ++ |
| ZY100[pBTL15] | + |
| ZY400[pBTL15] | + |

Example 8

Construction of a SUC2-PDGFβ-R Fusion Comprising the Complete PDGFβ-R Extracellular Domain A. Construction of pBTL22

Figure 6:
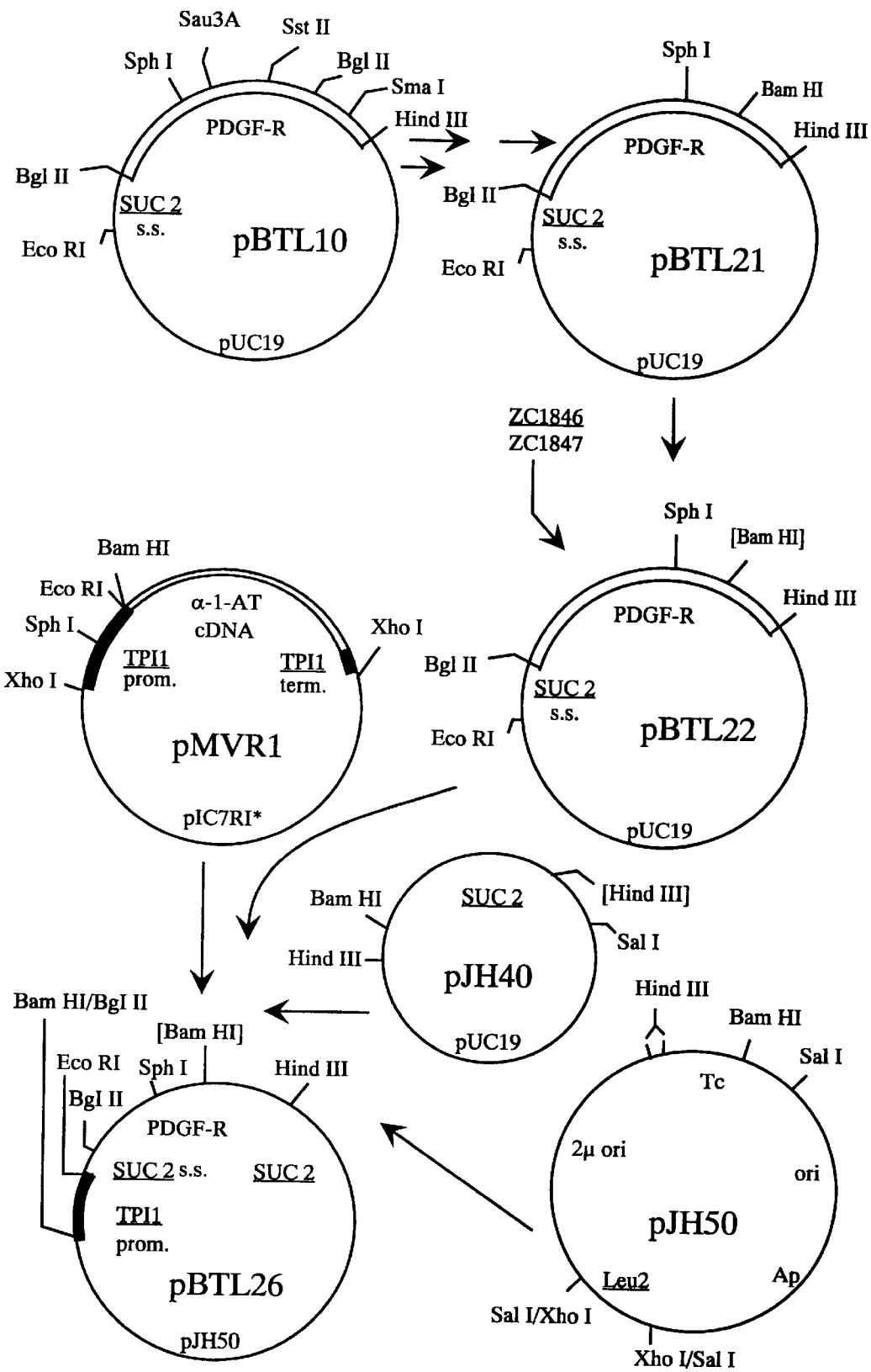
FIG. 6 illustrates the construction of pBTL22 and pBTL26.

The PDGFβ-R coding sequence present in pBTL10 was modified to delete the coding region 3' to the extracellular PDGFβ-R domain. As shown in FIG. 6, plasmid pBTL10 was digested with Sph I and Bam HI and with Sph I and Sst II to isolate the 4.77 kb fragment and the 466 bp fragment, respectively. The 466 bp fragment was then digested with Sau 3A to isolate the 0.17 kb fragment. The 0.17 kb fragment and the 4.77 kb were joined by ligation. The resultant plasmid was designated pBTL21.

Plasmid pBTL21, containing a Bam HI site that was regenerated by the ligation of the Bam HI and Sau 3A sites, was digested with Hind III and Bam HI to isolate the 4.2 kb fragment. Synthetic oligonucleotides ZC1846 (Sequence ID Number 16; Table 1) and ZC1847 (Sequence ID Number 17; Table 1) were designed to form an adapter encoding the PDGFβ-R from the Sau 3A site after bp 1856 (FIG. 1B; (Sequence ID Number 1)) to the end of the extracellular domain at 1958 bp (FIG. 1B; Sequence ID Number 1), having a 5' Bam HI adhesive end that destroys the Bam HI site and a 3' Hind III adhesive end. oligonucleotides ZC1846 and ZC1847 were annealed under conditions described by Maniatis et. al. (ibid.). The 4.2 pBTL21 fragment and the ZC1846/ZC1847 adapter were joined by lrgation. The resultant plasmid, designated pBTL22, comprises the SUC2 signal sequence fused in proper reading frame to the extracellular domain of PDGFβ-R in the vector pUC19 (FIG. 6).

B. Construction of pBTL28

An in-frame translation stop codon was inserted immediately after the coding region of the PDGFβ-R in pBTL22 using oligonucleotides ZC1892 (Sequence ID Number 19; Table 1) and ZC1893 (Sequence ID Number 20; Table 1). These oligonucleotides were designed to form an adapter encoding a stop codon in-frame with the PDGFβ-R coding sequence from pBTL22 flanked by a 5' Hind III adhesive end and a 3' Xba I adhesive end. Plasmid pBTL22 was digested with Eco RI and Hind III to isolate the 1.6 kb SUC2-PDGFβ-R R fragment. Plasmid pMVR1 was digested with Eco RI and Xba I to isolate the 3.68 kb fragment comprising the TPI1 promoter, pIC7RI* vector sequences and the TPI1 terminator. Oligonucleotides ZC1892 and ZClB93 were annealed to form a Hind III-Xba I adapter. The 1.6 kb SUC2-PDGFβ-R fragment, the 3.86 kb pMVR1 fragment and the ZC1892/ZC1893 adapter were joined in a three-part ligation. The resultant plasmid was designated pBTL27.

The expression unit present in pBTL27 was inserted into the yeast expression vector pJH50 by first digesting pJH50 with Bam HI and Sal I to isolate the 10.3 kb vector fragment. Plasmid pBTL27 was digested with Bgl II and Eco RI and with Xho I and Eco RI to isolate the 0.9 kb TPI1 promoter fragment and the 1.65 kb fragment, respectively. The 10.3 kb pJH50 vector fragment, the 0.9 kb TPI1 promoter fragment and 1.65 kb fragment were joined in a three-part ligation. The resultant plasmid was designated pBTL28.

C. Construction of Plasmid pBTL30

The PDGFβ-R coding sequence present in plasmid pBTL22 was modified to encode the twelve C-terminal amino acids of substance P and an in-frame stop codon. Plasmid pBTL22 was digested with Eco RI and Hind III to isolate the 1.6 kb SUC2-PDGFβ-R fragment. Plasmid pMVR1 was digested with Eco RI and Xba I to isolate the 3.68 kb fragment comprising the TPI1 promoter, pIC7RI* and the TPI1 terminator. Synthetic oligonucleotides ZC1894 (Sequence ID Number 21; Table 1) and ZC1895 (Sequence ID Number 22; Table 1) were annealed to form an adapter containing the codons for the twelve C-terminal amino acids of substance P followed by an in-frame stop codon and flanked on the 5' end with a Hind III adhesive end and on the 3' end with an Xba I adhesive end. The ZC1894/ZC1895 adapter, the 1.6 kb SUC2-PDGFβ-R fragment and the pMVR1 fragment were joined in a three-part ligation. The resultant plasmid, designated pBTL29, was digested with Eco RI and Xho I to isolate the 1.69 kb SUC2-PDGFβ-R-subP-TPI1 terminator fragment. Plasmid pBTL27 was digested with Bgl II and Eco RI to isolate the 0.9 kb TPI1 promoter fragment. Plasmid pJH50 was digested with Bam HI and Sal I to isolate the 10.3 kb vector fragment. The 1.69 kb pBTL29 fragment, the 0.9 kb TPI1 promoter fragment and the 10.3 kb vector fragment were joined in a three-part ligation. The resulting plasmid was designated pBTL30.

Example 9

Construction and Expression of a SUC2-PDGFβ-R-IgG Hinge Expression Vector

An expression unit comprising the TPI1 promoter, the SUC2 signal sequence, the PDGFβ-R extracellular domain, an immunoglobulin hinge region and the TPI1 terminator was constructed. Plasmid pBTL22 was digested with Eco RI and Hind III to isolate the 1.56 kb fragment. Plasmid pMVR1 was digested with Eco RI and Xba I to isolate the 3.7 kb fragment, comprising the TPI1 promoter, pIC7RI* vector sequences and the TPI1 terminator. Oligonucleotides ZC1776 (Sequence ID Number 14; Table 1) and ZC1777 (Sequence ID Number 15; Table 1) were designed to form, when annealed, an adapter encoding an immunoglobulin hinge region with a 5' Hind III adhesive end and a 3'Xba I adhesive end. Oligonucleotides ZC1776 and ZC1777 were annealed under conditions described by Maniatis et al. (ibid.). The 1.56 kb pBTL22 fragment, the 3.7 kb fragment and the ZC1776/ZC1777 adapter were joined in a three-part ligation, resulting in plasmid pBTL24.

The expression unit of pBTL24, comprising the TPI1 promoter, SUC2 signal sequence, PDGFβ-R extracellular domain sequence, hinge region sequence, and TPI1 terminator, was inserted into pJH50. Plasmid pBTL24 was digested with Xho I and Hind III to isolate the 2.4 kb expression unit. Plasmid pJH50 was digested with Hind III and Sal I to isolate the 9.95 kb fragment. The 2.4 kb pBTL24 fragment and 9.95 kb pJH50 vector fragment were joined by ligation. The resultant plasmid was designated pBTL25.

Plasmid pBTL25 was transformed into *Saccharomyces cerevisiae* strain ZY400 using the method essentially described by Beggs (ibid.). Transformants were selected for their ability to grow on –LEUDS (Table 2). The transformants were tested for their ability to bind the anti-PDGFβ-R monoclonal antibody PR7212 using the colony assay method described in Example 18. Plasmid pBTL25 transformants were patched onto nitrocellulose filters that had been wetted and supported by YEPD solid medium. Antibody PR7212 was found to bind to the PDGFβ-R-IgG hinge fusion secreted by ZY400[pBTL25] transformants.

Example 10

Construction and Expression of a SUC2 Signal Sequence-PDGFβ-R Extracellular Domain-SUC2 Fusion As shown in FIG. 6, an expression unit comprising the TPI1 promoter, SUC2 signal sequence, PDGFβ-R extracellular domain sequence, and SUC2 coding sequence was constructed as follows. Plasmid pBTL22 was digested with Fco RI and Hind III to isolate the 1.6 kb SUC2-PDGFβ-R fragment. Plasmid pMVR1 was digested with Bgl II and Eco RI to isolate the 0.9 kb TPI1 promoter fragment. The SUC2 coding region was obtained from pJH40. Plasmid pJH40 was constructed by inserting the 2.0 kb Hind III-Hind III SUC2 fragment from pRB58 (Carlson et al., *Cell* 28:145–154, 1982) into the Hind III site of pUC19 followed by the destruction of the Hind III site 3' to the coding region. Plasmid pJH40 was digested with Hind III and Sal I to isolate the 2.0 kb SUC2 coding sequence. Plasmid pJH50 was digested with Sal I and Bam HI to isolate the 10.3 kb vector fragment. The 0.9 kb Bgl II-Eco RI TPI1 promoter fragment, the 1.6 kb Eco RI-Hind III SUC2-PDGFβ-R, the 2.0 kb Hind III-Sal I SUC2 fragment and the 10.3 kb Bam HI-Sal I vector fragment were joined in a four-part ligation. The resultant plasmid was designated pBTL26 (FIG. 6).

Plasmid pBTL26 was transformed into *Saccharomyces cerevisae* strain ZY400 using the method essentially described by Beggs (ibid.). Transformants were selected for their ability to grow on -LEUDS (Table 2). ZY400 transformants (ZY400[pBTL26]) were assayed by protein blot (Example 18), colony blot (Example 18) and competition assay.

Protein blot assays were carried out on ZY400[pBTL26] and ZY400[pJH5O] (control) transformants that had been grown in flasks. Two hundred-fifty microliters of a 5 ml overnight cultures of ZY400[pBTL26] and ZY400 [pJH50] in –LEUDS+sodium succinate, pH 6.5 (Table 2) were inoculated into 50 ml of –LEUDS+sodium succinate, pH 6.5. The cultures were incubated for 35 hours in an airbath shaker at 30° C. The culture supernatants were harvested by centrifugation. The culture supernatants were assayed as described in Example 18 and were found to bind PR7212 antibody.

Colony assays were carried out on ZY400[pBTL26] transformants. ZY400[pBTL26] transformants were patched onto wetted nitrocellulose filters that were supported on a YEPD plate. The colony assay carried out as described in Example 8.A. showed that ZY400[pBTL26] antibodies bound PR7212 antibodies.

Competition binding assays were carried out on ZY400 [pBTL26] and ZY400[pJH50] transformants. The transformants were grown in two liters of fermentation medium (Table 2) in a New Brunswick Bioflo2 fermentor (New Brunswick, Philadelphia, Pa.) with continuous pH control at pH 6.4. The cultures were adjusted to pH 7.5 immediately prior to harvesting. Culture supernatants were concentrated in an Amicon concentrator (Amicon, San Francisco, Calif.) using an Amicon $10^4$ mw spiral filter cartridge. The concentrated supernatants were further concentrated using Amicon Centriprep 10's. Fifteen milliliters of the concentrated supernatant samples were added to the Centripreps, and the Centripreps were spun in a Beckman GRP centrifuge (Beckman Instruments Inc., Carlsbad, Calif.) at setting 5 for a total of 60 minutes. The concentrates were removed from the Centripreps and were assayed in the competition assay.

The competition binding assay measured the amount of $^{125}$I-PDGF left to bind to fetal foreskin fibroblast cells after preincubation with the concentrate containing the PDGFβ-R-SUC2 fusion protein. PDGF-AA and PDGF-AB were iodinated using the Iodopead method (Pierce Chemical). PDGF-BB$_{Tyr}$ was iodinated and purified as described in Example 18.F. The concentrate was serially diluted in binding medium (Table 4). The dilutions were mixed with 0.5 ng of iodinated PDGF-AA, PDGF-BB$_{Tyr}$ or PDGF-AB, and the mixtures were incubated for two hours at room temperature. Three hundred micrograms of unlabeled PDGF-BB was added to each sample mixture. The sample mixtures were added to 24-well plates containing confluent fetal foreskin fibroblast cells (AG1523, available from the Human Genetic Mutant *Cell Repository, Camden, N.J.*). *The cells were incubated with the mixture for four hours at 4° C.* The supernatants were aspirated from the wells, and the wells were rinsed three times with phosphate buffered saline that was held at 4° C. (PBS; Sigma, St. Louis, Mo.). Five hundred microliters of PBS+1% NP-40 was added to each well, and the plates were shaken on a platform shaker for five minutes. The cells were harvested and the amount of iodinated PDGF was determined. The results of the competition binding assay showed that the PDGFβ-R-SUC2 fusion protein was able to competitively bind all three isoforms of PDGF.

The PDGFβ-R produced from ZY400 [pBTL26] transformants was tested for cross reactivity to fibroblast growth factor (FGF) and transforming growth factorβ (TGF-β) using the competition assay essentially described above. Supernatant concentrates from ZY400[pBTL26] and ZY400 [JH50] (control) transformants were serially diluted in binding medium (Table 4). The dilutions were mixed with 7.9 ng of iodinated FGF or 14 ng of iodinated TGF-β, and the mixtures were incubated for two hours at room temperature. Fourteen micrograms of unlabeled FGF was added to each mixture containing labeled FGF, and 7 μg of unlabeled TGF-β was added to each mixture containing labeled TGF-β. The sample mixtures were added to 24-well plates containing confluent human dermal fibroblast cells. (Human dermal fibroblast cells express both FGF receptors and TGFβ receptors.) The cells were incubated with the mixtures for four hours at 4° C. Five hundred microliters of PBS+1% NP-40 was added to each well, and the plates were shaken on a platform shaker for five minutes. The cells were harvested and the amount of iodinated FGF or TGF-β bound to the cells was determined. The results of these assays showed that the PDGFβ-R-SUC2 fusion protein did not cross react with FGF or TGF-β.

TABLE 4

Reagent Recipes

| | Binding Medium |
|---|---|
| 500 ml | Ham's F-12 medium |
| 12 ml | 1M HEPES, pH 7.4 |
| 5 ml | 100x PSN (Penicillin/Streptomycin/Neomycin, Gibco) |
| 1 g | rabbit serum albumin |

| | Western Transfer Buffer |
|---|---|
| 25 mM | Tris, pH 8.3 |
| 19 mM | glycine, pH 8.3 |
| 20% | methanol |

| | Western Buffer A |
|---|---|
| 50 ml | 1 M Tris, pH 7.4 |
| 20 ml | 0.25 mM EDTA, pH 7.0 |
| 5 ml | 10% NP-40 |
| 37.5 ml | 4 M NaCl |
| 2.5 g | gelatin |

The Tris, EDTA, NP-40 and NaCl were diluted to a final volume of one liter with distilled water. The gelatin was added to 300 ml of this solution and the solution was heated in a microwave until the gelatin was in solution. The gelatin solution was added back to the remainder of the first solution and stirred at 4° C. until cool. The buffer was stored at 4° C.

| | Western Buffer B |
|---|---|
| 50 ml | 1 M Tris, pH 7.4 |
| 20 ml | 0.25 M EDTA, pH 7.0 |
| 5 ml | 10% NP-40 |
| 58.4 g | NaCl |
| 2.5 g | gelatin |
| 4 g | N-lauroyl sarcosine |

The Tris, EDTA, NP-40, and the NaCl were mixed and diluted to a final volume of one liter. The gelatin was added to 300 ml of this solution and heated in a microwave until the gelatin was in solution. The gelatin solution was added back to the original solution and the N-lauroyl sarcosine was added. The final mixture was stirred at 4° C. until the solids were completely dissolved. This buffer was stored at 4° C.

| | 2x Loading Buffer |
|---|---|
| 36 ml | 0.5 M Tris-HCl, pH 6.8 |
| 16 ml | glycerol |
| 16 ml | 20% SDS |
| 4 ml | 0.5% Bromphenol Blue in 0.5 M Tris-HCl, pH 6.8 |

Mix all ingredients. Immediately before use, add 100 μl β-mercaptoethanol to each 900 μl dye mix Example 11

Construction and Expression of PDGF Receptor Analogs From BHK cells

A. Construction of pBTL114 and pBTL115

The portions of the PDGF β-receptor extracellular domain present in pBTL14 and pBTL15 were placed in a mammalian expression vector. Plasmids pBTL14 and pBTL15 were digested with Eco RI to isolate the 1695 bp and 1905 bp SUC2 signal-PDGFβ-R-BAR1 fragments. The 1695 bp fragment and the 1905 bp fragment were each ligated to Zem229R that had been linearized by digestion with Eco RI.

The vector Zem229R was constructed as shown in FIG. 10 from Zem229. Plasmid Zem229 is a pUC18-based expression vector containing a unique Bam HI site for insertion of cloned DNA between the mouse metallothionein-1 promoter and SV40 transcription terminator and an expression unit containing the SV40 early promoter, mouse dihydrofolate reductase gene, and SV40 transcription terminator. Zem229 was modified to delete the Eco RI sites flanking the Bam HI cloning site and to replace the Bamr HI site with a single Eco RI cloning site. The plasmid was partially digested with Eco RI, treated with DNA polymerase I (Klenow fragment) and dNTPs, and religated. Digestion of the plasmid with Bam HI followed by ligaion of the linearized plasmid with a Bam HI-Eco I adapter resulted in a unique Eco RI cloning site. The resultant plasmid was designated Zem229R.

Figure 9:
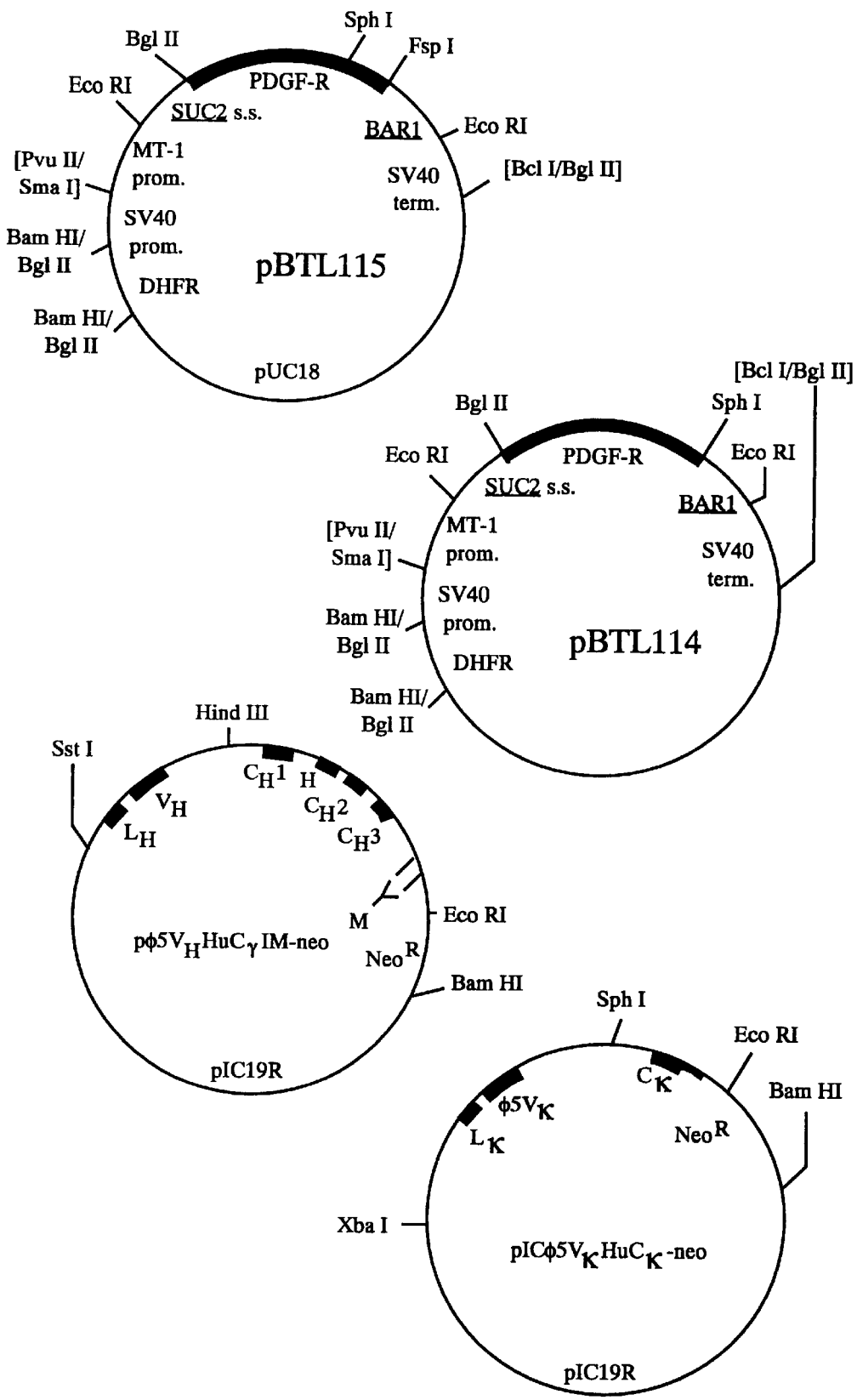
FIG. 9 illustrates the constructions pBTL115, pBTL114, p$\phi$5V$_H$HuC$_\gamma$1M-neo, pIC$\phi$5V$_\kappa$HuC$_\kappa$-neo. Symbols used are set forth in FIGS. 7 and 8, and also include $L_H$, mouse immunoglobulin heavy chain signal sequence; $V_H$, mouse immunoglobulin heavy chain variable region sequence; E, mouse immunoglobulin heavy chain enhancer sequence; $L_\kappa$, mouse immunoglobulin light chain signal sequence; $\phi 5V_\kappa$, mouse immunoglobulin light chain variable region sequence; Neo$^R$, *E. coli* neomycin resistance gene.

The ligation mixtures were transformed into *E. coli* strain RR1. Plasmid DNA was prepared and the plasmids were subjected to restriction enzyme analysis. A plasmid having the 1695 bp pBTL14 fragment inserted into Zem229R in the correct orientation was designated pBTL114 (FIG. 9). A plasmid having the 1905 bp pBTL15 fragment inserted into Zem229R in the correct orientation was designated pBTL115 (FIG. 9).

B. Expression of Secreted PDGF β-Receptor Analogs in tk⁻ts13 BHK Cells

Plasmids pBTL114 and pBTL115 were each transfected into tk⁻ts13 cells using calcium phosphate precipitation (essentially as described by Graham and van der Eb, *J. Gen. Virol.* 36: 59–72, 1977). The transfected cells were grown in Dulbecco's modified Eagle's medium (DMEM) containing 10% fetal calf serum, 1×PSN antibiotic mix (Gibco 600–5640), 2.0 mM L-glutamine. The cells were selected in 250 nM methotrexate (MTX) for 14 days, and the resulting colonies were screened by the immunofilter assay (McCracken and Brown, *Biotechniques*, 82–87, March/April 1984). Plates were rinsed with PBS or No Serum medium (DMEM plus 1×PSN antibiotic mix). Teflon® mesh (Spectrum Medical Industries, Los Angeles, Calif.) was then placed over the cells. Nitrocellulose filters were wetted with PBS or No Serum medium, as appropriate, and placed over the mesh. After six hours incubation at 37° C., filters were removed and placed in Wester buffer A (Table 4) overnight at room temperature. The filters were developed using the antibody PR7212 and the procedure described in Example 8. The filters showed that conditioned media from pBTL114-transfected and pBTL115-transfected BHK cells bound the PR7212 antibody indicating the presence of biologically active secreted PDGFβ-R.

Example 12

Expression of PDGF β-Receptor Analogs in Cultured Mouse Myeloma Cells

A. Construction of pICpPRE8

The immunoglobulin μ heavy chain promoter and enhancer were sublconed into pIC19H to provide a unique Hind III site 3' to the promoter. Plasmid pμ (Grosschedl and Baltimore, *Cell* 41: 885–897, 1985) was digested with Sal I and Eco RI to isolate the 3.1 kb fragment comprising the μ promoter. Plasmid pIC19H was linearized by digestion with Eco RI and Xho I. The p promoter fragment and the linearized pIC19H vector fragment were joined by ligation. The resultant plasmid, designated pICμ3, was digested with Ava II to isolate the 700 bp μ promoter fragment. The 700 bp fragment was blunt-ended by treatment with DNA polymerase I (Klenow fragment) and deoxynucleotide triphosphates. Plasmid pIC19H was linearized by digestion with Xho I, and the adhesive ends were filled in by treatment with DNA polymerase I (Klenow fragement) and deoxynucleotide triphosphates. The blunt-ended Ava II fragment was ligated with the blunt-ended, linearized pIC19H, and the ligation mixture was transformed into *E. coli* JM83. Plasmid DNA was prepared from the transformants and was analyzed by restriction digest. A plasmid with a Bgl II site 5' to the promoter was designated pICμIPR1(−). Plasmid pICμPR1 (−) was digested with Hind III and Bgl II to isolate the 700 bp μ promoter fragment. Plasmid pIC19R was linearized by digestion with Hind III and Bam HI. The 700 bp promoter fragment was joined with the linearized pIC19R by ligation. The resultant plasmid, designated pICμPR7, comprised the μ promoter with an unique Sma I site 5' to the promoter and a unique Hind III site 3' to the promoter.

Figure 7:
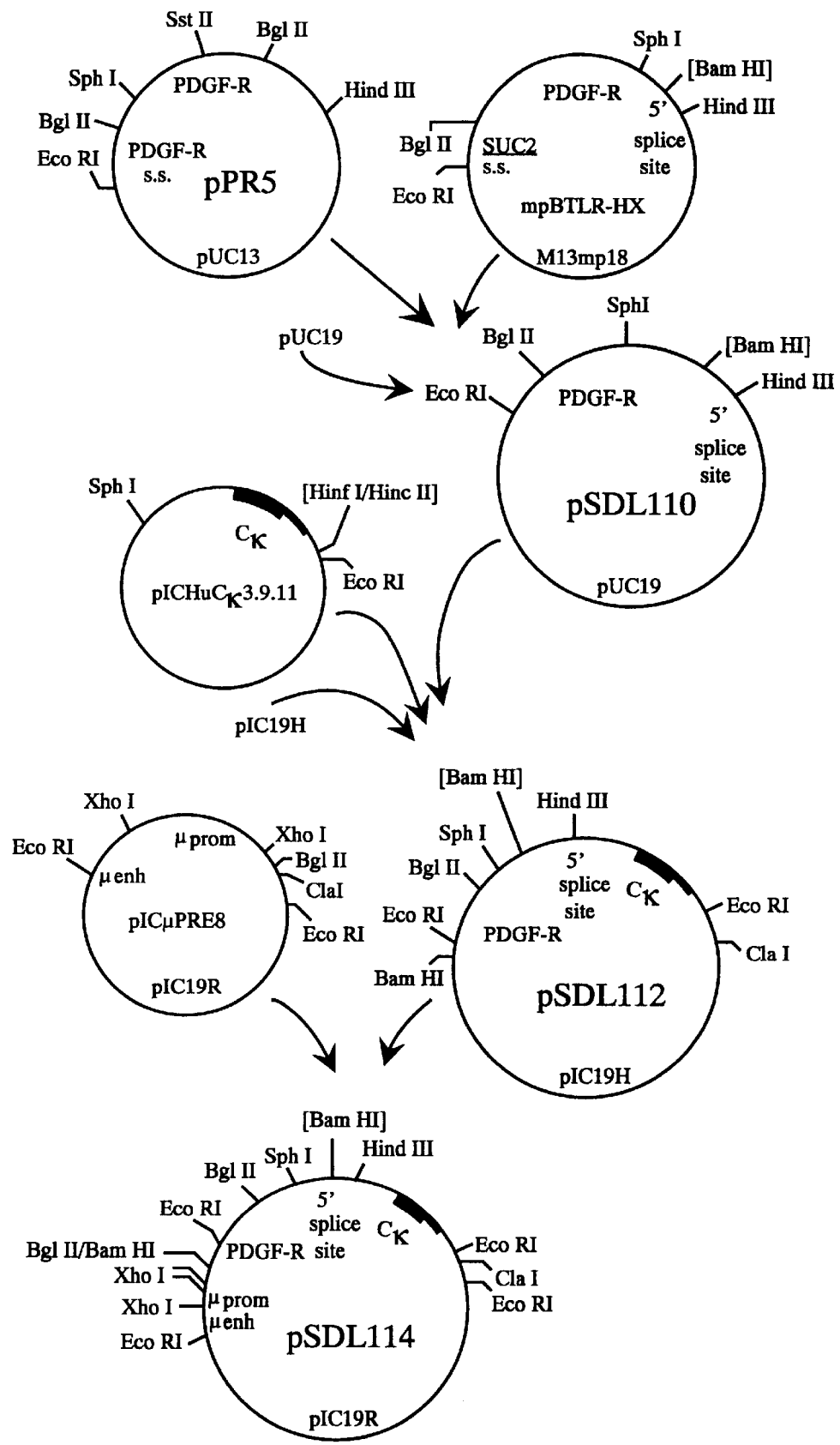
FIG. 7 illustrates the construction of pSDL114. Symbols used are S.S., signal sequence, $C_k$, immunoglobulin light chain constant region sequence; $\mu$ prom, $\mu$ promoter; $\mu$ enh, $\mu$ enhancer.

The immunoglobulin heavy chain μ enhancer (Gillies et al., *Cell* 33: 717–728, 1983) was inserted into the unique Sma I site to generate plasmid pICμPRE8. Plasmid pJ4 (obtained from F. Blattner, Univ. Wisconsin, Madison, Wis.), comprising the 1.5 kb Hind III-Eco RI A enhancer fragment in the vector pAT153 (Amersham, Arlington Heights, Ill.), was digested with Hind III and Eco RI to isolate the 1.5 kb enhancer fragment. The adhesive ends of the enhancer fragment were filled in by treatment with T4 DNA polymerase and deoxynucleotide triphosphates. The blunt-ended fragment and pICμPR7, which had been linearized by digestion with Sma I, were joined by ligation. The ligation mixture was transformed into *E. coli* RR1. Plasmid DNA was prepared from the transformants, and the plasmids were analyzed by restriction digests. A plasmid comprising the μ enhancer and the A promoter was designated pICμPRE8 (FIG. 7).

B. Construction of pSDL114

The DNA sequence encoding the extracellular domain of the PDGF β-receptor was joined with the DNA sequence encoding the human immunoglobulin light chain constant region. The PDGF β-receptor extracellular domain was obtained from mpBTL22, which comprised the Eco RI-Hind III fragment from pBTL22 (Example 8.A.) cloned into Eco RI-Hind III cut M13mp18. Single stranded DNA was prepared from a mpBTL22 phage clone, and the DNA was subjected to in vitro mutagenesis using the oligonucleotide ZC1886 (Table 1) and the method described by Kunkel (*Proc. Natl. Acad. Sci. USA* 82: 488–492, 1985). A phage clone comprising the mutagenized PDGFβ-R with a donor splice site (5° splice site) at the 3' end of the PDGFβ-R extracellular domain was designated pBTLR-HX (FIG. 7).

The native PDGFβ-R signal sequence was obtained from pPR5. Plasmid PPR5, comprising 738 bp of 5' coding sequence with an Eco RI site immediately 5' to the translation initiation codon, was constructed by in vitro mutagenesis of the PDGFβ-R CDNA fragment from RP51 (Example 1). Replicative form DNA of RP51 was digested with Eco RI to is6late the 1.09 kb PDGFβ-R fragment. The PDGFβ-R fragment was cloned into the Eco RI site of M13mp18. Single stranded template DNA was prepared from a phage clone containing the PDGFβ-R fragment in the proper orientation. The template DNA was subjected to in vitro mutagenesis using oligonucleotide ZC1380 (Sequence ID Number 8; Table 1) and the method described by Zoller and Smith (*Meth. Enzymol.* 100: 468–500, 1983). The mutagenesis resulted in the placement of an Eco RI site immediately 5' to the translation initiation codon. Mutagenized phage clones were analyzed by dideoxy sequence analysis. A phage clone containing the ZC1380 mutation was selected, and replicative form (Rf) DNA was prepared from the phage clone. The Rf DNA was digested with Eco RI and Acc I to isolate the 0.63 kb fragment. Plasmid pR-RXI (Example 1) was digested with Acc I and Eco RI to isolate the 3.7 kb fragment. The 0.63 kb fragment and the 3.7 kb fragment were joined by ligation resulting in plasmid pPR5 (FIG. 7).

As shown in FIG. 7, the PDGFβ-R signal peptide and part of the extracellular domain were obtained from plasmid pPR5 as a 1.4 kb Eco RI-Sph I fragment. Replicative form DNA from phage clone pBTLR-HX was digested with Sph I and Hind III to isolate the approximately 0.25 kb PDGFβ-R fragment. Plasmid pUC19 was linearized by digestion with Eco RI and Hind III. The 1.4 kb Eco RI-Sph I PDGFβ-R fragment, the 0.25 kb Sph I-Hind III fragment from pBTLR-HX and the Eco RI-Hind III cut pUC19 were joined in a three-part ligation. The resultant plasmid, pSDL110, was digested with Eco RI and Hind III to isolate the 1.65 kb PDGFβ-R fragment.

Plasmid pICHuCr3.9.11 was used as the source of the human immunoglobulin light chain gene (FIG. 7). The human immunoglobulin light chain gene was isolated from a human genomic library using an oligonucleotide probe (5' TGT GAC ACT CTC CTG GGA GTT A 3'; Sequence ID Number 32), which was based on a published human kappa C gene sequence (Hieter et al., *Cell* 22: 197–207, 1980). The human light chain (kappa) constant region was subdloned as a 1.1 kb Sph I-Hinf I genomic fragment of the human kappa gene, which has been treated with DNA polymerase DNA I (Klenow Fragment) to fill in the Hinf I adhesive end, into Sph I-Hinc II cut pUC19. The 1.1 kb human kappa constant region was susbsequently isolated as a 1.1 kb Sph I-Bam HI fragment that was subdloned into Sph I-Bgl II cut pIC19R (Marsh et al., ibid.). The resultant plasmid was designated pICHuCX3.9.11. Plasmid pICHuC$_{78}$ 3.9.11 was digested with Hind III and Eco RI to isolate the 1.1 kb kappa constant region gene. Plasmid pIC19H was linearized by digestion with Eco RI. The 1.65 kb PDGFβ-R fragment, the 1.1 kb human kappa constant region fragment and the linearized pIC19H were joined in a three part ligation. The resultant plasmid, pSDL112, was digested with Bam HI and Cla I to isolate the 2.75 kb fragment. Plasmid ppPRE8 was linearized with Bgl II and Cla I. The 2.75 kb fragment and the linearized ppPRE8 were joined by ligation. The resultant plasmid was designated pSDL114 (FIG. 7).

Plasmid pSDL114 was linearized by digestion with Cla I and was cotransfected with Pvu I-digested p416 into SP2/0-Ag14 (ATCC CRL 1581) by electroporation using the method essentially described by Neumann et al. (*EMBO J.* 1: 841–845, 1982). (Plasmid p416 comprises the Adenovirus 5 ori, SV40 enhancer, Adenovirus 2 major late promoter, Adenovirus 2 tripartite leader, 5' and 3' splice sites, the DHFR$^r$ CDNA, the SV40 polyadenylation signal and 1 ML-1 (Lusky and Botchan, *Nature* 2: 79–81, 1981) vector sequences.) Transfectants were selected in growth medium containing methotrexate.

Media from drug resistant clones were tested for the presence of secreted PDGF β-receptor analogs by enzyme-linked immunosorbant assay (ELISA). Ninety-six well assay plates were prepared by incubating 100 µl of 1 µg/ml polyclonal goat anti-human kappa chain (Cappel Laboratories, Melvern, Pa.) diluted in phosphate buffered saline (PBS; Sigma) overnight at 4° C. Excess antibody was removed by three washes with 0.5% Tween 20 in PBS. One hundred microliters of spent media was added to each well, and the well were incubated for one hour at 4° C. Unbound proteins were removed by eight washes with 0.5% Tween 20 -in PBS. One hundred microliters of peroxidase-conjugated goat anti-human kappa antibody (diluted 1:1000 in a solution containing 5% chicken serum (GIBCO-BRL)+0.5% Tween 20 in PBS) was added to each well and the wells were incubated for one hour at 4° C. One hundred microliters of chromophore (100 u1 ABTS (2,2'-Azinobis(3-ethylbenz-thiazoline sulfonic acid) diammonium salt; Sigma)+1 µl 30% $H_2O_2$+12.5 ml citrate/phosphate buffer (9.04 g/l citric acid, 10.16 g/l $Na_2HPO_4$)) was added to each well, and the wells were incubated to thirty minutes at room temperature. The samples were measured at 405 nm. The results of the assay showed that the PDGFβ-R analog secreted by the transfectants contained an immunoglobulin light chain.

Spent media from drug resistant clones was also tested for the presence of secreted PDGF β-receptor analogs by immunoprecipitation. Approximately one million drug resistant transfectants were metabolically labeled by growth in DMEM medium lacking cysteine+2% calf serum for 18 hours at 37° C. in the presence of 50 µCI $^{35}$5-cysteine. Media was harvested from the labeled cells and 250 µl of the spent media was assayed by immunoprecipitation with the anti-PDGF β-receptor antibody PR7212 to detect the prsence of metabolically labeled PDGF β-receptor analogs. PR7212, diluted in PBS, was added to the media to a final concentration of 2.5 µg per 250 µl spent media. Five microliters of rabbit anti-mouse Ig diluted in PBS was added to the PR7212/media mixtures. The immunocomplexes were precipitated by the addition of 50 µl 10% fixed Staph A (weight/volume in PBS). The immunocomplexes were analyzed on 8% SDS-polyacrylamide gels followed by autoradiography overnight at −70° C. The results of the immunoprecipitation showed that the PDGF β-receptor analog secreted by the transfectants was bound by the anti-PDGF β-receptor antibody. The combined results of the ELISA and immunoprecipitation assays showed that the PDGF β-receptor analog secreted by the transfectants contained both the PDGF β-receptor ligand-binding domain and the human light chain constant region.

C. Cotransfection of pSDL114 with an Immunoglobulin Heavy Chain

Plasmid pSDL114 was cotransfected with pφ5V$_H$huC$_γ$1M-neo, which encodes a neomycin resistance gene expression unit and a complete mouse/human chimeric immunoglobulin heavy chain gene expression unit.

Plasmid pφ5V$_H$huC$_γ$1M-neo was constructed as follows. The mouse immunoglobulin heavy chain gene was isolated from a lambda genomic DNA library constructed from the murine hybridoma cell line NR-ML-05 (Serafini et al., *Eur. J. Nucl. Med.* 14: 232, 1988) using an oligonucleotide probe designed to span the V$_H$/D/J$_H$ junction (5'GCA TAG TAG TTA CCA TAT CCT CTT GCA CAG 3'; Sequence ID Number 33). The human immunoglobulin gamma-1 C gene was isolated from a human genomic library using a cloned human gamma-4 constant region gene (Ellison et al., *DNA* 1: 11–18, 1981). The mouse immunoglobulin variable region was isolated as a 5.3 kb Sst I-Hind III fragment from the original phage clone and the human gamma-1 C gene was obtained from the original phage clone as a 6.0 kb Hind III-Xho I fragment. The chimeric gamma-1 C gene was created by joining the V$_H$ and C$_H$ fragments via the common Hind III site and incorporating them with the *E. coli* neomycin resistance gene expression unit into pIC19H to yield pφ5V$_H$huC$_γ$1M-neo.

Plasmid pSDL114 was linearized by digestion with Cla I and was co-transfected into SP2/0-Ag14 cells with Asp 718 linearized pϕ5V$_H$huC$_γ$1M-neo. The transfectants were selected in growth medium containing methotrexate and neomycin. Media from drug-resistant clones were tested for their ability to bind PDGF in a competition binding assay.

The competition binding assay measured the amount of $^{125}$-PDGF left to bind to human dermal fibroblast cells after preincubation with the spent media from pSDL114-pϕ5V$_H$huC$_γ$1M-neo transfected cells. The media were serially diluted in binding medium (Table 4). The dilutions were mixed with 0.5 ng of iodinated PDGF-BB or iodinated PDGF-AA, and the mixtures were incubated for two hours at room temperature. Three hundred micrograms of unlabeled PDGF-BB or unlabeled PDGF-AA was added to one tube from each series. The sample mixtures were added to 24 well plates containing confluent human dermal fibroblast cells. The cells were incubated with the mixture for four hours at 4° C. The supernatants were aspirated from the wells, and the wells were rinsed three times with phosphate buffered saline that was held a 4° C. (PBS; Sigma, St. Louis, Mo.). Five hundred microliters of PBS+1% NP-40 was added to each well, and the plates were shaken on a platform shaker for five minutes. The cells were harvested and the amount of iodinated PDGF was determined. The results of the competition binding assay showed that the protein produced from pSDL114-pϕ5V$_H$huC$_γ$1M- neo transfected cells was able to competetively bind PDGF-BB but did not bind PDGF-AA.

The PDGF β-receptor analog produced from a pSDL114-pϕ5V$_H$huC$_γ$1M-neo transfectant was assayed to determine if the receptor analog was able to bind PDGF-BB with high affinity. Eight and one half milliliters of spent media containing the PDGFβ-R analogs from a pSDL114-pϕ5V$_H$huC$_γ$1M-neo transfectant was added to 425 μl of Sepharose Cl-4B-Protein A beads (Sigma, St. Louis, Mo.), and the mixture was incubated for 10 minutes at 4° C. The beads were pelleted by centrifugation and washed with binding medium (Table 4). Following the wash the beads were resuspended in 8.5 ml of binding media, and 0.25 ml aliquots were dispensed to 1.5 ml tubes. Binding reactions were prepared by adding iodinated PDGF-BB$_{Tyr}$ (Example 18.F.) diluted in DMEM+10% fetal calf serum to the identical aliquots of receptor-bound beads to final PDGF-BB$_{Tyr}$ concentrations of between 4.12 pM and 264 pM. Nonspecific binding was determined by adding a 100 fold excess of unlabeled BB to an identical set of binding reactions. Mixtures were incubated overnight at 4° C.

The beads were pelleted by centrifugation, and unbound PDGF-BB was removed with three washes in PBS. The beads were resuspended in 100 μl of PBS and were counted. Results of the assay showed that the PDGFβ-R analog was able to bind PDGF-BB with high affinity.

D. Construction of pSDL113.

Figure 8:
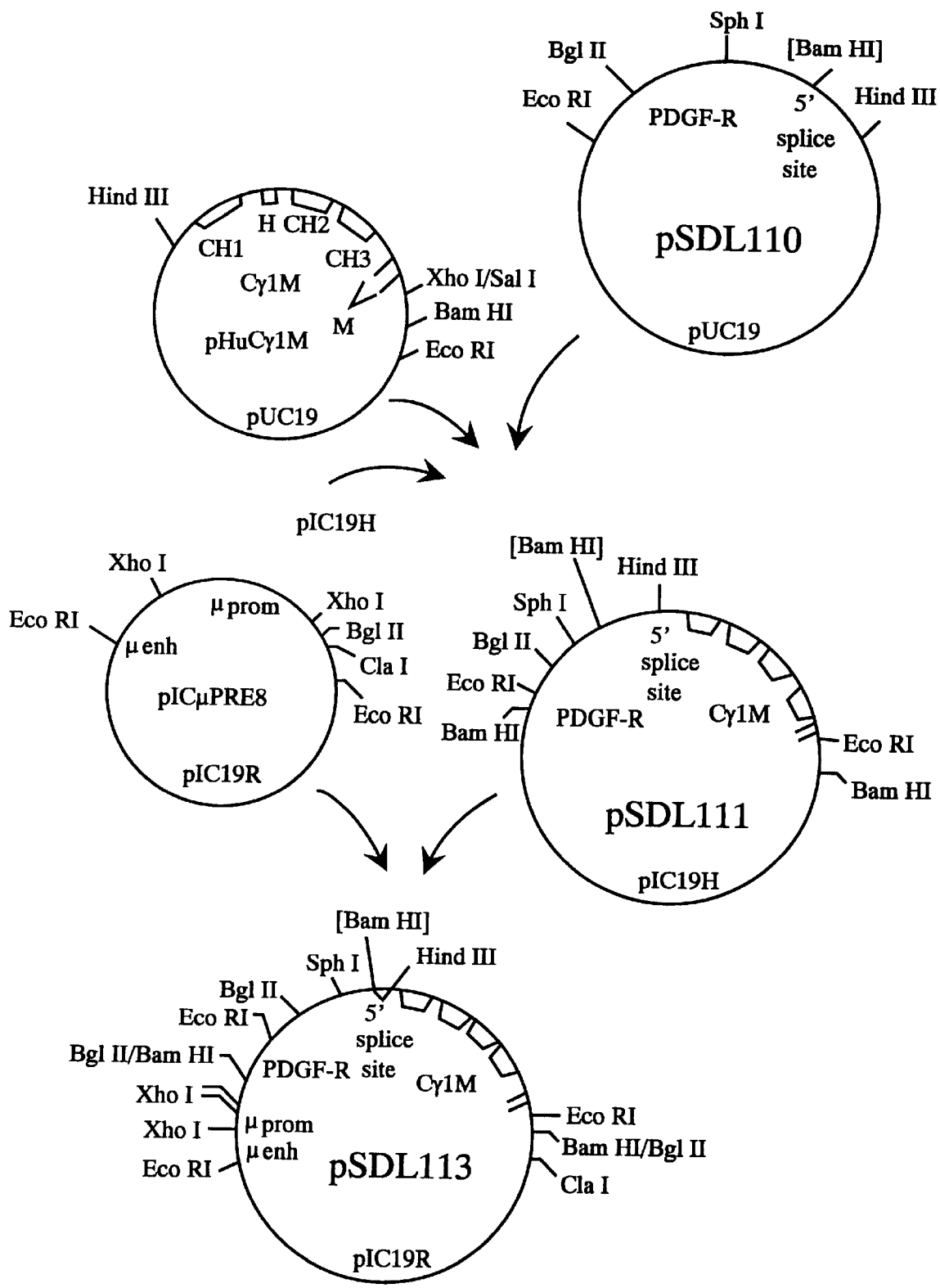
FIG. 8 illustrates the construction of pSDLB113. Symbols used are S.S., signal sequence; $C_H1$, $C_H2$, $C_H3$, immunoglobulin heavy chain constant region domain sequences; H, immunoglobulin heavy chain hinge region sequence; M, immunoglobulin membrane anchor sequences; $c_\gamma 1M$, immunoglobulin heavy chain constant region and membrane anchor sequences.

As shown in FIG. 8, the DNA sequence encoding the extracellular domain of the PDGF β-receptor was joined with the DNA sequence encoding a human immunoglobulin heavy chain constant region joined to a hinge sequence. Plasmid pSDL110 was digested with Eco RI and Hind III to isolate the 1.65 kb PDGFβ-R fragment. Plasmid pICHu$_γ$-1M was used as the source of the heavy chain constant region and hinge region. Plasmid pICHu$_γ$-1M comprises the approximately 6 kb Hind III-Xho I fragment of a human gamma-1 C gene subcloned into pUC19 that had been linearized by digestion with Hind III and Sal I. Plasmid pICHu$_γ$-1M was digested with Hind III and Eco RI to isolate the 6 kb fragment encoding the human heavy chain constant region. Plasmid pIC19H was linearized by digestion with Eco RI. The 1.65 kb PDGFβ-R fragment, the 6 kb heavy chain constant region fragment and the linearized pIC19H were joined in a three part ligation. The resultant plasmid, pSDL111, was digested with Bam HI to isolate the 7.7 kb fragment. Plasmid pμPRE8 was linearized with Bgl II and was treated with calf intestinal phosphatase to prevent self-ligation. The 7.7 kb fragment and the linearized pμPRE8 were joined by ligation. A plasmid containing the insert in the proper orientation was designated pSDL113 (FIG. 8).

Plasmid pSDL113 is linearized by digestion with Cla I and is cotransfected with Pvu I-digested p416 into SP2/0-Ag14 by electroporation. Transfectants are selected in growth medium containing methotrexate.

Media from drug resistant clones are tested for the presence of secreted PDGFβ-R analogs by immunoprecipitation using the method described in Example 12.B.

E. Cotransfection of pSDL113 with an Immunoglobulin Light Chain Gene

Plasmid pSDL113 is linearized by digestion with Cla I and was cotransfected with pICϕ5V$_κ$HuC$_κ$-Neo, which encodes a neomycin resistance gene and a mouse/human chimeric immunoglobulin light chain gene. The mouse immunoglobulin light chain gene was isolated from a lambda genomic DNA library constructed from the murine hybridoma cell line NR-ML-05 (Woodhouse et al., ibid.) using an oligonucleotide probe designed to span the V$_κ$/J$_κ$ junction (5' ACC GAA CGT GAG AGG AGT GCT ATA A 3'; Sequence ID Number 34). The human immunoglobulin light chain constant region gene was isolated as described in Example 12.B. The mouse NR-ML-05 immunoglobulin light chain variable region gene was subcloned from the original mouse genomic phage clone into pIC19R as a 3 kb Xba I-Hinc II fragment. The human kappa C gene was subcloned from the original human genomic phage clone into pUC19 as a 2.0 kb Hind III-Eco RI fragment. The chimeric kappa gene was created by joining the NR-ML-05 light chain variable region gene and human light chain constant region gene via the common Sph I site and incorporating them with the *E. coli* neomycin resistance gene into pIC19H to yield pICϕ5V$_κ$HuC$_κ$-Neo (FIG. 9).

The linearized pSDL113 and pICϕ5V$_κ$HuC$_κ$-Neo are transfected into SP2/0-Ag14 cells by electroporation. The transfectants are selected in growth medium containing methotrexate and neomycin.

F. Cotransfection of pSDL113 and pSDL114

A clone of SP2/0-Ag14 stably transfected with pSDL114 and p416 was co-transfected with Cla I-digested pSDL113 and Bam HI-digested pICneo by electroporation. (Plasmid pICneo comprises the SV40 promoter operatively linked to the *E. coli* neomycin resistance gene and pIC19H vector sequences.) Transfected cells were selected in growth medium containing methotrexate and G418. Media from drug-resistanct clones were tested for their ability to bind PDGF-BB or PDGF-AA in a competition binding assay as described in Example 12.C. The results of the assay showed that the transfectants secreted a PDGF β-receptor analog which was capable of competitively binding PDGF-BB but did not detectably bind to PDGF-AA.

G. Cotransfection of pSDL114 with Fab

A clone of SP2/0-AG14 stably transfected with pSDL114 and p416 was transfected with the Fab region of the human gamma-4 gene (γ$_4$) in plasmid pϕ5V$_H$Fab-neo.

Plasmid pϕ5V$_H$Fab-neo was constructed by first digesting plasmid p24BRH (Ellison et al., *DNA* 1: 11, 1988) was digested with Xma I and Eco RI to isolate the 0.2 kb fragment comprising the immunoglobulin 3' untranslated region. Synthetic oligonucleotides ZC871 (Sequence ID Number 3; Table 1) and ZC872 (Sequence ID Number 4; Table 1) were kinased and annealed using essentially the methods described by Maniatis et al. (ibid.). The annealed oligonucleotides ZC871/ZC872 formed an Sst I-Xma I adapter. The ZC871/ZC872 adapter, the 0.2 kb p24BRH fragment and Sst I-Eco RI linearized pUC19 were joined in a three-part ligation to form plasmid $p\gamma_43'$. Plasmid $p\gamma_43'$ was linearized by digestion with Bam HI and Hind III. Plasmid p24BRH was cut with Hind III and Bgl II to isolate the 0.85 kb fragment comprising the $C_H1$ region. The $p\gamma_43'$ fragment and the Hind III-Bgl II p24BRH fragment were joined by ligation to form plasmid $p\gamma_4$Fab. Plasmid $p\gamma_4$Fab was digested with Hind III and Eco RI to isolate the 1.2 kb fragment comprising $\gamma_4$Fab. Plasmid pICneo, comprising the SV40 promoter operatively linked to the E. coli neomycin resistance gene and pIC19H vector sequences, was linearized by digestion with Sst I and Eco RI. Plasmid $p\phi5V_H$, comprising the mouse immunoglobulin heavy chain gene variable region and pUC18 vector sequences, was digested with Sst I and Hind III to isolate the 5.3 kb $V_H$ fragment. The linearized pICneo was joined with the 5.3 kb Sst I-Hind III fragment and the 1.2 kb Hind III-Eco RI fragment in a three-part ligation. The resultant plasmid was designated $p\phi5V_H$Fab-neo (FIG. 10).

A pSDL114/p416-transfected SP2/0-AG14 clone was transfected with Sca I-linearized $p\phi5V_H$Fab-neo. Transfected cells were selected in growth medium containing methotrexate and G418. Media from drug-resistant clones were tested for their ability to bind PDGF in a competition binding assay as described in Example 12.C. The results of the assay showed that the PDGF β-receptor analog secreted from the transfectants was capable of competitively binding PDGF-BB.

H. Cotransfection of pSDL114 with Fab'

A stably transfected SP2/0-AG14 isolate containing pSDL114 and p416 was transfected with plasmid pWKI, which contained the Fab' portion of an immunoglobulin heavy chain gene. Plasmid pWKI was constructed as follows.

The immunoglobulin gamma-1 Fab' sequence, comprising the $C_H1$ and hinge regions sequences, was derived from the gamma-1 gene clone described in Example 12.C. The gamma-1 gene clone was digested with Hind III and Eco RI to isolate the 3.0 kb fragment, which was subcloned into Hind III-Eco RI linearized M13mp19. Single-stranded template DNA from the resultant phage was subjected to site-directed mutagenesis using oligonucleotide ZC1447 (Sequence ID Number 9; Table 1) and essentially the method of Zoller and Smith (ibid.). A phage clone was identified having a ZC1447 induced deletion resulting in the fusion of the hinge region to a DNA sequence encoding the amino acids Ala-Leu-His-Asn-His-Tyr-Thr-Glu-Lys-Ser-Leu-Ser-Leu-Ser-Pro-Gly-Lys (Sequence ID Number 31) followed in-frame by a stop codon. Replicative form DNA from a positive phage clone was digested with Hind III and Eco RI to isolate the 1.9 kb fragment comprising the $C_H1$ and hinge regions. Plasmid $p\phi5V_H$ was digested with Sst I and Hind III to isolate the 5.3 kb fragment comprising the mouse immunoglobulin heavy chain gene variable region. Plasmid pICneo was linearized by digestion with Sst I and Eco RI. The linearized pICneo was joined with the 5.3 kb Hind III-Sst I fragment and the 1.9 kb Hind III-Eco RI fragment in a three-part ligation. The resultant plasmid was designated pWKI (FIG. 10).

An SP2/0-AG14 clone stably transfected with pSDL114 and p416 was transfected with Asp 718-linearized pWKI. Transfected cells were selected by growth in medium containing methotrexate and G418. Media samples from transfected cells were assayed using the competition assay described in Example 12.C. Results from the assays showed that the transfected cells produced a PDGF β-receptor analog capable of competetively binding PDGF-BB.

Example 13

Purification and Characterization of PDGF β-Receptor Analogs from Mammalian cells Co-transfected With pSDL113 and pSDL114

A. Purification of PDGF β-Receptor Analogs

The PDGF β-receptor analog was purified from conditioned culture media from a clone of transfected cells grown in a hollow fiber system. The media was passed over a protein-A sepharose column, and the column was washed sequentially with phosphate buffered saline, pH 7.2 (PBS; Sigma, St. Louis, Mo.) and 0.1 M citrate, pH 5.0. The PDGF β-receptor analog was eluted from the protein-A column with 0.1 M citrate pH 2.5 and immediately neutralized by the addition of Tris-base, pH 7.4. The eluate fractions containing PDGF β-receptor analog, as determined by silver stain, were pooled and chromatographed over an S-200 column (Pharmacia LKB Technologies, Inc., Piscataway, N.J.) equilibrated with PBS. The peak fractions from the S-200 column were pooled and concentrated on a centriprep-10 concentrator (Amicon). Glycerol (10% final volume) was added to the preparation and the sample frozen at −80° C. PDGF β-receptor analogs purified from pSDL114+ pSDL113 co-transfected cells were termed "tetrameric PDGF α-receptors".

B. Measurement of The Relative Binding Affinity of Tetrameric PDGF β-Receptor Analog by Soluble Receptor Assay Purified tetrameric PDGF β-receptor analog was compared to detergent solubilized extracts of human dermal fibroblasts for $^{125}$I-labeled PDGF-BB binding activity in a soluble receptor assay essentially as described by Hart et al. (J. Biol. Chem. 262: 10780–10785, 1987). Human dermal fibroblast cells were extracted at 20×10$^6$ cell equivalents per ml in TNEN extraction buffer (20 mM Tris-HCl, pH 8.0, 100 mM NaCl, 1 mM EDTA, 0.5% Nonidet P-40, 1 mM PMSF, 10% glycerol). Two hundred and fifty thousand PDGF β-receptor-subunits per cell was used to calculate the tetrameric PDGF β-receptor analog number per volume of extract. This value has been previously published by Seifert et al. (J. Biol Chem. 264: 8771–8778, 1989). The PDGF β-receptor analog number was determined from the protein concentration of the PDGF β-receptor analog assuming an average molecular weight of 140 kDa for each immunoglobulin-PDGF β-receptor monomer, and four monomers per tetramer. Thus, each tetrameric molecule contains four receptor molecules.

Increasing amounts of either detergent solubilized extracts of human dermal fibroblast cells or purified PDGF β-receptor analog were incubated with 1 ng of $^{125}$I-labeled PDGF-BB for one hour at 37° C. The sample was then diluted with 1 ml binding media and was added to monolayers of human dermal fibroblast cells grown in 24-well culture dishes. The samples were incubated for two hours at 4° C. The wells were washed to remove unbound, $^{125}$I-labeled PDGF-BB. On half of a milliliter of extraction buffer (PBS+1% Nonidet P-40) was added to each well followed by a 5 minute incubation. The extraction mixtures were harvested and counted in a gamma counter.

The results showed that the PDGF β-receptor analog had the same relative binding affinity as solubilized PDGF β-receptor-subunit from mammalian cells in a solution phase binding assay.

C. Determination of the Binding Affinity of the PDGF β-Receptor Analog in a Solid Phase Format The apparent dissociation constant $K_D$(app) of the PDGF β-receptor analog was determined essentially as described by Bowen-Pope and Ross (*Methods in Enzymology* 109: 69–100, 1985), using the concentration of $^{125}$I-labeled PDGF-BB giving half-maximal specific $^{125}$I-labeled PDGF-BB binding. Saturation binding assays to determine the concentration of $^{125}$I-labeled PDGF-BB that gave half-maximal binding to immobilized PDGF β-receptor analog were conducted as follows.

Affinity purified goat anti-human IgG, H- and L-chain (Commercially available from Cappel Labs) was diluted into 0.1 M $Na_2HCO_3$, pH 9.6 to a concentration of 2 μg/ml. One hundred microliters of the antibody solution was coated onto each well of 96-well microtiter plates for 18 hours at 4° C. The wells were washed once with ELISA C buffer (PBS+ 0.05% Tween-20) followed by an incubation with 175 μl/well of ELISA B buffer (PBS+1% BSA+0.05% Tween-20) to block the wells. The wells were washed once with ELISA B buffer. One hundred microliters of 12.1 ng/ml or 24.3 ng/ml of tetrameric PDGF β-receptor analog protein diluted in ELISA B was added to each well and the plates were incubated for 2 hours at 37° C. Unbound protein was removed from the wells by two washes with ELISA C. $^{125}$I-labeled PDGF-BB$_{Tyr}$ (Example 18.F.) was serially diluted into binding media (25 mM HEPES, pH 7.2, 0.25% rabbit serum albumin diluted in HAMs P-12 medium (GIBCO-BRL)), and 100 μl of the dilutions were added to the wells. The plates were incubated for two hours at room temperature. The unbound $^{125}$I-labeled PDGF-BB was removed, and the wells were washed three times with binding media. Following the last wash, 100 μl of 0.1 M citrate, pH 2.5 was added to each well. After five minutes, the citrate buffer was removed, transferred to a tube and counted in a gamma counter. The counts reflect counts of $^{125}$I-labeled PDGF-BB$_{Tyr}$ bound by the receptor analog. Nonspecific binding for each concentration of $^{125}$I-labeled PDGF-BB$_{Tyr}$ was determined by a parallel assay wherein separate wells coated only with goat anti-human IgG were incubated with the $^{125}$I-labeled PDGF-BB concentrations. Nonspecific binding was determined to be 2.8% of the total input counts per well and averaged 6% of the total counts bound.

Saturation binding assay on 12.1 and 24.3 ng/ml of tetrameric PDGF β-receptor analog gave half-maximal binding at 0.8 and 0.82 ng/ml $^{125}$I-labeled PDGF-BB$_{Tyr}$, respectively. By Scatchard analysis (Scatchard, *Ann. NY Acad. Sci* 51: 660–667, 1949) these values were shown to correspond to a $K_D$(app) of $2.7 \times 10^{-11}$ which agree with the published values for PDGF receptors on mammalian cells.

Example 14

Solid Phase Ligand Binding Assay Using the PDGF β-Receptor Analog

A. Solid Phase Radioreceptor Competition Binding Assay

In a solid phase radioreceptor competition binding assay (RRA), the wells of 96-well microtiter plates were coated with 100 μl of 2 μg/ml affinity purified goat anti-human IgG (Cappel Labs) diluted in 0.1 M $Na_2HCO_3$, pH 9.6. After an eighteen hour incubation at 4° C., the wells were washed once with ELISA C. The wells were blocked by incubation for 2 hours at 37° C. with 175 μl/well ELISA B. The wells were washed once with ELISA B then incubated for 2 hours at 37° C. with 50 ng/ml tetrameric PDGF β-receptor analog diluted in ELISA B. The unbound receptor was removed, and the test wells were incubated with increasing concentrations of serially diluted, unlabeled PDGF-BB (diluted in binding media. Following a two hour incubation at room temperature, the wells were washed three times with binding media. One hundred microliters of 5 ng/ml $^{125}$I-labeled PDGF-BB$_{Tyr}$ (Example 18.F.) was added to each well, and the plates were incubated for an additional two hours at room temperature. The wells were washed three times with binding media followed by a 5 minute incubation with 100 μl/well of 0.1 M citrate, pH 2.5. The samples were harvested and counted in a gamma counter.

Radioreceptor assay (RRA) competition binding curves were generated for PDGF β-receptor analog protein plated at 48.6 ng/ml. The sensitivity of the assays is 1 ng/ml of PDGF-BB, with 8 ng/ml giving 50% inhibition in $^{125}$I-PDGF-BB binding, and a working range between 1 and 32 ng/ml of PDGF-BB. The values were similar to those obtained using monolayers of SK-5 cells in an RRA.

B. Use of Tetrameric PDGF β-Receptor Analogs As Antagonists for PDGF-Stimulated Mitogenesis.

A tetrameric PDGF β-receptor analog, purified as described in Example 13, was analyzed for the ability to neutralize PDGF-stimulated mitogenesis in mouse 3T3 cells. Increasing amounts of the purified tetrameric PDGF β-receptor analog were mixed with 5 ng of PDGF. The mixtures were then added to cultures of mouse 3T3 cells. The ability of the PDGF to stimulate a mitogenic response, as measured by the incorporation of $^3$H-thymidine, was determined essentially as described (Raines and Ross, *Methods in Enzymology* 109: 749–773, 1985, which is incorporated by reference herein). The tetrameric PDGF β-receptor analog demonstrated a dose response inhibition of PDGF-BB-stimulated $^3$H-thymidine incorporation, while having essentially no effect on PDGF-AA- and PDGF-AB-stimulated $^3$H-thymidine incorporation.

C. Binding of Tetrameric PDGF β-receptor Analog to Immobilized PDGF.

A tetrameric PDGF β-receptor analog, purified as described in Example 13, was analyzed for its ability to bind to immobilized PDGF. PDGF-BB (100 ng/ml) was coated onto wells a 96-well microtiter plate, and the plates were incubated 18 hours at 4° C. followed by one wash with ELISA C buffer. The wells were incubated for 2 hours 37° C. with ELISA B buffer to block the wells. Increasing concentrations of $^{125}$I-labeled tetrameric PDGF β-receptor analog, diluted in binding media, was added to the wells for two hours at room temperature. The wells were washed four times with ELISA C buffer to remove unbound receptor analog. One hundred microliters of 1 M $H_2SO_4$ was added to each well and the plates were incubated for five minutes at room temperature. The solution was then harvested and transferred to tubes to be counted in a gamma counter. Nonspecific binding was determined to be less than 10% of the total counts bound.

A receptor competition binding assay was developed using this assay format. The assay was carried out as described above, and simultaneous to the addition of the $^{125}$I-labeled tetrameric PDGF β-receptor analog, increasing amounts of PDGF-AA, AB or BB were added to the PDGF-BB coated wells. Under these condtions, only PDGF-BB was found to significantly block the binding of the labeled PDGF β-receptor analog to the immobilized PDGF-BB.

Example 15

Construction and Expression of PDGFα-R Analogs in Cultured Mouse Myeloma Cells

A. Construction of an optimized PDGFα-R cDNA

The PDGF α-receptor coding region was optimized for expression in mammalian cells as follows. The 5' end of the cDNA was modified to include an optimized Kozak consensus translation initiation sequence (Kozak, *Nuc. Acids Res.* 12: 857–872, 1984) and Eco RI and Bam HI sites just 5' of the initiation methionine codon. Oligonucleotides ZC2181, ZC2182, ZC2183 and ZC2184 (Sequence ID Numbers 23, 24, 25 and 26, respectively; Table 1) were designed to form, when annealed, an adapter having an Eco RI adhesive end, a Bam HI restriction site, a sequence encoding a Kozak consensus sequence 5' to the initation methionine codon, a mammalian codon optimized sequence encoding amino acids 1–42 of FIGS. 11A–11D, and an Eco RI adhesive end that destroys the Eco RI site within the PDGFα-R coding sequence. The adapter also introduced a diagnostic Cla I site 3' to the initiation methionine codon. Oligonucleotides ZC2181, ZC2182, ZC2183 and ZC2184 were kinased, annealed and ligated. Plasmid pα17B was linearized by partial digestion with Eco RI. The linearized pα17B was ligated with the ZC2181/2C2182/ZC2183/ ZC2184 oligonucleotide adapter, and the ligation mixture was transformed into *E. coli*. Plasmid DNA prepared from the transformants was analyzed by restriction analysis and a positive clone having the oligonucleotide adapter in the correct orientation was digested with Eco RI and Pst I to isolate the 1.6 kb fragment. This fragment was subcloned into Eco RI+Pst I-linearized M13mp19. The resultant phage clone was designated 792-8. Single-stranded 792-8 DNA was sequenced to confirm the orientation of the adapter.

A fragment encoding the ligand-binding domain of the PDGF α-receptor (PDGFα-R) was then generated as follows. Restriction sites and a splice donor sequence were introduced at the 3' end of the PDGFα-R extracellular domain by PCR amplification of the 792-8 DNA and oligonucleotides ZC2311 and ZC2392 (Sequence ID Numbers 27 and 30, Table 1). Oligonucleotide ZC2311 is a sense primer encoding nucleotides 1470 to 1489 of FIG. 11B. Oligonucleotide ZC2392 is an antisense primer that encodes nucleotides 1759 to 1776 of FIG. 11B followed by a splice donor and Xba I and Hind III restriction sites. The 792-8 DNA was amplified using manufacturer recommended (Perkin Elmer Cetus, Norwalk, Conn.) conditions and the GeneAmp™ DNA amplification reagent kit (Perkin Elmer Cetus), and blunt-ended 329 bp fragment was isolated. The blunt-end fragment was digested with Nco I and Hind III and ligated with Sma I-digested pUC18. A plasmid having an insert with the Nco I site distal to the Hind III site present in the pUC18 polylinker was designated pUC18 Sma-PCR Nco HIII #13. The Hind III site present in the insert was not regenerated upon ligation with the linearized pUC18. Plasmid pUC18 Sma-PCR Nco HIII #13 was digested with Nco I and Hind III to isolate the 355 bp PDGFα-R containing fragment encoding PDGFαR. oligonucleotides ZC2351 and ZC2352 (Table 1; Sequence ID Numbers 28 and 29) were kinased and annealed to form an Sst I-Nco I adapter encoding an internal Eco RI site and a Kozak consensus translation initiation site. The 355 bp Nco I-Hind III fragment, the ZC2351/ZC2352 adapter and a 1273 bp Nco I fragment comprising the extracellular domain of of PDGF α-R derived from 792-8 were ligated with Hind III+SstI-digested pUC18. and tranformed into *E. coli*. Plasmid DNA was isolated from the transformants and analyzed by restriction analysis. None of the isolates contained the 1273 bp Nco I fragment. A plasmid containing the Nco I-Hind III fragment and the ZC2351/ZC2352 adapter was desginated pUC18 Hin Sst Δ Nco #46. Plasmid pUC18 Hin Sst Δ Nco #46 was linearized by digestion and joined by ligation with the 1273 bp Nco I fragment comprising the extracellular domain of the PDGFα-R from clone α18 R-19. The ligations were transformed into *E. coli*, and plasmid DNA was isolated from the transformants. Analysis of the plasmid DNA showed that only clones with the Nco I fragment in the wrong orientation were isolated. A clone having the Nco I fragment in the wrong orientation was digested with Nco I, religated and transformed into *E. coli*. Plasmid DNA was isolated from the transformants and was analyzed by restriction analysis. A plasmid having the Nco I insert in the correct orientation was digested to completion with Hind III and partially digested with Sst I to isolate the 1.6 kb fragment comprising the extracellular domain of the PDGFα-R preceded by a consensus initiation sequence (Kozak, ibid.) and followed by a splice donor site.

B. Construction of pPAB7

The DNA sequence encoding the extracellular domain of the PDGFα-R was joined to the immunoglobulin μ enhancer-promoter and to a DNA sequence encoding an immunoglobulin light chain constant region. The immunoglobulin μ enhancer-promoter was obtained from plasmid pJH1 which was derived from plasmid PICμPRE8 (Example 12.A.) by digestion with Eco RI and Sst I to isolate the 2.2 kb fragment comprising the immunoglobulin enhancer and heavy chain variable region promoter. The 2.2 kb Sst I-Eco RI fragment was ligated with Sst I+Eco RI-linearized pUC19. The resulting plasmid, designated pJH1, contained the immunoglobulin enhancer and heavy chain variable region promoter immediately 5' to the pUC19 linker sequences. Plasmid pJH1 was linearized by digestion with Sst I and Hind III and joined with the 1.6 kb partial Sst I-Hind III fragment containing the PDGFα-R extracellular domain sequences. The resulting plasmid having the immunoglobulin μ enhancer-promoter joined to the PDGFα-R extracellular domain was designated pPAB6. Plasmid pSDL112 was digested with Hind III to isolate the 1.2 kb fragment encoding the immunoglobulin light chain constant region (Cκ). The 1.2 kb Hind III fragment was ligated with Hind III-linearized pPAB6. A plasmid having the $C_\kappa$ sequence in the correct orientation was desginated pPAB7.

C. Construction of pPAB9

The partial Sst I-Hind III fragment encoding the extracellular domain of the PDGFα-R was joined to the immunoglobulin heavy chain constant region. For convenience, the internal Xba I site in plasmid pJH1 was removed by digestion with Xba I, blunt-ending with T4 DNA polymerase, and religation. A plasmid which did not contain the internal Xba I site, but retained the Xba I site in the polylinker was desginated 11.28.3.6. Plasmid 11.28.3.6 was linearized by digestion with Sst I and Xba I. Plasmid pPAB6 was digested to completion with Hind III and partially digested with Sst I to isolate the 1.6 kb Sst I-Hind III fragment containing the PDGFα-R extracellular domain. Plasmid pφ5V$_H$huC$_\gamma$1M-neo (Example 12.C.) was digested wtih Hind III and Xba I to isolate the 6.0 kb fragment encoding the immunoglobulin heavy chain constant region (huC$_\gamma$1M). The Sst I-Hind III-linearized 11.28.3.6, the 1.6 kb Sst I-Hind III PDGFα-R fragment and the 6.0 kb Hind III-Xba I huC$_\gamma$1M fragment were ligated to form plasmid pPAB9.

D. Expression of pPAB9 in Mammalian Cells

Bgl II-linearized pPAB7 and Pvu I-linearized pPAB9 were cotransfected with Pvu I-linearized p416 into SP2/0-Ag14 cells by electroporation. Transfected cells were initially selected in growth medium containing 50 nM methotrexate and were subsequently amplified in a growth medium containing 100 μM methotrexate. Media from drug resistant clones were tested for the presence of secreted PDGF α-receptor analogs by enzyme-linked immunosorbant assay (ELISA). Ninety-six well assay plates were prepared by incubating 100 μl of 1 μg/ml monoclonal antibody 292.1.8 which is specific for the PDGF α-receptor diluted in phosphate buffered saline (PBS; Sigma] overnight at 4° C. Excess antibody was removed by three washes with 0.5% Tween 20 in PBS. One hundred microliters of spent media was added to each well, and the plates were incubated for one hour at 4° C. Unbound proteins were removed by eight washes with 0.5% Tween 20 in PBS. One hundred microliters of peroxidase-conjugated goat anti-human IgG heavy chain antibody (diluted 1:1000 in a solution containing 5% chicken serum (GIBCO-BRL)+0.5% Tween 20 in PBS) was added to each well, and the plates were incubated for one hour at 4° C. One hundred microliters of chromophore (100 μl ABTS [2,2'-Azinobis(3-ethylbenzthiazoline sulfonic acid] diammonium salt; Sigma]+1 μl 30% $H_2O_2$+12.5 ml citrate/phosphate buffer [9.04 g/l citric acid, 10.16 g/l $Na_2HPO_4$]) was added to each well, and the wells were incubated for 30 minutes at room temperature. The samples were measured at 405 nm. The results of the assay showed that the PDGF α-receptor analogs secreted by the transfectants contained an immunoglobulin heavy chain.

Analysis of spent media from transfected cells by Northern analysis, Western analysis and by radioimmunoprecipitation showed that the transfectants did not express a PDGF α-receptor analog from the pPAB7 construction. Transfectants were subsequently treated as containing only pPAB9.

Drug resistant clones were also tested for the presence of secreted PDGF α-receptor analogs by immunoprecipitation. For each clone, approximately one million drug resistant transfectants were grown in DMEM lacking cysteine+2% calf serum for 18 hours at 37° C. in the presence of 50 μCi $^{35}$S-cysteine. The spent media was harvested from the labeled cells and 250 μl of medium from each clone was assayed for binding to the anti-PDGF α-receptor antibody 292.18. Monoclonal antibody 292.18 diluted in PBS was added to each sample to a final concentration of 2.5 μg per 250 μl spent media. Five microliters of rabbit anti-mouse Ig diluted in PBS was added to each sample, and the immunocomplexes were precipitated by the addition of 50 μl 10% fixed Staph A (weight/volume in PBS). The immunocomplexes were analyzed on 8% SDS-polyacrylamide gels followed by autoradiography overnight at −70° C. The results of the immunoprecipitation showed that the PDGF α-receptor analog secreted by the transfectants was bound by the anti-PDGF α-receptor antibody. The combined results of the ELISA and immunoprecipitation assays showed that the PDGF α-receptor analog secreted by the transfectants contained both the PDGF α-receptor ligand-binding domain and the human heavy chain.

Spent medium from drug-resistant clones were tested for their ability to bind PDGF in a competition binding assay esssentially as described in Example 12.C. The results of the assay showed that the transfectants secreted a PDGF α-receptor analog capable of binding PDGF-AA. A clone containing the pPAB9 was desgniated 3.17.1.57.

E. Co-expression of pPAB7 and pPAB9 in Mammalian Cells

Bgl II-linearized pPAB7 and Bam HI-linearized pICneo were cotransfected into clone 3.17.1.57, and transfected cells were selected in the presence of neomycin. Media from drug resistant cells were assayed for the presence of immunoglobulin heavy chain, immunoglobulin light chain and the PDGF α-receptor ligand-binding domain by ELISA essentially as described above. Briefly, ninety-six well assay plates were prepared by incubating 100 μl of 1 μg/ml goat anti-human IgG Fc antibody (Sigma) or 100 μl of 1 μg/ml 292.18 overnight at 4° C. Excess antibody was removed by three washes with 0.5% Tween 20 in PBS. One hundred microliters of spent media was added to each well of each plate, and the plates were incubated for one hour at 4° C. Unbound proteins were removed by eight washes with 0.5% Tween 20 in PBS. One hundred microliters of peroxidase-conjugated goat anti-human IgG antibody (diluted 1:1000 in a solution containing 5% chicken serum (GIBCO-BRL)+ 0.5% Tween 20 in PBS) was added to each well of the plate coated with the anti-Fc antibody, and 100 μl of peroxidase-conjugated goat anti human kappa antibody (diluted 1:1000 in a solution containing 5% chicken serum (GIBCO-BRL)+ 0.5% Tween 20 in PBS) was added to each well of the plate coated with 292.18. The plates were incubated for one hour at 4° C. One hundred microliters of chromophore (100 μl ABTS (2,2'-Azinobis(3-ethylbenz-thiazoline sulfonic acid) diammonium salt; Sigma]+1 μl 30% $H_2O_2$+12.5 ml citrate/ phosphate buffer [9.04 g/l citric acid, 10.16 g/l $Na_2HPO_4$]) was added to each well of each plate, and the plates were incubated to 30 minutes at room temperature. The samples were measured at 405 nm, the wavelength giving maximal absorbance of the chromogenic substrate, to identify clones having absorbances higher than background indicating the presence of immunoglobulin heavy chain. Clones that gave positive results in both ELISA assays (showing that the clones produced proteins containing heavy chain regions, light chain constant regions and the PDGF α-receptor ligand-binding region) were selected for further characterization.

Drug resistant clones that were positive for both ELISA assays were subsequently tested for the presence of secreted PDGF α-receptor analogs by immunoprecipitation. For each positive clone, approximately one million drug resistant transfectants were grown in DMEM lacking cysteine+2% calf serum for 18 hours at 37° C. in the presence of 50 μCl $^{35}$S-cysteine. The spent media was harvested from the labeled cells and 250 μl of medium from each clone was assayed for binding to monoclonal antibody 292.18. Monoclonal antibody 292.18 diluted in PBS was added to each sample to a final concentration of 2.5 μg. Five microliters of rabbit anti-mouse Ig diluted in PBS was added to each sample and the immunocomplexes were precipitated by the addition of 50 μl 10% fixed Staph A (weight/volume in PBS). The immunocomplexes were analyzed on 8% SDS-polyacrylamide gels followed by autoradiography overnight at −70° C. The results of the immunoprecipitation showed that the PDGF α-receptor analog secreted by the transfectants was bound by the anti-PDGF α-receptor antibody. The combined results of the ELISA and immunoprecipitation assays showed that the PDGF α-receptor analog secreted by the transfectants contained the PDGF α-receptor ligand-binding domain, the human heavy chain and the human light chain constant region. A clone that secreted a PDGF α-receptor analog that was positive for both the above-described ELISA assays and the immunoprecipitation assay was designated 5.6.2.1.

Example 16

Purification and characterization of PDGF α-Receptor Analogs

A. Purification of PDGF α-Receptor Analogs From Clone 3.17.1.57

The PDGF α-Receptor analog was purified from the conditioned culture media of clone 3.17.1.57 by cycling cell-conditioned medium over an immunoaffinity column composed of monoclonal antibody 292.18 bound to a CNBr-activated Sepharose 4B resin, which is specific for the PDGF α-receptor. The column was washed with PBA, then eluted with 0.1 M citrate, pH 3.0. The peak column fractions containing the α-receptor were pooled, neutralized to pH 7.2 by the addition of 2 M Tris, pH 7.4, then passed over a protein-A Sepharose column. This column was washed sequentially with PBS, then with 0.1 M citrate, pH 5.0. The PDGF α-receptor analog was then eluted with 0.1 M citrate, pH 3.0. The peak eluate fractions were pooled, and glycerol was added to a final concentration of lot. The sample was concentrated on a centriprep 10 concentrator (Amicon). The PDGF α-receptor analog purified from clone 3.17.1.57 was termed a "dimeric PDGF α-receptor analog".

B. Purification of PDGF α-Receptor Analogs From Clone 5.6.2.1

The PDGF α-receptor analog was purified from the conditioned culture media of clone 5.6.2.1 by cycling cell-conditioned medium over the immunoaffinity column described above. The column was washed with PBS then eluted with 0.1 M citrate, pH 3.0. The peak column fractions containing the α-receptor were pooled, neutralized to pH 7.2 by the addition of 2 M Tris (what pH 7.4), then passed over a protein-A sepharose column. This column was washed sequentially with PBS then with 0.1 M citrate, pH 5.0. The PDGF α-receptor analog was then eluted with 0.1 M citrate, pH 3.0. The peak eluate fractions were pooled and glycerol was added to a final concentration of 10%. The sample was concentrated on a centriprep 10 concentrator. The PDGF α-receptor analogs purified from clone 5.6.2.1 was termed a "tetrameric PDGF α-receptor analog".

Example 17

A. Use of the PDGF α-receptor Analogs in Ligand Binding Studies

Purified tetrameric PDGF α-receptor analog and purified dimeric PDGF α-receptor analog were compared to monolayers of a control cell line of canine kidney epithelial cells, which do not naturally express the PDGF α-receptor, transfected with the human PDGF α-receptor cDNA for ligand binding activity. The dissociation constant (Kd) of the receptor preparations was determined by saturation binding and subsequent Scatchard analysis.

Ligand binding of the purified PDGF α-receptor analogs was determined using a solid phase binding assay. Affinity-purified goat anti-human IgG was diluted to a concentration of 2 μg/ml in 0.1 M $Na_2HCO_3$, pH 9.6 and 100 μl/well of the solution was used to coat 96-well microtiter plates for 18 hours at 4° C. Excess antibody was removed from the wells with one wash with ELISA C buffer (PBS, 0.05% Tween-20). The plates were incubated with 175 μl/well of ELISA B buffer (PBS, 1% BSA, 0.05% Tween-20) to block the wells, followed by two washes with ELISA C buffer. One hundred microliters of 50 ng/ml PDGF α-receptor analog (dimeric or tetrameric) diluted in ELISA buffer B was added to each well and the plates were incubated over night at 4° C. Unbound protein was removed from the wells with two washes with ELISA buffer B. $^{125}$I-labeled PDGF-AA was serially diluted in binding media (Hams F-12, 25 mM HEPES pH 7.2, 0.25% rabbit serum albumin), and 100 μl of each dilution was added to the wells. The samples were incubated for two hours at room temperature. Unbound $^{125}$I-labeled PDGF-AA was removed with three washes with binding media. One hundred microliters of 0.1 M citrate, pH 2.5 was added to each well, and the plates were incubated for five minutes. After the incubation, the citrate buffer was removed and transferred to a tube for counting in a gamma counter. Nonspecific binding for each concentration of $^{125}$I-labeled PDGF-AA was determined by a parallel assay wherein separate wells coated only with goat anti-human IgG were incubated with the $^{125}$I-labeled PDGF-AA samples.

A saturation binding assay was performed on alpha T-7 cells transfected with the PDGF α-receptor. The cells were grown to confluency in 24-well culture plates. The cells were washed one time with binding media. Iodinated PDGF-AA was serially diluted in binding media. One milliliter of each dilution was added to the wells, and the plates were incubated for 3 hours at 4° C. Unbound $^{125}$I-labeled PDGF-AA was removed and the cells were washed three times with binding media. PBS containing 1% Triton X-100 was added to the cells for 5 minutes. The extracts were harvested and counted in a gamma counter. Nonspecific binding was determined at a single concentration of $^{125}$-labeled PDGF-AA using a 500-fold excess PDGF-BB.

The dissociation constants determined by Scatchard analysis (ibid.) of the saturation binding assays for the tetrameric PDGF α-receptor analog, dimeric PDGF α-receptor analog and the control cells (Table 5).

Table 5

Dissociation Constants for the Tetrameric PDGF α-Receptor, the Dimeric PDGF α-receptor and control cells Transfected with the PDGF α-receptor

TABLE 5

Dissociation Constants for the Tetrameric PDGF α-Receptor, the Dimeric PDGF α-receptor and control cells Transfected with the PDGF α-receptor

| Receptor | kD |
| --- | --- |
| Tetrameric PDGF α-receptor analog | $1.6 \times 10^{-11}$ |
| Dimeric PDGF α-receptor analog | $8.51 \times 10^{-11}$ |
| Control cells [PDGF α-receptor] | $3.7 \times 10^{-11}$ |

A solid-phase competition binding assay was established using the tetrameric PDGF α-receptor analog. Ninety six-well microtiter plates were coated with goat anti-human IgG (2 μg/ml), the wells blocked with ELISA B buffer, 50 ng/ml of purified tetrameric PDGF α-receptor analog diluted in binding media was added, and the plates were incubated two hours at room temperature. Unbound receptor was removed and the wells were washed with binding media. The plates were incubated for two hours at room temperature with increasing concentrations of either PDGF-AA or PDGF-BB diluted in binding media. The wells were washed, then incubated for two hours at room temperature with 3 ng/ml $^{125}$I-labeled PDGF-AA diluted in binding media. Unbound labeled PDGF-AA was removed, the wells were subsequently washed with binding media, and the bound, labeled PDGF-AA was harvested by the addition of 0.1 M citrate, pH 2.5, as described for the saturation binding studies. PDGF-AB, PDGF-AA and PDGF-BB were found to compete for receptor binding with $^{125}$I-PDGF-AA.

B. Use of Tetrameric PDGF α-Receptor Analogs As Antagonists for PDGF-Stimulated Mitogenesis.

A dimeric PDGF α-receptor analog, purified as described in Example 16.B., was analyzed for the ability to neutralize PDGF-stimulated mitogenesis in mouse 3T3 cells. Increasing amounts of the purified tetrameric PDGF α-receptor analog were mixed with PDGF-AA, -AB or -BB ranging 0.6 to 5 ng. The mixtures were then added to cultures of confluent mouse 3T3 cells. The ability of the PDGF to stimulate a mitogenic response, as measured by the incorporation of $^3$H-thymidine, was determined essentially as described (Raines and Ross, *Methods in Enzymology* 109: 749–773, 1985, which is incorporated by reference herein). The dimeric PDGF α-receptor analog demonstrated a dose response inhibition of PDGF-stimulated $^3$H-thymidine incorporation for all three isoforms of PDGF.

C. Inverse Ligand-Receptor Radioreceptor Assay

An inverse ligand-receptor radioreceptor assay was designed to screen for the presence of PDGF-BB, PDGF-BB binding proteins, PDGF-BB related molecules, and PDGF-β receptor antagonists in test samples. PDGF-BB (100 ng/ml) was coated onto the walls of 96-well microtiter plates, and the plates were incubated at 4° C. for 16 hours. The wells were washed once with ELISA C buffer and then incubated with ELISA B buffer to block the nonspecific binding sites. To the wells were added 50 µl of either PDGF standard or a test sample and 50 µl of $^{125}$I-labeled tetrameric PDGF β-receptor analog. The samples were incubated for one hour at room temperature. The wells were washed once with ELISA C buffer, and 0.1 M citrate, pH 2.5 containing 1% NP-40 was added to each well to disrupt the ligand-receptor analog bond and elute the bound receptor analog. The acid wash was collected and counted in a gamma counter. The presence of PDGF or a molecule which mimics PDGF or otherwise interferes with the binding of the well-bound PDGF-BB with its receptor will cause a decrease in the binding of the radiolabeled tetrameric PDGF β-receptor. Using this assay, PDGF-BB was found to inhibit receptor binding while PDGF-AA and PDGF-AB caused no significant decrease in receptor binding.

Example 18

Assay Methods

A. Preparation of Nitrocellulose Filters for Colony Assay

Colonies of transformants were tested for secretion of PDGF β-receptor analogs by first growing the cells on nitrocellulose filters that had been laid on top of solid growth medium. Nitrocellulose filters (Schleicher & Schuell, Keene, N.H.) were placed on top of solid growth medium and were allowed to be completely wetted. Test colonies were patched onto the wetted filters and were grown at 30° C. for approximately 40 hours. The filters were then removed from the solid medium, and the cells were removed by four successive rinses with Western Transfer Buffer (Table 4). The nitrocellulose filters were soaked in Western Buffer A (Table 4) for one hour at room temperature on a shaking platform with two changes of buffer. Secreted PDGFβ-R analogs were visualized on the filters described below.

B. Preparation of Protein Blot Filters

A nitrocellulose filter was soaked in Western Buffer A (Table 4) without the gelatin and placed in a Minifold (Schleicher & Schuell, Keene, N.H.). Five milliliters of culture supernatant was added without dilution to the Minifold wells, and the liquid was allowed to pass through the nitrocellulose filter by gravity. The nitrocellulose filter was removed from the minifold and was soaked in Western Buffer A (Table 3) for one hour on a shaking platform at room temperature. The buffer was changed three times during the hour incubation.

C. Preparation of Western Blot Filters

The transformants were analyzed by Western blot, essentially as described by Towbin et al. (*Proc. Natl. Acad. Sci. USA* 76: 4350–4354, 1979) and Gordon et al. (U.S. Pat. No. 4,452,901). Culture supernatants from appropriately grown transformants were diluted with three volumes of 95% ethanol. The ethanol mixtures were incubated overnight at −70° C. The precipitates were spun out of solution by centrifugation in an SS-24 rotor at 18,000 rpm for 20 minutes. The supernatants were discarded and the precipitate pellets were resuspended in 200 µl of dH$_2$O. Two hundred microliters of 2× loading buffer (Table 4) was added to each sample, and the samples were incubated in a boiling water bath for 5 minutes.

The samples were electrophoresed in a 15% sodium dodecylsulfate polyacrylamide gel under non-reducing conditions. The proteins were electrophoretically transferred to nitrocellulose paper using conditions described by Towbin et al. (ibid.). The nitrocellulose filters were then incubated in Western Buffer A (Table 4) for 75 minutes at room temperature on a platform rocker.

D. Processing the Filters for Visualization with Antibody

Filters prepared as described above were screened for proteins recognized by the binding of a PDGF β-receptor specific monoclonal antibody, designated PR7212. The filters were removed from the Western Buffer A (Table 4) and placed in sealed plastic bags containing a 10 ml solution comprising 10 µg/ml PR7212 monoclonal antibody diluted in Western Buffer A. The filters were incubated on a rocking platform overnight at 4° C. or for one hour at room temperature. Excess antibody was removed with three 15-minute washes with Western Buffer A on a shaking platform at room temperature.

Ten microliters biotin-conjugated horse anti-mouse antibody (Vector Laboratories, Burlingame, Calif.) in 20 ml Western Buffer A was added to the filters. The filters were re-incubated for one hour at room temperature on a platform shaker, and unbound conjugated antibody was removed with three fifteen-minute washes with Western Buffer A.

The filters were pre-incubated for one hour at room temperature with a solution comprising 50 µl Vectastain Reagent A (Vector Laboratories) in 10 ml of Western Buffer A that had been allowed to incubate at room temperature for 30 minutes before use. The filters were washed with one quick wash with distilled water followed by three 15-minute washes with Western Buffer B (Table 4) at room temperature. The Western Buffer B washes were followed by one wash with distilled water.

During the preceding wash step, the substrate reagent was prepared. Sixty mg of horseradish peroxidase reagent (Bio-Rad, Richmond, Calif.) was dissolved in 20 ml HPLC grade methanol. Ninety milliliters of distilled water was added to the dissolved peroxidase followed by 2.5 ml 2 M Tris, pH 7.4 and 3.8 ml 4 M NaCl. One hundred microliters of 30% H$_2$O$_2$ was added just before use. The washed filters were incubated with 75 ml of substrate and incubated at room temperature for 10 minutes with vigorous shaking. After the 10 minute incubation, the buffer was changed, and the filters were incubated for an additional 10 minutes. The filters were then washed in distilled water for one hour at room temperature. Positives were scored as those samples which exhibited coloration.

E. Processing the Filters For Visualization with an Anti-Substance P Antibody

Filters prepared as described above were probed with an anti-substance P antibody. The filters were removed from the Western Buffer A and rinsed with Western transfer buffer, followed by a 5-minute wash in phosphate buffered saline (PBS, Sigma, St. Louis, Mo.). The filters were incubated with a 10 ml solution containing 0.5 M 1-ethyl-3-3-dimethylamino propyl carbodiimide (Sigma) in 1.0 M NH$_4$Cl for 40 minutes at room temperature. After incubation, the filters were washed three times, for 5 minutes per wash, in PBS. The filters were blocked with 2% powdered milk diluted in PBS.

The filters were then incubated with a rat anti-substance P monoclonal antibody (Accurate Chemical & Scientific Corp., Westbury, N.Y.). Ten microliters of the antibody was diluted in 10 ml of antibody solution (PBS containing 20% fetal calf serum and 0.5% Tween-20). The filters were incubated at room temperature for 1 hour. Unbound antibody was removed with four 5-minute washes with PBS.

The filters were then incubated with a biotin-conjugated rabbit anti-rat peroxidase antibody (Cappel Laboratories, Melvern, Pa.). The conjugated antibody was diluted 1:1000 in 10 ml of antibody solution for 2 hours at room temperature. Excess conjugated antibody was removed with four 5-minute washes with PBS.

The filters were pre-incubated for 30 minutes at room temperature with a solution containing 50 µl Vectastain Reagent A (Vector Laboratories) and 50 µl Vectastain Reagent B (Vector Laboratories) in 10 ml of antibody solution that had been allowed to incubate for 30 minutes before use. Excess Vectastain reagents were removed by four 5-minute washes with PBS.

During the preceding wash step, the substrate reagent was prepared. Sixty milligrams of horseradish peroxidase reagent (Bio-Rad Laboratories, Richmond, Calif.) was dissolved in 25 ml of HPLC grade methanol. Approximately 100 ml of PBS and 200 µl $H_2O_2$ were added just before use. The filters were incubated with the substrate reagent for 10 to 20 minutes. The substrate was removed by a vigorous washing distilled water.

F. Iodination of PDGF-BB.

A PDGF-BB mutant molecule having a tyrosine replaing the phenylalanine at position 23 (PDGF-BB$_{Tyr}$) was iodinated and subsequently purified, using a purification method which produces 125I-labeled PDGF-BB with a higher specific activity than primary-labeled material and which was found to substantially derease the nonspecific binding component. The PDGF-BB$_{Tyr}$ was labeled using the Iodobead method (Pierce Chemical). The labeled protein was gel filtered over a C-25 desalting column (Pharmacia LKB Technologies) equilibrated with 10 mM acetic acid, 0.25% gelatin and 100 mM NaCl. The peak fractions were pooled and pH adjusted to 7.2 by the addition of Tris-base. The labeled mixture was chromatographed over an affinity column composed of PDGF β-receptor analog protein coupled to CnBr-activated Sepharose (Pharmacia LKB Technologies, Inc.). The column was washed with phosphate buffered saline and eluted with 0.1 M citrate, pH 2.5 containing 0.25% gelatin. The peak eluate fractions were pooled and assayed by ELISA to determine the PDGF-BB concentration.

Although the foregoing invention has been described in some detail by way of illustration and example for purposes of clarity of understanding, it will be evident that certain changes and modifications may be practiced within the scope of the appended claims.

We claim:

1. A biologically active, dimerized polypeptide fusion, comprising:
   first and second polypeptide chains, wherein each of said polypeptide chains comprises a non-immunoglobulin polypeptide requiring dimerization for biological activity joined to a dimerizing protein heterologous to said non-immunoglobulin polypeptide.

2. The biologically active, dimerized polypeptide fusion of claim 1 which is a homodimer.

3. The biologically active, dimerized polypeptide fusion of claim 1 wherein the dimerizing protein of one of said polypeptide chains comprises an immunoglobulin heavy chain constant region.

4. The biologically active, dimerized polypeptide fusion of claim 3 wherein the immunoglobulin heavy chain constant region is joined to an immunoglobulin hinge region.

5. The biologically active, dimerized polypeptide fusion of claim 3 wherein the immunoglobulin heavy chain constant region is joined to an immunoglobulin variable region.

6. The biologically active, dimerized polypeptide fusion of claim 5 wherein the immunoglobulin variable region is selected from the group consisting of $V_H$, Vκ, and Vλ.

7. The biologically active, dimerized polypeptide fusion of claim 1 wherein the dimerizing protein one of said polypeptide chains comprises an immunoglobulin heavy chain constant region domain selected from the group consisting of $C_H1$, $C_H2$, $C_H3$, and $C_H4$ of a γ, α, ε, μ, or δ class immunoglobulin heavy chain.

8. The biologically active, dimerized polypeptide fusion of claim 1 wherein the dimerizing protein of one of said polypeptide chains comprises an immunoglobulin light chain constant region.

9. A biologically active, multimerized polypeptide fusion, comprising:
   a non-immunoglobulin polypeptide requiring multimerization for biological activity joined to an immunoglobulin light chain constant region; and
   an immunoglobulin heavy chain constant region domain selected from the group consisting of $C_H1$, $C_H2$, $C_H3$, and $C_H4$.

10. The biologically active, multimerized polypeptide fusion of claim 9 which is a tetramer comprising four polypeptide fusions each having a non-immunoglobulin polypeptide joined to a multimerizing protein.

11. The biologically active, multimerized polypeptide fusion of claim 9 including a multimerizing protein which comprises an immunoglobulin heavy chain constant region domain selected from the group consisting of $C_H1$, $C_H2$, $C_H3$, and $C_H4$ of a γ, α, ε, μ, or δ class immunoglobulin heavy chain.

12. A biologically active, multimerized polypeptide fusion comprising: a non-immunoglobulin polypeptide requiring multimerization for biological activity joined to an immunoglobulin heavy chain constant region; and
   an immunoglobulin heavy chain.

13. The biologically active, multimerized polypeptide fusion of claim 12 wherein the immunoglobulin heavy chain constant region is joined to an immunoglobulin hinge region.

14. The biologically active, multimerized polypeptide fusion of claim 12 wherein the immunoglobulin heavy chain constant region is joined to an immunoglobulin variable region.

15. The biologically active, multimerized polypeptide fusion of claim 14 wherein the immunoglobulin variable region is selected from the group consisting of $V_H$, Vκ, and Vλ.

16. A biologically active, heteromultimeric polypeptide fusion, comprising:
   a first polypeptide fusion comprising a first non-immunoglobulin polypeptide joined to a first multimerizing protein heterologous to said first non-immunoglobulin polypeptide and a second polypeptide fusion comprising a second non-immunoglobulin polypeptide joined to a second multimerizing protein heterologous to said second non-immunoglobulin polypeptide, wherein said first multimerizing protein and said second multimerizing protein are capable of associating to form a multimer.

17. The biologically active, heteromultimeric polypeptide fusion of claim 16 wherein the first and second nonimmunoglobulin polypeptides each comprise an amino acid sequence selected from the group consisting of (A) the amino acid sequence Sequence ID NO:2, and (B) the amino acid sequence of Sequence ID NO:36.

18. The biologically active, heteromultimeric polypeptide fusion of claim 16 wherein the first multimerizing protein is different from the second multimerizing protein.

19. The biologically active, heteromultimeric polypeptide fusion of claim 18 wherein the first and second non-immunoglobulin polypeptides are the same.

20. The biologically active, heteromultimeric polypeptide fusion of claim 16 wherein the first and second multimerizing proteins each comprise an immunoglobulin heavy chain constant region or an immunoglobulin light chain constant region.

21. The biologically active, heteromultimeric polypeptide fusion of claim 16 which comprises a first polypeptide fusion having a first non-immunoglobulin polypeptide joined to a first immunoglobulin constant region and a second polypeptide fusion having a second non-immunoglobulin polypeptide fused to a second immunoglobulin constant region different from the first immunoglobulin constant region.

22. The biologically active, heteromultimeric polypeptide fusion of claim 21 wherein the first multimerizing protein comprises an immunoglobulin heavy chain constant region and the second multimerizing protein comprises an immunoglobulin light chain constant region.

23. The biologically active, heteromultimeric polypeptide fusion of claim 20 wherein one of said multimerizing proteins comprises an immunoglobulin heavy chain constant region joined to an immunoglobulin hinge region.

24. The biologically active, heteromultimeric polypeptide fusion of claim 20 wherein one of said multimerizing proteins comprises an immunoglobulin heavy chain constant region joined to an immunoglobulin variable region.

25. The biologically active, heteromultimeric polypeptide fusion of claim 24 wherein the immunoglobulin variable region is selected from the group consisting of $V_H$, $V\kappa$, and $V\lambda$.

26. The biologically active, heteromultimeric polypeptide fusion of claim 16 wherein one of said multimerizing proteins comprises an immunoglobulin heavy chain constant region domain selected from the group consisting of $C_H1$, $C_H2$, $C_H3$, and $C_H4$ of a $\gamma$, $\alpha$, $\epsilon$, $\mu$, or $\delta$ class immunoglobulin heavy chain.

27. The biologically active, heteromultimeric polypeptide fusion of claim 16 wherein said multimerized polypeptide fusion comprises a first polypeptide fusion comprising a first receptor or receptor domain requiring multimerization for activity joined to a first immunoglobulin constant region and a second polypeptide fusion comprising a second receptor or receptor domain requiring multimerization for activity joined to a second immunoglobulin constant region.

28. The biologically active, heteromultimeric polypeptide fusion of claim 27 wherein one of said receptor domains comprises a ligand binding domain.

29. The biologically active, heteromultimeric polypeptide fusion of claim 16 which is a heterotetramer comprising four polypeptide fusions each having a non-immunoglobulin polypeptide joined to a multimerizing protein.

* * * * *

UNITED STATES PATENT AND TRADEMARK OFFICE
CERTIFICATE OF CORRECTION

PATENT NO.   : 6,018,026
DATED        : January 25, 2000
INVENTOR(S)  : Sledziewski et al.

It is certified that error appears in the above-identified patent and that said Letters Patent is hereby corrected as shown below:

<u>Column 100,</u>
Line 42, delete "heavy" and insert therefor -- light --.

Signed and Sealed this

Thirtieth Day of July, 2002

*Attest:*

*Attesting Officer*

JAMES E. ROGAN
*Director of the United States Patent and Trademark Office*

(12) EX PARTE REEXAMINATION CERTIFICATE (5438th)
United States Patent
Sledziewski et al.

(10) Number: US 6,018,026 C1
(45) Certificate Issued: *Jul. 4, 2006

(54) BIOLOGICALLY ACTIVE DIMERIZED AND MULTIMERIZED POLYPEPTIDE FUSIONS

(75) Inventors: Andrzej Z. Sledziewski, Seattle, WA (US); Lillian Anne Bell, Seattle, WA (US); Wayne R. Kindsvogel, Seattle, WA (US)

(73) Assignee: ZymoGenetics, Inc., Seattle, WA (US)

Reexamination Request:
No. 90/006,971, Mar. 16, 2004

Reexamination Certificate for:
Patent No.: 6,018,026
Issued: Jan. 25, 2000
Appl. No.: 08/980,400
Filed: Nov. 26, 1997

(*) Notice: This patent is subject to a terminal disclaimer.

Certificate of Correction issued Jul. 13, 2002.

Related U.S. Application Data

(60) Division of application No. 08/477,329, filed on Jun. 7, 1995, now Pat. No. 5,750,375, which is a continuation of application No. 08/180,195, filed on Jan. 11, 1994, now Pat. No. 5,567,584, which is a continuation of application No. 07/634,510, filed on Dec. 27, 1990, now abandoned, which is a continuation-in-part of application No. 07/347,291, filed on May 2, 1989, now Pat. No. 5,155,027, which is a continuation-in-part of application No. 07/146,877, filed on Jan. 22, 1988, now abandoned.

(51) Int. Cl.
C07K 19/00 (2006.01)
C07K 16/46 (2006.01)
C07K 14/71 (2006.01)

(52) U.S. Cl. ............... 530/350; 530/387.3; 530/388.24; 530/399; 530/402

(58) Field of Classification Search ............... 530/350, 530/387.3, 388.24, 399, 402; 435/69.7
See application file for complete search history.

(56) References Cited

U.S. PATENT DOCUMENTS

| | | | |
|---|---|---|---|
| 4,859,609 A | 8/1989 | Dull et al. | 436/501 |
| 5,098,833 A | 3/1992 | Lasky et al. | 435/69.1 |
| 5,336,603 A | 8/1994 | Capon et al. | 435/69.7 |
| 5,428,130 A | 6/1995 | Capon et al. | 530/350 |
| 5,565,335 A | 10/1996 | Capon et al. | 435/64.7 |
| 5,605,690 A | 2/1997 | Jacobs et al. | 424/134.1 |
| 5,610,279 A | 3/1997 | Brockhaus et al. | 530/387.3 |
| 5,648,260 A | 7/1997 | Winter et al. | 435/252.3 |
| 5,650,150 A | 7/1997 | Gillies | 424/134.1 |
| 5,712,155 A | 1/1998 | Smith et al. | 435/320.1 |
| 5,726,037 A | 3/1998 | Bodary et al. | 435/69.1 |
| 6,004,781 A | 12/1999 | Seed | 435/69.7 |
| 6,018,026 A | 1/2000 | Sledziewski et al. | 530/350 |

OTHER PUBLICATIONS

Bierer, Barbara E., et al., "The Biologic Roles of CD2, CD4, and CD8 in T-cell Activation", *Ann. Rev. Immunol.*, vol. 7, (1989), 579–599.

Ellis, Leland, et al., "Truncation of the Ectodomian of the Human Insulin Receptor Results in Secretion of a Soluble Insulin Binding Protein from Transfected CHO Cells", *Journal of Molecular Recognition*, vol. 1, No. 1, (1988),25–31.

Estess, Mark D., et al., "Analysis of T–Cell Receptor Structure and Function Using Chimeric T–Cell Receptor/Immunoglobulin Molecules", *J. Cell Biochem. Suppl. O* (11 part D), (1987),258.

Fernley, R. T., et al., "The Application of Recombinant DNA Techniques to the Study of Cell Membrane Receptors", *Molecular and Chemical Characterization of Membrane Receptors*, (1984),261–282.

Gascoigne, Nicholas R., et al., "Chimeric Proteins Produced By T Cell Receptor–Immunoglobulin Gene Fusions", *Immune Regulation by Characterized Polypeptides*, (1987), 617–627.

Gascoigne, Nicholas R., et al., "Secretion of Chimeric T Cell Receptor–Immunoglobulin Fushion Proteins", *J. Cell Biochem. Suppl. O* (11 part D), (1987),259.

Goverman, Joan, et al., "Chimeric T–Cell Receptor Genes as Tools in Analyzing T–Cell/Target–Cell Interactions", *J. Cell Biochem. Suppl. O* (11 part D), (1987),259.

Himmler, Adolf, et al., "Molecular Cloning and Expression of Human and Rat Tumor Necrosis Factor Receptor Chain (p. 60) and Its Soluble Derivative, Tumor Necrosis Factor–Binding Protein", *DNA and Cell Biology*, vol. 9, No. 10, (1990),705–715.

Ratnofsky, Sheldon E., et al., "Expression and Function of CD8 in a Murine T Cell Hybridoma", *J. Exp. Med.*, vol. 166, (Dec. 1987),1747–1757.

Smith, Richard A., et al., "Multimeric Structure of the Tumor Necrosis Factor Receptor of HeLa Cells", *Journal of Biological Chemistry*, vol. 264, No. 25, (Sep. 5, 1989), 14646–14652.

Traunecker, Andre, et al., "Highly Efficient Neutralization of HIV with Recombinant CD4–immunoglobulin molecules", *Nature*, vol. 339, (May 4, 1989),68–70.

Traunecker, Andre, et al., "Solubilizing the T–cell receptor—problems in solution", *Immunology Today*, vol. 10, (1989),29–32.

(Continued)

*Primary Examiner*—Prema Mertz

(57) ABSTRACT

Methods for producing secreted receptor analogs and biologically active peptide dimers are disclosed. The methods for producing secreted receptor analogs and biologically active peptide dimers utilize a DNA sequence encoding a receptor analog or a peptide requiring dimerization for biological activity joined to a dimerizing protein. The receptor analog includes a ligand-binding domain. Polypeptides comprising essentially the extracellular domain of a human PDGF receptor fused to dimerizing proteins, the portion being capable of binding human PDGF or an isoform thereof, are also disclosed. The polypeptides may be used within methods for determining the presence of and for purifying human PDGF or isoforms thereof.

OTHER PUBLICATIONS

Ullrich, Axel, et al., "Signal Transduction by Receptors with Tyrosine Kinase Activity", *Cell,* vol. 61, (1990),203–212.

Van Brunt, Jennifer, "Lymphokine Receptors as Therapeutics", *Bio/Technology,* vol. 7, (Jul., 1989),668–669.

Weber, David V., et al., "Medium–Scale Ligand–Affinity Purification of Two Soluble Forms of Human Interleukin–2 Receptor", *Journal of Chromatography,* vol. 431, (1988), 55–63.

Whittaker, Jonathan, et al., "Secretion of Soluble Functional Insulin Receptors by Transfected NIH3T3 Cells", *Journal of Biological Chemistry,* vol. 263, No. 7, (Mar. 5, 1988), 3063–3066.

Williams, Gareth T., et al., "Signal Transduction by Receptors with Tyrosine Kinase Activity", *Gene,* vol. 43, (1986), 319–324.

Williams, Alan F., et al., "The Immunoglobulin Superfamily—Domains for Cell Surface Recognition", *Ann. Rev. Immunol,* vol. 6, (1988),381–405.

Ellis, Leland, et al., "Linking functional domains of the human insulin receptor with the bacterial aspartate receptor", *Proc. Natl. Acad. Sci. USA,* vol. 83, (Nov. 1986), pp. 8137–8141.

Gascoigne, Nicholas R., et al., "Secretion of chimeric T–cell receptor–immunoglobulin protein", *Proc. Natl. Acad. Sci.,* vol. 84, (May 1987), pp. 2936–2940.

Riedel, Heimo, et al., "A chimeric, ligand–binding v–erbB/EGF receptor retains transforming potential", *Science,* vol. 236,(Apr. 10, 1987), pp. 197–200.

Traunecker, Andre, et al., "Soluble CD4 molecules neutralize human immunodeficiency virus type 1", *Nature,* vol. 331,(Jan. 1988), pp. 84–86.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 9–11 and 13–29 is confirmed.

Claims 1, 7 and 12 are determined to be patentable as amended.

Claims 2–6 and 8, dependent on an amended claim, are determined to be patentable.

New claim 30 is added and determined to be patentable.

1. A biologically active, dimerized polypeptide fusion, comprising:
    first and second polypeptide chains, wherein each of said polypeptide chains comprises a non-immunoglobulin polypeptide requiring dimerization for biological activity joined to a dimerizing protein heterologous to said non-immunoglobulin polypeptide, *wherein the dimerizing protein is selected from the group consisting of yeast invertase, at least a portion of an immunoglobulin light chain comprising at least an immunoglobulin light chain constant region domain, and at least a portion of an immunoglobulin heavy chain comprising at least an immunoglobulin heavy chain constant region domain.*

7. The biologically active, dimerized polypeptide fusion of claim 1 wherein the dimerizing protein *of* one of said polypeptide chains comprises an immunoglobulin heavy chain constant region domain selected from the group consisting of $C_H1$, $C_H2$, $C_H3$, and $C_H4$ of a γ, α, ε, μ, or δ class immunoglobulin heavy chain.

12. A biologically active, multimerized polypeptide fusion comprising: a non-immunoglobulin polypeptide requiring multimerization for biological activity joined to an immunoglobulin heavy chain constant region; and
    an immunoglobulin light chain.

*30. The polypeptide fusion of claim 1 wherein the dimerizing protein is at least a portion of an immunoglobulin heavy chain comprising an immunoglobulin heavy chain constant region domain joined to an immunoglobulin heavy chain hinge region.*

* * * * *

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 4465 base pairs
      (B) TYPE: nucleic acid
      (C) STRANDEDNESS: double
      (D) TOPOLOGY: linear (ii) MOLECULE TYPE: cDNA (iii) HYPOTHETICAL: N (iv) ANTI-SENSE: N (vi) ORIGINAL SOURCE:
      (A) ORGANISM: Homo sapiens
      (D) DEVELOPMENTAL STAGE: Adult
      (F) TISSUE TYPE: Skin
      (G) CELL TYPE: fibroblasts (vii) IMMEDIATE SOURCE:
      (B) CLONE: pR-rX1

(ix) FEATURE:
      (A) NAME/KEY: CDS
      (B) LOCATION: 354..3671
      (D) OTHER INFORMATION:

(xi) SEQUENCE DESCRIPTION: SEQ ID NO:1:

```
CCCTCAGCCC TGCTGCCCAG CACGAGCCTG TGCTCGCCCT GCCCAACGCA GACAGCCAGA        60

CCCAGGGCGG CCCCTCTGGC GGCTCTGCTC CTCCCGAAGG ATGCTTGGGG AGTGAGGCGA       120

AGCTGGGCGC TCCTCTCCCC TACAGCAGCC CCCTTCCTCC ATCCCTCTGT TCTCCTGAGC       180
```

```
CTTCAGGAGC CTGCACCAGT CCTGCCTGTC CTTCTACTCA GCTGTTACCC ACTCTGGGAC      240

CAGCAGTCTT TCTGATAACT GGGAGAGGGC AGTAAGGAGG ACTTCCTGGA GGGGGTGACT      300

GTCCAGAGCC TGGAACTGTG CCCACACCAG AAGCCATCAG CAGCAAGGAC ACC ATG         356
                                                          Met
                                                          1

CGG CTT CCG GGT GCG ATG CCA GCT CTG GCC CTC AAA GGC GAG CTG CTG        404
Arg Leu Pro Gly Ala Met Pro Ala Leu Ala Leu Lys Gly Glu Leu Leu
            5               10                  15

TTG CTG TCT CTC CTG TTA CTT CTG GAA CCA CAG ATC TCT CAG GGC CTG        452
Leu Leu Ser Leu Leu Leu Leu Leu Glu Pro Gln Ile Ser Gln Gly Leu
        20              25                  30

GTC GTC ACA CCC CCG GGG CCA GAG CTT GTC CTC AAT GTC TCC AGC ACC        500
Val Val Thr Pro Pro Gly Pro Glu Leu Val Leu Asn Val Ser Ser Thr
    35              40                  45

TTC GTT CTG ACC TGC TCG GGT TCA GCT CCG GTG GTG TGG GAA CGG ATG        548
Phe Val Leu Thr Cys Ser Gly Ser Ala Pro Val Val Trp Glu Arg Met
50              55                  60                  65

TCC CAG GAG CCC CCA CAG GAA ATG GCC AAG GCC CAG GAT GGC ACC TTC        596
Ser Gln Glu Pro Pro Gln Glu Met Ala Lys Ala Gln Asp Gly Thr Phe
                70                  75                  80

TCC AGC GTG CTC ACA CTG ACC AAC CTC ACT GGG CTA GAC ACG GGA GAA        644
Ser Ser Val Leu Thr Leu Thr Asn Leu Thr Gly Leu Asp Thr Gly Glu
            85                  90                  95

TAC TTT TGC ACC CAC AAT GAC TCC CGT GGA CTG GAG ACC GAT GAG CGG        692
Tyr Phe Cys Thr His Asn Asp Ser Arg Gly Leu Glu Thr Asp Glu Arg
        100                 105                 110

AAA CGG CTC TAC ATC TTT GTG CCA GAT CCC ACC GTG GGC TTC CTC CCT        740
Lys Arg Leu Tyr Ile Phe Val Pro Asp Pro Thr Val Gly Phe Leu Pro
    115                 120                 125

AAT GAT GCC GAG GAA CTA TTC ATC TTT CTC ACG GAA ATA ACT GAG ATC        788
Asn Asp Ala Glu Glu Leu Phe Ile Phe Leu Thr Glu Ile Thr Glu Ile
130                 135                 140                 145

ACC ATT CCA TGC CGA GTA ACA GAC CCA CAG CTG GTG GTG ACA CTG CAC        836
Thr Ile Pro Cys Arg Val Thr Asp Pro Gln Leu Val Val Thr Leu His
                150                 155                 160

GAG AAG AAA GGG GAC GTT GCA CTG CCT GTC CCC TAT GAT CAC CAA CGT        884
Glu Lys Lys Gly Asp Val Ala Leu Pro Val Pro Tyr Asp His Gln Arg
            165                 170                 175

GGC TTT TCT GGT ATC TTT GAG GAC AGA AGC TAC ATC TGC AAA ACC ACC        932
Gly Phe Ser Gly Ile Phe Glu Asp Arg Ser Tyr Ile Cys Lys Thr Thr
        180                 185                 190

ATT GGG GAC AGG GAG GTG GAT TCT GAT GCC TAC TAT GTC TAC AGA CTC        980
Ile Gly Asp Arg Glu Val Asp Ser Asp Ala Tyr Tyr Val Tyr Arg Leu
    195                 200                 205

CAG GTG TCA TCC ATC AAC GTC TCT GTG AAC GCA GTG CAG ACT GTG GTC       1028
Gln Val Ser Ser Ile Asn Val Ser Val Asn Ala Val Gln Thr Val Val
210                 215                 220                 225

CGC CAG GGT GAG AAC ATC ACC CTC ATG TGC ATT GTG ATC GGG AAT GAG       1076
Arg Gln Gly Glu Asn Ile Thr Leu Met Cys Ile Val Ile Gly Asn Glu
                230                 235                 240

GTG GTC AAC TTC GAG TGG ACA TAC CCC CGC AAA GAA AGT GGG CGG CTG       1124
Val Val Asn Phe Glu Trp Thr Tyr Pro Arg Lys Glu Ser Gly Arg Leu
            245                 250                 255

GTG GAG CCG GTG ACT GAC TTC CTC TTG GAT ATG CCT TAC CAC ATC CGC       1172
Val Glu Pro Val Thr Asp Phe Leu Leu Asp Met Pro Tyr His Ile Arg
        260                 265                 270

TCC ATC CTG CAC ATC CCC AGT GCC GAG TTA GAA GAC TCG GGA ACC TAC       1220
Ser Ile Leu His Ile Pro Ser Ala Glu Leu Glu Asp Ser Gly Thr Tyr
    275                 280                 285
```

```
ACC TGC AAT GTG ACG GAG AGT GTG AAT GAC CAT CAG GAT GAA AAG GCC         1268
Thr Cys Asn Val Thr Glu Ser Val Asn Asp His Gln Asp Glu Lys Ala
290                 295                 300                 305

ATC AAC ATC ACC GTG GTT GAG AGC GGC TAC GTG CGG CTC CTG GGA GAG         1316
Ile Asn Ile Thr Val Val Glu Ser Gly Tyr Val Arg Leu Leu Gly Glu
                310                 315                 320

GTG GGC ACA CTA CAA TTT GCT GAG CTG CAT CGG AGC CGG ACA CTG CAG         1364
Val Gly Thr Leu Gln Phe Ala Glu Leu His Arg Ser Arg Thr Leu Gln
            325                 330                 335

GTA GTG TTC GAG GCC TAC CCA CCG CCC ACT GTC CTG TGG TTC AAA GAC         1412
Val Val Phe Glu Ala Tyr Pro Pro Pro Thr Val Leu Trp Phe Lys Asp
        340                 345                 350

AAC CGC ACC CTG GGC GAC TCC AGC GCT GGC GAA ATC GCC CTG TCC ACG         1460
Asn Arg Thr Leu Gly Asp Ser Ser Ala Gly Glu Ile Ala Leu Ser Thr
355                 360                 365

CGC AAC GTG TCG GAG ACC CGG TAT GTG TCA GAG CTG ACA CTG GTT CGC         1508
Arg Asn Val Ser Glu Thr Arg Tyr Val Ser Glu Leu Thr Leu Val Arg
370                 375                 380                 385

GTG AAG GTG GCA GAG GCT GGC CAC TAC ACC ATG CGG GCC TTC CAT GAG         1556
Val Lys Val Ala Glu Ala Gly His Tyr Thr Met Arg Ala Phe His Glu
                390                 395                 400

GAT GCT GAG GTC CAG CTC TCC TTC CAG CTA CAG ATC AAT GTC CCT GTC         1604
Asp Ala Glu Val Gln Leu Ser Phe Gln Leu Gln Ile Asn Val Pro Val
            405                 410                 415

CGA GTG CTG GAG CTA AGT GAG AGC CAC CCT GAC AGT GGG GAA CAG ACA         1652
Arg Val Leu Glu Leu Ser Glu Ser His Pro Asp Ser Gly Glu Gln Thr
        420                 425                 430

GTC CGC TGT CGT GGC CGG GGC ATG CCC CAG CCG AAC ATC ATC TGG TCT         1700
Val Arg Cys Arg Gly Arg Gly Met Pro Gln Pro Asn Ile Ile Trp Ser
    435                 440                 445

GCC TGC AGA GAC CTC AAA AGG TGT CCA CGT GAG CTG CCG CCC ACG CTG         1748
Ala Cys Arg Asp Leu Lys Arg Cys Pro Arg Glu Leu Pro Pro Thr Leu
450                 455                 460                 465

CTG GGG AAC AGT TCC GAA GAG GAG AGC CAG CTG GAG ACT AAC GTG ACG         1796
Leu Gly Asn Ser Ser Glu Glu Glu Ser Gln Leu Glu Thr Asn Val Thr
                470                 475                 480

TAC TGG GAG GAG GAG CAG GAG TTT GAG GTG GTG AGC ACA CTG CGT CTG         1844
Tyr Trp Glu Glu Glu Gln Glu Phe Glu Val Val Ser Thr Leu Arg Leu
            485                 490                 495

CAG CAC GTG GAT CGG CCA CTG TCG GTG CGC TGC ACG CTG CGC AAC GCT         1892
Gln His Val Asp Arg Pro Leu Ser Val Arg Cys Thr Leu Arg Asn Ala
        500                 505                 510

GTG GGC CAG GAC ACG CAG GAG GTC ATC GTG GTG CCA CAC TCC TTG CCC         1940
Val Gly Gln Asp Thr Gln Glu Val Ile Val Val Pro His Ser Leu Pro
515                 520                 525

TTT AAG GTG GTG GTG ATC TCA GCC ATC CTG GCC CTG GTG GTG CTC ACC         1988
Phe Lys Val Val Val Ile Ser Ala Ile Leu Ala Leu Val Val Leu Thr
530                 535                 540                 545

ATC ATC TCC CTT ATC ATC CTC ATC ATG CTT TGG CAG AAG AAG CCA CGT         2036
Ile Ile Ser Leu Ile Ile Leu Ile Met Leu Trp Gln Lys Lys Pro Arg
                550                 555                 560

TAC GAG ATC CGA TGG AAG GTG ATT GAG TCT GTG AGC TCT GAC GGC CAT         2084
Tyr Glu Ile Arg Trp Lys Val Ile Glu Ser Val Ser Ser Asp Gly His
            565                 570                 575

GAG TAC ATC TAC GTG GAC CCC ATG CAG CTG CCC TAT GAC TCC ACG TGG         2132
Glu Tyr Ile Tyr Val Asp Pro Met Gln Leu Pro Tyr Asp Ser Thr Trp
        580                 585                 590

GAG CTG CCG CGG GAC CAG CTT GTG CTG GGA CGC ACC CTC GGC TCT GGG         2180
Glu Leu Pro Arg Asp Gln Leu Val Leu Gly Arg Thr Leu Gly Ser Gly
    595                 600                 605
```

-continued

| | | | | | | | | | | | | | | |
|---|---|---|---|---|---|---|---|---|---|---|---|---|---|---|
| GCC | TTT | GGG | CAG | GTG | GTG | GAG | GCC | ACG | GCT | CAT | GGC | CTG | AGC | CAT | TCT | 2228 |
| Ala | Phe | Gly | Gln | Val | Val | Glu | Ala | Thr | Ala | His | Gly | Leu | Ser | His | Ser |
| 610 | | | | 615 | | | | | 620 | | | | | 625 |

```
GCC TTT GGG CAG GTG GTG GAG GCC ACG GCT CAT GGC CTG AGC CAT TCT                    2228
Ala Phe Gly Gln Val Val Glu Ala Thr Ala His Gly Leu Ser His Ser
610             615                 620                 625

CAG GCC ACG ATG AAA GTG GCC GTC AAG ATG CTT AAA TCC ACA GCC CGC                    2276
Gln Ala Thr Met Lys Val Ala Val Lys Met Leu Lys Ser Thr Ala Arg
                630                 635                 640

AGC AGT GAG AAG CAA GCC CTT ATG TCG GAG CTG AAG ATC ATG AGT CAC                    2324
Ser Ser Glu Lys Gln Ala Leu Met Ser Glu Leu Lys Ile Met Ser His
            645                 650                 655

CTT GGG CCC CAC CTG AAC GTG GTC AAC CTG TTG GGG GCC TGC ACC AAA                    2372
Leu Gly Pro His Leu Asn Val Val Asn Leu Leu Gly Ala Cys Thr Lys
        660                 665                 670

GGA GGA CCC ATC TAT ATC ATC ACT GAG TAC TGC CGC TAC GGA GAC CTG                    2420
Gly Gly Pro Ile Tyr Ile Ile Thr Glu Tyr Cys Arg Tyr Gly Asp Leu
    675                 680                 685

GTG GAC TAC CTG CAC CGC AAC AAA CAC ACC TTC CTG CAG CAC CAC TCC                    2468
Val Asp Tyr Leu His Arg Asn Lys His Thr Phe Leu Gln His His Ser
690                 695                 700                 705

GAC AAG CGC CGC CCG CCC AGC GCG GAG CTC TAC AGC AAT GCT CTG CCC                    2516
Asp Lys Arg Arg Pro Pro Ser Ala Glu Leu Tyr Ser Asn Ala Leu Pro
                710                 715                 720

GTT GGG CTC CCC CTG CCC AGC CAT GTG TCC TTG ACC GGG GAG AGC GAC                    2564
Val Gly Leu Pro Leu Pro Ser His Val Ser Leu Thr Gly Glu Ser Asp
            725                 730                 735

GGT GGC TAC ATG GAC ATG AGC AAG GAC GAG TCG GTG GAC TAT GTG CCC                    2612
Gly Gly Tyr Met Asp Met Ser Lys Asp Glu Ser Val Asp Tyr Val Pro
        740                 745                 750

ATG CTG GAC ATG AAA GGA GAC GTC AAA TAT GCA GAC ATC GAG TCC TCC                    2660
Met Leu Asp Met Lys Gly Asp Val Lys Tyr Ala Asp Ile Glu Ser Ser
    755                 760                 765

AAC TAC ATG GCC CCT TAC GAT AAC TAC GTT CCC TCT GCC CCT GAG AGG                    2708
Asn Tyr Met Ala Pro Tyr Asp Asn Tyr Val Pro Ser Ala Pro Glu Arg
770                 775                 780                 785

ACC TGC CGA GCA ACT TTG ATC AAC GAG TCT CCA GTG CTA AGC TAC ATG                    2756
Thr Cys Arg Ala Thr Leu Ile Asn Glu Ser Pro Val Leu Ser Tyr Met
                790                 795                 800

GAC CTC GTG GGC TTC AGC TAC CAG GTG GCC AAT GGC ATG GAG TTT CTG                    2804
Asp Leu Val Gly Phe Ser Tyr Gln Val Ala Asn Gly Met Glu Phe Leu
            805                 810                 815

GCC TCC AAG AAC TGC GTC CAC AGA GAC CTG GCG GCT AGG AAC GTG CTC                    2852
Ala Ser Lys Asn Cys Val His Arg Asp Leu Ala Ala Arg Asn Val Leu
        820                 825                 830

ATC TGT GAA GGC AAG CTG GTC AAG ATC TGT GAC TTT GGC CTG GCT CGA                    2900
Ile Cys Glu Gly Lys Leu Val Lys Ile Cys Asp Phe Gly Leu Ala Arg
    835                 840                 845

GAC ATC ATG CGG GAC TCG AAT TAC ATC TCC AAA GGC AGC ACC TTT TTG                    2948
Asp Ile Met Arg Asp Ser Asn Tyr Ile Ser Lys Gly Ser Thr Phe Leu
850                 855                 860                 865

CCT TTA AAG TGG ATG GCT CCG GAG AGC ATC TTC AAC AGC CTC TAC ACC                    2996
Pro Leu Lys Trp Met Ala Pro Glu Ser Ile Phe Asn Ser Leu Tyr Thr
                870                 875                 880

ACC CTG AGC GAC GTG TGG TCC TTC GGG ATC CTG CTC TGG GAG ATC TTC                    3044
Thr Leu Ser Asp Val Trp Ser Phe Gly Ile Leu Leu Trp Glu Ile Phe
            885                 890                 895

ACC TTG GGT GGC ACC CCT TAC CCA GAG CTG CCC ATG AAC GAG CAG TTC                    3092
Thr Leu Gly Gly Thr Pro Tyr Pro Glu Leu Pro Met Asn Glu Gln Phe
        900                 905                 910

TAC AAT GCC ATC AAA CGG GGT TAC CGC ATG GCC CAG CCT GCC CAT GCC                    3140
Tyr Asn Ala Ile Lys Arg Gly Tyr Arg Met Ala Gln Pro Ala His Ala
    915                 920                 925
```

```
TCC GAC GAG ATC TAT GAG ATC ATG CAG AAG TGC TGG GAA GAG AAG TTT          3188
Ser Asp Glu Ile Tyr Glu Ile Met Gln Lys Cys Trp Glu Glu Lys Phe
930                 935                 940                 945

GAG ATT CGG CCC CCC TTC TCC CAG CTG GTG CTG CTT CTC GAG AGA CTG          3236
Glu Ile Arg Pro Pro Phe Ser Gln Leu Val Leu Leu Leu Glu Arg Leu
            950                 955                 960

TTG GGC GAA GGT TAC AAA AAG AAG TAC CAG CAG GTG GAT GAG GAG TTT          3284
Leu Gly Glu Gly Tyr Lys Lys Lys Tyr Gln Gln Val Asp Glu Glu Phe
                965                 970                 975

CTG AGG AGT GAC CAC CCA GCC ATC CTT CGG TCC CAG GCC CGC TTG CCT          3332
Leu Arg Ser Asp His Pro Ala Ile Leu Arg Ser Gln Ala Arg Leu Pro
            980                 985                 990

GGG TTC CAT GGC CTC CGA TCT CCC CTG GAC ACC AGC TCC GTC CTC TAT          3380
Gly Phe His Gly Leu Arg Ser Pro Leu Asp Thr Ser Ser Val Leu Tyr
    995                 1000                1005

ACT GCC GTG CAG CCC AAT GAG GGT GAC AAC GAC TAT ATC ATC CCC CTG          3428
Thr Ala Val Gln Pro Asn Glu Gly Asp Asn Asp Tyr Ile Ile Pro Leu
1010                1015                1020                1025

CCT GAC CCC AAA CCC GAG GTT GCT GAC GAG GGC CCA CTG GAG GGT TCC          3476
Pro Asp Pro Lys Pro Glu Val Ala Asp Glu Gly Pro Leu Glu Gly Ser
                1030                1035                1040

CCC AGC CTA GCC AGC TCC ACC CTG AAT GAA GTC AAC ACC TCC TCA ACC          3524
Pro Ser Leu Ala Ser Ser Thr Leu Asn Glu Val Asn Thr Ser Ser Thr
            1045                1050                1055

ATC TCC TGT GAC AGC CCC CTG GAG CCC CAG GAC GAA CCA GAG CCA GAG          3572
Ile Ser Cys Asp Ser Pro Leu Glu Pro Gln Asp Glu Pro Glu Pro Glu
                1060                1065                1070

CCC CAG CTT GAG CTC CAG GTG GAG CCG GAG CCA GAG CTG GAA CAG TTG          3620
Pro Gln Leu Glu Leu Gln Val Glu Pro Glu Pro Glu Leu Glu Gln Leu
1075                1080                1085

CCG GAT TCG GGG TGC CCT GCG CCT CGG GCG GAA GCA GAG GAT AGC TTC          3668
Pro Asp Ser Gly Cys Pro Ala Pro Arg Ala Glu Ala Glu Asp Ser Phe
1090                1095                1100                1105

CTG TAGGGGCTG GCCCCTACCC TGCCCTGCCT GAAGCTCCCC CCCTGCCAGC                3721
Leu

ACCCAGCATC TCCTGGCCTG GCCTGACCGG GCTTCCTGTC AGCCAGGCTG CCCTTATCAG        3781

CTGTCCCCTT CTGGAAGCTT TCTGCTCCTG ACGTGTTGTG CCCCAAACCC TGGGGCTGGC        3841

TTAGGAGGCA AGAAAACTGC AGGGGCCGTG ACCAGCCCTC TGCCTCCAGG GAGGCCAACT        3901

GACTCTGAGC CAGGGTTCCC CCAGGGAACT CAGTTTTCCC ATATGTAAGA TGGGAAAGTT       3961

AGGCTTGATG ACCCAGAATC TAGGATTCTC TCCCTGGCTG ACACGGTGGG GAGACCGAAT       4021

CCCTCCCTGG AAGATTCTT GGAGTTACTG AGGTGGTAAA TTAACATTTT TTCTGTTCAG        4081

CCAGCTACCC CTCAAGGAAT CATAGCTCTC TCCTCGCACT TTTTATCCAC CCAGGAGCTA       4141

GGGAAGAGAC CCTAGCCTCC CTGGCTGCTG GCTGAGCTAG GGCCTAGCTT GAGCAGTGTT       4201

GCCTCATCCA GAAGAAAGCC AGTCTCCTCC CTATGATGCC AGTCCCTGCG TTCCCTGGCC       4261

CGAGCTGGTC TGGGGCCATT AGGCAGCCTA ATTAATGCTG GAGGCTGAGC CAAGTACAGG       4321

ACACCCCCAG CCTGCAGCCC TTGCCCAGGG CACTTGGAGC ACACGCAGCC ATAGCAAGTG       4381

CCTGTGTCCC TGTCCTTCAG GCCCATCAGT CCTGGGGCTT TTTCTTTATC ACCCTCAGTC       4441

TTAATCCATC CACCAGAGTC TAGA                                              4465

(2) INFORMATION FOR SEQ ID NO:2:

(i) SEQUENCE CHARACTERISTICS:
            (A) LENGTH: 1106 amino acids
            (B) TYPE: amino acid
            (D) TOPOLOGY: linear
```

(ii) MOLECULE TYPE: protein (xi) SEQUENCE DESCRIPTION: SEQ ID NO:2:

```
Met Arg Leu Pro Gly Ala Met Pro Ala Leu Ala Leu Lys Gly Glu Leu
 1               5                  10                  15

Leu Leu Leu Ser Leu Leu Leu Leu Glu Pro Gln Ile Ser Gln Gly
                20                  25                  30

Leu Val Val Thr Pro Pro Gly Pro Glu Leu Val Leu Asn Val Ser Ser
                35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                    85                  90                  95

Glu Tyr Phe Cys Thr His Asn Asp Ser Arg Gly Leu Glu Thr Asp Glu
                100                 105                 110

Arg Lys Arg Leu Tyr Ile Phe Val Pro Asp Pro Thr Val Gly Phe Leu
                115                 120                 125

Pro Asn Asp Ala Glu Glu Leu Phe Ile Phe Leu Thr Glu Ile Thr Glu
            130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                    165                 170                 175

Arg Gly Phe Ser Gly Ile Phe Glu Asp Arg Ser Tyr Ile Cys Lys Thr
                180                 185                 190

Thr Ile Gly Asp Arg Glu Val Asp Ser Asp Ala Tyr Tyr Val Tyr Arg
                195                 200                 205

Leu Gln Val Ser Ser Ile Asn Val Ser Val Asn Ala Val Gln Thr Val
            210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
                260                 265                 270

Arg Ser Ile Leu His Ile Pro Ser Ala Glu Leu Glu Asp Ser Gly Thr
                275                 280                 285

Tyr Thr Cys Asn Val Thr Glu Ser Val Asn Asp His Gln Asp Glu Lys
            290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
                340                 345                 350

Asp Asn Arg Thr Leu Gly Asp Ser Ser Ala Gly Glu Ile Ala Leu Ser
            355                 360                 365

Thr Arg Asn Val Ser Glu Thr Arg Tyr Val Ser Glu Leu Thr Leu Val
370                 375                 380

Arg Val Lys Val Ala Glu Ala Gly His Tyr Thr Met Arg Ala Phe His
385                 390                 395                 400
```

-continued

```
Glu Asp Ala Glu Val Gln Leu Ser Phe Gln Leu Gln Ile Asn Val Pro
            405                 410                 415
Val Arg Val Leu Glu Leu Ser Glu Ser His Pro Asp Ser Gly Glu Gln
        420                 425                 430
Thr Val Arg Cys Arg Gly Arg Gly Met Pro Gln Pro Asn Ile Ile Trp
        435                 440                 445
Ser Ala Cys Arg Asp Leu Lys Arg Cys Pro Arg Glu Leu Pro Pro Thr
450                 455                 460
Leu Leu Gly Asn Ser Ser Glu Glu Ser Gln Leu Glu Thr Asn Val
465                 470                 475                 480
Thr Tyr Trp Glu Glu Gln Glu Phe Glu Val Val Ser Thr Leu Arg
            485                 490                 495
Leu Gln His Val Asp Arg Pro Leu Ser Val Arg Cys Thr Leu Arg Asn
                500                 505                 510
Ala Val Gly Gln Asp Thr Gln Glu Val Ile Val Pro His Ser Leu
            515                 520                 525
Pro Phe Lys Val Val Ile Ser Ala Ile Leu Ala Leu Val Val Leu
        530                 535                 540
Thr Ile Ile Ser Leu Ile Ile Leu Ile Met Leu Trp Gln Lys Lys Pro
545                 550                 555                 560
Arg Tyr Glu Ile Arg Trp Lys Val Ile Glu Ser Val Ser Ser Asp Gly
            565                 570                 575
His Glu Tyr Ile Tyr Val Asp Pro Met Gln Leu Pro Tyr Asp Ser Thr
                580                 585                 590
Trp Glu Leu Pro Arg Asp Gln Leu Val Leu Gly Arg Thr Leu Gly Ser
            595                 600                 605
Gly Ala Phe Gly Gln Val Val Glu Ala Thr Ala His Gly Leu Ser His
        610                 615                 620
Ser Gln Ala Thr Met Lys Val Ala Val Lys Met Leu Lys Ser Thr Ala
625                 630                 635                 640
Arg Ser Ser Glu Lys Gln Ala Leu Met Ser Glu Leu Lys Ile Met Ser
            645                 650                 655
His Leu Gly Pro His Leu Asn Val Val Asn Leu Leu Gly Ala Cys Thr
                660                 665                 670
Lys Gly Gly Pro Ile Tyr Ile Ile Thr Glu Tyr Cys Arg Tyr Gly Asp
            675                 680                 685
Leu Val Asp Tyr Leu His Arg Asn Lys His Thr Phe Leu Gln His His
        690                 695                 700
Ser Asp Lys Arg Arg Pro Pro Ser Ala Glu Leu Tyr Ser Asn Ala Leu
705                 710                 715                 720
Pro Val Gly Leu Pro Leu Pro Ser His Val Ser Leu Thr Gly Glu Ser
            725                 730                 735
Asp Gly Gly Tyr Met Asp Met Ser Lys Asp Glu Ser Val Asp Tyr Val
                740                 745                 750
Pro Met Leu Asp Met Lys Gly Asp Val Lys Tyr Ala Asp Ile Glu Ser
            755                 760                 765
Ser Asn Tyr Met Ala Pro Tyr Asp Asn Tyr Val Pro Ser Ala Pro Glu
        770                 775                 780
Arg Thr Cys Arg Ala Thr Leu Ile Asn Glu Ser Pro Val Leu Ser Tyr
785                 790                 795                 800
Met Asp Leu Val Gly Phe Ser Tyr Gln Val Ala Asn Gly Met Glu Phe
            805                 810                 815
Leu Ala Ser Lys Asn Cys Val His Arg Asp Leu Ala Ala Arg Asn Val
        820                 825                 830
```

-continued

Leu Ile Cys Glu Gly Lys Leu Val Lys Ile Cys Asp Phe Gly Leu Ala
    835                 840                 845

Arg Asp Ile Met Arg Asp Ser Asn Tyr Ile Ser Lys Gly Ser Thr Phe
    850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
            885                 890                 895

Phe Thr Leu Gly Gly Thr Pro Tyr Pro Glu Leu Pro Met Asn Glu Gln
                900                 905                 910

Phe Tyr Asn Ala Ile Lys Arg Gly Tyr Arg Met Ala Gln Pro Ala His
        915                 920                 925

Ala Ser Asp Glu Ile Tyr Glu Ile Met Gln Lys Cys Trp Glu Glu Lys
    930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Lys Tyr Gln Gln Val Asp Glu Glu
                965                 970                 975

Phe Leu Arg Ser Asp His Pro Ala Ile Leu Arg Ser Gln Ala Arg Leu
            980                 985                 990

Pro Gly Phe His Gly Leu Arg Ser Pro Leu Asp Thr Ser Ser Val Leu
            995                 1000                1005

Tyr Thr Ala Val Gln Pro Asn Glu Gly Asp Asn Asp Tyr Ile Ile Pro
    1010                1015                1020

Leu Pro Asp Pro Lys Pro Glu Val Ala Asp Glu Gly Pro Leu Glu Gly
1025                1030                1035                1040

Ser Pro Ser Leu Ala Ser Ser Thr Leu Asn Glu Val Asn Thr Ser Ser
                1045                1050                1055

Thr Ile Ser Cys Asp Ser Pro Leu Glu Pro Gln Asp Glu Pro Glu Pro
            1060                1065                1070

Glu Pro Gln Leu Glu Leu Gln Val Glu Pro Glu Pro Glu Leu Glu Gln
            1075                1080                1085

Leu Pro Asp Ser Gly Cys Pro Ala Pro Arg Ala Glu Ala Glu Asp Ser
    1090                1095                1100

Phe Leu
1105

(2) INFORMATION FOR SEQ ID NO:3:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: Other nucleic acid (iii) HYPOTHETICAL: N (iv) ANTI-SENSE: N (vii) IMMEDIATE SOURCE:
        (B) CLONE: ZC871

(xi) SEQUENCE DESCRIPTION: SEQ ID NO:3:

ATTATACGCT CTCTTCCTCA GGTAAATGAG TGCCAGGGCC GGCAAGCCCC CGCTCCA    57

(2) INFORMATION FOR SEQ ID NO:4:

(i) SEQUENCE CHARACTERISTICS:
            (A) LENGTH: 56 base pairs
            (B) TYPE: nucleic acid
            (C) STRANDEDNESS: single
            (D) TOPOLOGY: linear (ii) MOLECULE TYPE: Other nucleic acid (iii) HYPOTHETICAL: N (iv) ANTI-SENSE: N (vii) IMMEDIATE SOURCE:
            (B) CLONE: ZC872

(xi) SEQUENCE DESCRIPTION: SEQ ID NO:4:

CCGGGGAGCG GGGGCTTGCC GGCCCTGGCA CTCATTTACC TGAGGAAGAG AGAGCT          56

(2) INFORMATION FOR SEQ ID NO:5:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: Other nucleic acid (iii) HYPOTHETICAL: N (iv) ANTI-SENSE: N (vii) IMMEDIATE SOURCE:
            (B) CLONE: ZC904

(xi) SEQUENCE DESCRIPTION: SEQ ID NO:5:

CATGGGCACG TAATCTATAG ATTCATCCTT GCTCATATCC ATGTA                     45

(2) INFORMATION FOR SEQ ID NO:6:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: Other nucleic acid (iii) HYPOTHETICAL: N (iv) ANTI-SENSE: N (vii) IMMEDIATE SOURCE:
            (B) CLONE: ZC906

(xi) SEQUENCE DESCRIPTION: SEQ ID NO:6:

AAGCTGTCCT CTGCTTCAGC CAGAGGTCCT GGGCAGCC                             38

(2) INFORMATION FOR SEQ ID NO:7:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: Other nucleic acid (iii) HYPOTHETICAL: N (iv) ANTI-SENSE: N (vii) IMMEDIATE SOURCE:
            (B) CLONE: ZC906

(xi) SEQUENCE DESCRIPTION: SEQ ID NO:7:

AAGCTGTCCT CTGCTTCAGC CAGAGGTCCT GGGCAGCC                        38

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (iii) HYPOTHETICAL: N (iv) ANTI-SENSE: N (vii) IMMEDIATE SOURCE:
        (B) CLONE: ZC1380

(xi) SEQUENCE DESCRIPTION: SEQ ID NO:8:

CATGGTGGAA TTCCTGCTGA T                                          21

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other nucleic acid (iii) HYPOTHETICAL: N (iv) ANTI-SENSE: N (vii) IMMEDIATE SOURCE:
        (B) CLONE: ZC1447

(xi) SEQUENCE DESCRIPTION: SEQ ID NO:9:

TGGTTGTGCA GAGCTGAGGA AGAGATGGA                                  29

(2) INFORMATION FOR SEQ ID NO:10:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: Other nucleic acid (iii) HYPOTHETICAL: N (iv) ANTI-SENSE: N (vii) IMMEDIATE SOURCE:
        (B) CLONE: ZC1453

(xi) SEQUENCE DESCRIPTION: SEQ ID NO:10:

AATTCATTAT GTTGTTGCAA GCCTTCTTGT TCCTGCTAGC TGGTTTCGCT GTTAA      55

(2) INFORMATION FOR SEQ ID NO:11:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: Other nucleic acid (iii) HYPOTHETICAL: N (iv) ANTI-SENSE: N (vii) IMMEDIATE SOURCE:
                 (B) CLONE: ZC1454

(xi) SEQUENCE DESCRIPTION: SEQ ID NO:11:

GATCTTAACA GCGAAACCAG CTAGCAGGAA CAAGAAGGCT TGCAACAACA TAATG                55

(2) INFORMATION FOR SEQ ID NO:12:

(i) SEQUENCE CHARACTERISTICS:
                 (A) LENGTH: 21 base pairs
                 (B) TYPE: nucleic acid
                 (C) STRANDEDNESS: single
                 (D) TOPOLOGY: linear (ii) MOLECULE TYPE: Other nucleic acid (iii) HYPOTHETICAL: N (iv) ANTI-SENSE: N (vii) IMMEDIATE SOURCE:
                 (B) CLONE: ZC1478

(xi) SEQUENCE DESCRIPTION: SEQ ID NO:12:

ATCGCGAGCA TGCAGATCTG A                                                     21

(2) INFORMATION FOR SEQ ID NO:13:

(i) SEQUENCE CHARACTERISTICS:
                 (A) LENGTH: 25 base pairs
                 (B) TYPE: nucleic acid
                 (C) STRANDEDNESS: single
                 (D) TOPOLOGY: linear (ii) MOLECULE TYPE: Other nucleic acid (iii) HYPOTHETICAL: N (iv) ANTI-SENSE: N (vii) IMMEDIATE SOURCE:
                 (B) CLONE: ZC1479

(xi) SEQUENCE DESCRIPTION: SEQ ID NO:13:

AGCTTCAGAT CTGCATGCTG CCGAT                                                 25

(2) INFORMATION FOR SEQ ID NO:14:

(i) SEQUENCE CHARACTERISTICS:
                 (A) LENGTH: 52 base pairs
                 (B) TYPE: nucleic acid
                 (C) STRANDEDNESS: single
                 (D) TOPOLOGY: linear (ii) MOLECULE TYPE: Other nucleic acid (iii) HYPOTHETICAL: N (iv) ANTI-SENSE: N (vii) IMMEDIATE SOURCE:
                 (B) CLONE: ZC1776

(xi) SEQUENCE DESCRIPTION: SEQ ID NO:14:

AGCTGAGCGC AAATGTTGTG TCGAGTGCCC ACCGTGCCCA GCTTAGAATT CT                   52

(2) INFORMATION FOR SEQ ID NO:15:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: Other nucleic acid (iii) HYPOTHETICAL: N (iv) ANTI-SENSE: N (vii) IMMEDIATE SOURCE:
        (B) CLONE: ZC1777

(xi) SEQUENCE DESCRIPTION: SEQ ID NO:15:

```
CTAGAGAATT CTAAGCTGGG CACGGTGGGC ACTCGACACA ACATTTGCGC TC              52
```

(2) INFORMATION FOR SEQ ID NO:16:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: Other nucleic acid (iii) HYPOTHETICAL: N (iv) ANTI-SENSE: N (vii) IMMEDIATE SOURCE:
        (B) CLONE: ZC1846

(xi) SEQUENCE DESCRIPTION: SEQ ID NO:16:

```
GATCGGCCAC TGTCGGTGCG CTGCACGCTG CGCAACGCTG TGGGCCAGGA CACGCAGGAG      60

GTCATCGTGG TGCCACACTC CTTGCCCTTT AAGCA                                 95
```

(2) INFORMATION FOR SEQ ID NO:17:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: Other nucleic acid (iii) HYPOTHETICAL: N (iv) ANTI-SENSE: N (vii) IMMEDIATE SOURCE:
        (B) CLONE: ZC1847

(xi) SEQUENCE DESCRIPTION: SEQ ID NO:17:

```
AGCTTGCTTA AAGGGCAAGG AGTGTGGCAC CACGATGACC TCCTGCGTGT CCTGGCCCAC      60

AGCGTTGCGC AGCGTGCAGC GCACCGACAG TGGCC                                 95
```

(2) INFORMATION FOR SEQ ID NO:18:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: Other nucleic acid

```
        (iii) HYPOTHETICAL: N (iv) ANTI-SENSE: N (vii) IMMEDIATE SOURCE:
              (B) CLONE: ZC1886

(xi) SEQUENCE DESCRIPTION: SEQ ID NO:18:

CCAGTGCCAA GCTTGTCTAG ACTTACCTTT AAAGGGCAAG GAG                         43

(2) INFORMATION FOR SEQ ID NO:19:

(i) SEQUENCE CHARACTERISTICS:
              (A) LENGTH: 11 base pairs
              (B) TYPE: nucleic acid
              (C) STRANDEDNESS: single
              (D) TOPOLOGY: linear (ii) MOLECULE TYPE: Other nucleic acid (iii) HYPOTHETICAL: N (iv) ANTI-SENSE: N (vii) IMMEDIATE SOURCE:
              (B) CLONE: ZC1892

(xi) SEQUENCE DESCRIPTION: SEQ ID NO:19:

AGCTTGAGCG T                                                            11

(2) INFORMATION FOR SEQ ID NO:20:

(i) SEQUENCE CHARACTERISTICS:
              (A) LENGTH: 11 base pairs
              (B) TYPE: nucleic acid
              (C) STRANDEDNESS: single
              (D) TOPOLOGY: linear (ii) MOLECULE TYPE: Other nucleic acid (iii) HYPOTHETICAL: N (iv) ANTI-SENSE: N (vii) IMMEDIATE SOURCE:
              (B) CLONE: ZC1893

(xi) SEQUENCE DESCRIPTION: SEQ ID NO:20:

CTAGACGCTC A                                                            11

(2) INFORMATION FOR SEQ ID NO:21:

(i) SEQUENCE CHARACTERISTICS:
              (A) LENGTH: 47 base pairs
              (B) TYPE: nucleic acid
              (C) STRANDEDNESS: single
              (D) TOPOLOGY: linear (ii) MOLECULE TYPE: Other nucleic acid (iii) HYPOTHETICAL: N (iv) ANTI-SENSE: N (vii) IMMEDIATE SOURCE:
              (B) CLONE: ZC1894

(xi) SEQUENCE DESCRIPTION: SEQ ID NO:21:

AGCTTCCAGT TCTTCGGCCT CATGTCAGTT CTTCGGCCTC ATGTGAT                     47

(2) INFORMATION FOR SEQ ID NO:22:
```

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: Other nucleic acid (iii) HYPOTHETICAL: N (iv) ANTI-SENSE: N (vii) IMMEDIATE SOURCE:
        (B) CLONE: ZC1895

(xi) SEQUENCE DESCRIPTION: SEQ ID NO:22:

CTAGATCACA TGAGGCCGAA GAACTGACAT GAGGCCGAAG AACTGGA                47

(2) INFORMATION FOR SEQ ID NO:23:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: Other nucleic acid (iii) HYPOTHETICAL: N (iv) ANTI-SENSE: N (vii) IMMEDIATE SOURCE:
        (B) CLONE: ZC2181

(xi) SEQUENCE DESCRIPTION: SEQ ID NO:23:

AATTCGGATC CACCATGGGC ACCAGCCACC CGGCGTTCCT GGTGTTAGGC TGCCTGCTGA    60

CCGGCC                                                               66

(2) INFORMATION FOR SEQ ID NO:24:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: Other nucleic acid (iii) HYPOTHETICAL: N (iv) ANTI-SENSE: N (vii) IMMEDIATE SOURCE:
        (B) CLONE: ZC2182

(xi) SEQUENCE DESCRIPTION: SEQ ID NO:24:

TGAGCCTGAT CCTGTGCCAA CTGAGCCTGC CATCGATCCT GCCAAACGAG AACGAGAAGG    60

TTGTGCAGCT A                                                         71

(2) INFORMATION FOR SEQ ID NO:25:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: Other nucleic acid (iii) HYPOTHETICAL: N (iv) ANTI-SENSE: N (vii) IMMEDIATE SOURCE:
             (B) CLONE: ZC2183

(xi) SEQUENCE DESCRIPTION: SEQ ID NO:25:

AATTTAGCTG CACAACCTTC TCGTTCTCGT TTGGCAGGAT CGATGGCAGG CTCAGTTGGC      60

ACAGGATCA                                                             69

(2) INFORMATION FOR SEQ ID NO:26:

(i) SEQUENCE CHARACTERISTICS:
             (A) LENGTH: 68 base pairs
             (B) TYPE: nucleic acid
             (C) STRANDEDNESS: single
             (D) TOPOLOGY: linear (ii) MOLECULE TYPE: Other nucleic acid (iii) HYPOTHETICAL: N (iv) ANTI-SENSE: N (vii) IMMEDIATE SOURCE:
             (B) CLONE: ZC2184

(xi) SEQUENCE DESCRIPTION: SEQ ID NO:26:

GGCTCAGGCC GGTCAGCAGG CAGCCTAACA CCAGGAACGC CGGGTGGCTG GTGCCCATGG      60

TGGATCCG                                                              68

(2) INFORMATION FOR SEQ ID NO:27:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: Other nucleic acid (iii) HYPOTHETICAL: N (iv) ANTI-SENSE: N (vii) IMMEDIATE SOURCE:
             (B) CLONE: ZC2311

(xi) SEQUENCE DESCRIPTION: SEQ ID NO:27:

TGATCACCAT GGCTCAACTG                                                 20

(2) INFORMATION FOR SEQ ID NO:28:

(i) SEQUENCE CHARACTERISTICS:
             (A) LENGTH: 10 base pairs
             (B) TYPE: nucleic acid
             (C) STRANDEDNESS: single
             (D) TOPOLOGY: linear (ii) MOLECULE TYPE: Other nucleic acid (iii) HYPOTHETICAL: N (iv) ANTI-SENSE: N (vii) IMMEDIATE SOURCE:
             (B) CLONE: ZC2351

(xi) SEQUENCE DESCRIPTION: SEQ ID NO:28:

CGAATTCCAC                                                            10

(2) INFORMATION FOR SEQ ID NO:29:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other nucleic acid (iii) HYPOTHETICAL: N (iv) ANTI-SENSE: N (vii) IMMEDIATE SOURCE:
        (B) CLONE: ZC2352

(xi) SEQUENCE DESCRIPTION: SEQ ID NO:29:

ATTATACGCA TGGTGGAATT CGAGCT                                          26

(2) INFORMATION FOR SEQ ID NO:30:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: Other nucleic acid (iii) HYPOTHETICAL: N (iv) ANTI-SENSE: N (vii) IMMEDIATE SOURCE:
        (B) CLONE: ZC2392

(xi) SEQUENCE DESCRIPTION: SEQ ID NO:30:

ACGTAAGCTT GTCTAGACTT ACCTTCAGAA CGCAGGGTGG G                       41

(2) INFORMATION FOR SEQ ID NO:31:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (v) FRAGMENT TYPE: C-terminal (vii) IMMEDIATE SOURCE:
        (B) CLONE: pWK1

(xi) SEQUENCE DESCRIPTION: SEQ ID NO:31:

Ala Leu His Asn His Tyr Thr Glu Lys Ser Leu Ser Leu Ser Pro Gly
1                 5                     10                15

Lys (2) INFORMATION FOR SEQ ID NO:32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid (iii) HYPOTHETICAL: N (iv) ANTI-SENSE: N (xi) SEQUENCE DESCRIPTION: SEQ ID NO:32:

TGTGACACTC TCCTGGGAGT TA                                                    22

(2) INFORMATION FOR SEQ ID NO:33:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: Other nucleic acid (iii) HYPOTHETICAL: N (iv) ANTI-SENSE: N (xi) SEQUENCE DESCRIPTION: SEQ ID NO:33:

GCATAGTAGT TACCATATCC TCTTGCACAG                                            30

(2) INFORMATION FOR SEQ ID NO:34:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: Other nucleic acid (iii) HYPOTHETICAL: N (iv) ANTI-SENSE: N (xi) SEQUENCE DESCRIPTION: SEQ ID NO:34:

ACCGAACGTG AGAGGAGTGC TATAA                                                 25

(2) INFORMATION FOR SEQ ID NO:35:

(i) SEQUENCE CHARACTERISTICS:
            (A) LENGTH: 4054 base pairs
            (B) TYPE: nucleic acid
            (C) STRANDEDNESS: double
            (D) TOPOLOGY: linear (ii) MOLECULE TYPE: cDNA (iii) HYPOTHETICAL: N (iv) ANTI-SENSE: N (vi) ORIGINAL SOURCE:
            (A) ORGANISM: Homo sapiens (vii) IMMEDIATE SOURCE:
            (B) CLONE: p-alpha-17B (ix) FEATURE:
            (A) NAME/KEY: CDS
            (B) LOCATION: 205..3471
            (D) OTHER INFORMATION:

(xi) SEQUENCE DESCRIPTION: SEQ ID NO:35:

GCCCTGGGGA CGGACCGTGG GCGGCGCGCA GCGGCGGGAC GCGTTTTGGG GACGTGGTGG           60

CCAGCGCCTT CCTGCAGACC CACAGGGAAG TACTCCCTTT GACCTCCGGG GAGCTGCGAC          120

CAGGTTATAC GTTGCTGGTG GAAAAGTGAC AATTCTAGGA AAAGAGCTAA AGCCGGATC           180

GGTGACCGAA AGTTTCCCAG AGCT ATG GGG ACT TCC CAT CCG GCG TTC CTG            231
                          Met Gly Thr Ser His Pro Ala Phe Leu
                            1               5

-continued

| | | | | | | | | | | | | | | | | |
|---|---|---|---|---|---|---|---|---|---|---|---|---|---|---|---|---|
| GTC | TTA | GGC | TGT | CTT | CTC | ACA | GGG | CTG | AGC | CTA | ATC | CTC | TGC | CAG | CTT | 279 |
| Val | Leu | Gly | Cys | Leu | Leu | Thr | Gly | Leu | Ser | Leu | Ile | Leu | Cys | Gln | Leu | |
| 10 | | | | | 15 | | | | 20 | | | | | 25 | | |

| TCA | TTA | CCC | TCT | ATC | CTT | CCA | AAT | GAA | AAT | GAA | AAG | GTT | GTG | CAG | CTG | 327 |
|---|---|---|---|---|---|---|---|---|---|---|---|---|---|---|---|---|
| Ser | Leu | Pro | Ser | Ile | Leu | Pro | Asn | Glu | Asn | Glu | Lys | Val | Val | Gln | Leu | |
| | | | 30 | | | | | 35 | | | | | 40 | | | |

| AAT | TCA | TCC | TTT | TCT | CTG | AGA | TGC | TTT | GGG | GAG | AGT | GAA | GTG | AGC | TGG | 375 |
|---|---|---|---|---|---|---|---|---|---|---|---|---|---|---|---|---|
| Asn | Ser | Ser | Phe | Ser | Leu | Arg | Cys | Phe | Gly | Glu | Ser | Glu | Val | Ser | Trp | |
| | | | 45 | | | | | 50 | | | | | 55 | | | |

| CAG | TAC | CCC | ATG | TCT | GAA | GAA | GAG | AGC | TCC | GAT | GTG | GAA | ATC | AGA | AAT | 423 |
|---|---|---|---|---|---|---|---|---|---|---|---|---|---|---|---|---|
| Gln | Tyr | Pro | Met | Ser | Glu | Glu | Glu | Ser | Ser | Asp | Val | Glu | Ile | Arg | Asn | |
| | | 60 | | | | | 65 | | | | | 70 | | | | |

| GAA | GAA | AAC | AAC | AGC | GGC | CTT | TTT | GTG | ACG | GTC | TTG | GAA | GTG | AGC | AGT | 471 |
|---|---|---|---|---|---|---|---|---|---|---|---|---|---|---|---|---|
| Glu | Glu | Asn | Asn | Ser | Gly | Leu | Phe | Val | Thr | Val | Leu | Glu | Val | Ser | Ser | |
| 75 | | | | | 80 | | | | | 85 | | | | | | |

| GCC | TCG | GCG | GCC | CAC | ACA | GGG | TTG | TAC | ACT | TGC | TAT | TAC | AAC | CAC | ACT | 519 |
|---|---|---|---|---|---|---|---|---|---|---|---|---|---|---|---|---|
| Ala | Ser | Ala | Ala | His | Thr | Gly | Leu | Tyr | Thr | Cys | Tyr | Tyr | Asn | His | Thr | |
| 90 | | | | 95 | | | | | 100 | | | | | 105 | | |

| CAG | ACA | GAA | GAG | AAT | GAG | CTT | GAA | GGC | AGG | CAC | ATT | TAC | ATC | TAT | GTG | 567 |
|---|---|---|---|---|---|---|---|---|---|---|---|---|---|---|---|---|
| Gln | Thr | Glu | Glu | Asn | Glu | Leu | Glu | Gly | Arg | His | Ile | Tyr | Ile | Tyr | Val | |
| | | | | 110 | | | | | 115 | | | | | 120 | | |

| CCA | GAC | CCA | GAT | GTA | GCC | TTT | GTA | CCT | CTA | GGA | ATG | ACG | GAT | TAT | TTA | 615 |
|---|---|---|---|---|---|---|---|---|---|---|---|---|---|---|---|---|
| Pro | Asp | Pro | Asp | Val | Ala | Phe | Val | Pro | Leu | Gly | Met | Thr | Asp | Tyr | Leu | |
| | | | 125 | | | | | 130 | | | | | 135 | | | |

| GTC | ATC | GTG | GAG | GAT | GAT | GAT | TCT | GCC | ATT | ATA | CCT | TGT | CGC | ACA | ACT | 663 |
|---|---|---|---|---|---|---|---|---|---|---|---|---|---|---|---|---|
| Val | Ile | Val | Glu | Asp | Asp | Asp | Ser | Ala | Ile | Ile | Pro | Cys | Arg | Thr | Thr | |
| | | 140 | | | | | 145 | | | | | 150 | | | | |

| GAT | CCC | GAG | ACT | CCT | GTA | ACC | TTA | CAC | AAC | AGT | GAG | GGG | GTG | GTA | CCT | 711 |
|---|---|---|---|---|---|---|---|---|---|---|---|---|---|---|---|---|
| Asp | Pro | Glu | Thr | Pro | Val | Thr | Leu | His | Asn | Ser | Glu | Gly | Val | Val | Pro | |
| | 155 | | | | | 160 | | | | | 165 | | | | | |

| GCC | TCC | TAC | GAC | AGC | AGA | CAG | GGC | TTT | AAT | GGG | ACC | TTC | ACT | GTA | GGG | 759 |
|---|---|---|---|---|---|---|---|---|---|---|---|---|---|---|---|---|
| Ala | Ser | Tyr | Asp | Ser | Arg | Gln | Gly | Phe | Asn | Gly | Thr | Phe | Thr | Val | Gly | |
| 170 | | | | 175 | | | | | 180 | | | | | 185 | | |

| CCC | TAT | ATC | TGT | GAG | GCC | ACC | GTC | AAA | GGA | AAG | AAG | TTC | CAG | ACC | ATC | 807 |
|---|---|---|---|---|---|---|---|---|---|---|---|---|---|---|---|---|
| Pro | Tyr | Ile | Cys | Glu | Ala | Thr | Val | Lys | Gly | Lys | Lys | Phe | Gln | Thr | Ile | |
| | | | | 190 | | | | | 195 | | | | | 200 | | |

| CCA | TTT | AAT | GTT | TAT | GCT | TTA | AAA | GCA | ACA | TCA | GAG | CTG | GAT | CTA | GAA | 855 |
|---|---|---|---|---|---|---|---|---|---|---|---|---|---|---|---|---|
| Pro | Phe | Asn | Val | Tyr | Ala | Leu | Lys | Ala | Thr | Ser | Glu | Leu | Asp | Leu | Glu | |
| | | | | 205 | | | | | 210 | | | | | 215 | | |

| ATG | GAA | GCT | CTT | AAA | ACC | GTG | TAT | AAG | TCA | GGG | GAA | ACG | ATT | GTG | GTC | 903 |
|---|---|---|---|---|---|---|---|---|---|---|---|---|---|---|---|---|
| Met | Glu | Ala | Leu | Lys | Thr | Val | Tyr | Lys | Ser | Gly | Glu | Thr | Ile | Val | Val | |
| | | | 220 | | | | | 225 | | | | | 230 | | | |

| ACC | TGT | GCT | GTT | TTT | AAC | AAT | GAG | GTG | GTT | GAC | CTT | CAA | TGG | ACT | TAC | 951 |
|---|---|---|---|---|---|---|---|---|---|---|---|---|---|---|---|---|
| Thr | Cys | Ala | Val | Phe | Asn | Asn | Glu | Val | Val | Asp | Leu | Gln | Trp | Thr | Tyr | |
| | 235 | | | | | 240 | | | | | 245 | | | | | |

| CCT | GGA | GAA | GTG | AAA | GGC | AAA | GGC | ATC | ACA | ATA | CTG | GAA | GAA | ATC | AAA | 999 |
|---|---|---|---|---|---|---|---|---|---|---|---|---|---|---|---|---|
| Pro | Gly | Glu | Val | Lys | Gly | Lys | Gly | Ile | Thr | Ile | Leu | Glu | Glu | Ile | Lys | |
| 250 | | | | 255 | | | | | 260 | | | | | 265 | | |

| GTC | CCA | TCC | ATC | AAA | TTG | GTG | TAC | ACT | TTG | ACG | GTC | CCC | GAG | GCC | ACG | 1047 |
|---|---|---|---|---|---|---|---|---|---|---|---|---|---|---|---|---|
| Val | Pro | Ser | Ile | Lys | Leu | Val | Tyr | Thr | Leu | Thr | Val | Pro | Glu | Ala | Thr | |
| | | | | 270 | | | | | 275 | | | | | 280 | | |

| GTG | AAA | GAC | AGT | GGA | GAT | TAC | GAA | TGT | GCT | GCC | CGC | CAG | GCT | ACC | AGG | 1095 |
|---|---|---|---|---|---|---|---|---|---|---|---|---|---|---|---|---|
| Val | Lys | Asp | Ser | Gly | Asp | Tyr | Glu | Cys | Ala | Ala | Arg | Gln | Ala | Thr | Arg | |
| | | | 285 | | | | | 290 | | | | | 295 | | | |

| GAG | GTC | AAA | GAA | ATG | AAG | AAA | GTC | ACT | ATT | TCT | GTC | CAT | GAG | AAA | GGT | 1143 |
|---|---|---|---|---|---|---|---|---|---|---|---|---|---|---|---|---|
| Glu | Val | Lys | Glu | Met | Lys | Lys | Val | Thr | Ile | Ser | Val | His | Glu | Lys | Gly | |
| | | | 300 | | | | | 305 | | | | | 310 | | | |

| TTC | ATT | GAA | ATC | AAA | CCC | ACC | TTC | AGC | CAG | TTG | GAA | GCT | GTC | AAC | CTG | 1191 |
|---|---|---|---|---|---|---|---|---|---|---|---|---|---|---|---|---|
| Phe | Ile | Glu | Ile | Lys | Pro | Thr | Phe | Ser | Gln | Leu | Glu | Ala | Val | Asn | Leu | |
| | | 315 | | | | | 320 | | | | | 325 | | | | |

| | |
|---|---|
| CAT GAA GTC AAA CAT TTT GTT GTA GAG GTG CGG GCC TAC CCA CCT CCC<br>His Glu Val Lys His Phe Val Val Glu Val Arg Ala Tyr Pro Pro Pro<br>330                   335                  340               345 | 1239 |
| AGG ATA TCC TGG CTG AAA AAC AAT CTG ACT CTG ATT GAA AAT CTC ACT<br>Arg Ile Ser Trp Leu Lys Asn Asn Leu Thr Leu Ile Glu Asn Leu Thr<br>              350                  355                  360 | 1287 |
| GAG ATC ACC ACT GAT GTG GAA AAG ATT CAG GAA ATA AGG TAT CGA AGC<br>Glu Ile Thr Thr Asp Val Glu Lys Ile Gln Glu Ile Arg Tyr Arg Ser<br>              365                  370                  375 | 1335 |
| AAA TTA AAG CTG ATC CGT GCT AAG GAA GAA GAC AGT GGC CAT TAT ACT<br>Lys Leu Lys Leu Ile Arg Ala Lys Glu Glu Asp Ser Gly His Tyr Thr<br>380                            385                  390 | 1383 |
| ATT GTA GCT CAA AAT GAA GAT GCT GTG AAG AGC TAT ACT TTT GAA CTG<br>Ile Val Ala Gln Asn Glu Asp Ala Val Lys Ser Tyr Thr Phe Glu Leu<br>              395                  400                  405 | 1431 |
| TTA ACT CAA GTT CCT TCA TCC ATT CTG GAC TTG GTC GAT GAT CAC CAT<br>Leu Thr Gln Val Pro Ser Ser Ile Leu Asp Leu Val Asp Asp His His<br>410                            415                  420               425 | 1479 |
| GGC TCA ACT GGG GGA CAG ACG GTG AGG TGC ACA GCT GAA GGC ACG CCG<br>Gly Ser Thr Gly Gly Gln Thr Val Arg Cys Thr Ala Glu Gly Thr Pro<br>                       430                  435                  440 | 1527 |
| CTT CCT GAT ATT GAG TGG ATG ATA TGC AAA GAT ATT AAG AAA TGT AAT<br>Leu Pro Asp Ile Glu Trp Met Ile Cys Lys Asp Ile Lys Lys Cys Asn<br>                    445                  450                  455 | 1575 |
| AAT GAA ACT TCC TGG ACT ATT TTG GCC AAC AAT GTC TCA AAC ATC ATC<br>Asn Glu Thr Ser Trp Thr Ile Leu Ala Asn Asn Val Ser Asn Ile Ile<br>             460                  465                  470 | 1623 |
| ACG GAG ATC CAC TCC CGA GAC AGG AGT ACC GTG GAG GGC CGT GTG ACT<br>Thr Glu Ile His Ser Arg Asp Arg Ser Thr Val Glu Gly Arg Val Thr<br>475                           480                        485 | 1671 |
| TTC GCC AAA GTG GAG GAG ACC ATC GCC GTG CGA TGC CTG GCT AAG AAT<br>Phe Ala Lys Val Glu Glu Thr Ile Ala Val Arg Cys Leu Ala Lys Asn<br>490                           495                  500               505 | 1719 |
| CTC CTT GGA GCT GAG AAC CGA GAG CTG AAG CTG GTG GCT CCC ACC CTG<br>Leu Leu Gly Ala Glu Asn Arg Glu Leu Lys Leu Val Ala Pro Thr Leu<br>                     510                  515                  520 | 1767 |
| CGT TCT GAA CTC ACG GTG GCT GCT GCA GTC CTG GTG CTG TTG GTG ATT<br>Arg Ser Glu Leu Thr Val Ala Ala Ala Val Leu Val Leu Leu Val Ile<br>                 525                  530                  535 | 1815 |
| GTG ATC ATC TCA CTT ATT GTC CTG GTT GTC ATT TGG AAA CAG AAA CCG<br>Val Ile Ile Ser Leu Ile Val Leu Val Val Ile Trp Lys Gln Lys Pro<br>540                           545                  550 | 1863 |
| AGG TAT GAA ATT CGC TGG AGG GTC ATT GAA TCA ATC AGC CCG GAT GGA<br>Arg Tyr Glu Ile Arg Trp Arg Val Ile Glu Ser Ile Ser Pro Asp Gly<br>             555                  560                  565 | 1911 |
| CAT GAA TAT ATT TAT GTG GAC CCG ATG CAG CTG CCT TAT GAC TCA AGA<br>His Glu Tyr Ile Tyr Val Asp Pro Met Gln Leu Pro Tyr Asp Ser Arg<br>570                           575                  580               585 | 1959 |
| TGG GAG TTT CCA AGA GAT GGA CTA GTG CTT GGT CGG GTC TTG GGG TCT<br>Trp Glu Phe Pro Arg Asp Gly Leu Val Leu Gly Arg Val Leu Gly Ser<br>                    590                  595                  600 | 2007 |
| GGA GCG TTT GGG AAG GTG GTT GAA GGA ACA GCC TAT GGA TTA AGC CGG<br>Gly Ala Phe Gly Lys Val Val Glu Gly Thr Ala Tyr Gly Leu Ser Arg<br>                 605                  610                  615 | 2055 |
| TCC CAA CCT GTC ATG AAA GTT GCA GTG AAG ATG CTA AAA CCC ACG GCC<br>Ser Gln Pro Val Met Lys Val Ala Val Lys Met Leu Lys Pro Thr Ala<br>620                           625                  630 | 2103 |
| AGA TCC AGT GAA AAA CAA GCT CTC ATG TCT GAA CTG AAG ATA ATG ACT<br>Arg Ser Ser Glu Lys Gln Ala Leu Met Ser Glu Leu Lys Ile Met Thr<br>             635                  640                  645 | 2151 |

-continued

| | |
|---|---|
| CAC CTG GGG CCA CAT TTG AAC ATT GTA AAC TTG CTG GGA GCC TGC ACC<br>His Leu Gly Pro His Leu Asn Ile Val Asn Leu Leu Gly Ala Cys Thr<br>650                            655                         660                          665 | 2199 |
| AAG TCA GGC CCC ATT TAC ATC ATC ACA GAG TAT TGC TTC TAT GGA GAT<br>Lys Ser Gly Pro Ile Tyr Ile Ile Thr Glu Tyr Cys Phe Tyr Gly Asp<br>                       670                         675                         680 | 2247 |
| TTG GTC AAC TAT TTG CAT AAG AAT AGG GAT AGC TTC CTG AGC CAC CAC<br>Leu Val Asn Tyr Leu His Lys Asn Arg Asp Ser Phe Leu Ser His His<br>                685                         690                         695 | 2295 |
| CCA GAG AAG CCA AAG AAA GAG CTG GAT ATC TTT GGA TTG AAC CCT GCT<br>Pro Glu Lys Pro Lys Lys Glu Leu Asp Ile Phe Gly Leu Asn Pro Ala<br>700                            705                         710 | 2343 |
| GAT GAA AGC ACA CGG AGC TAT GTT ATT TTA TCT TTT GAA AAC AAT GGT<br>Asp Glu Ser Thr Arg Ser Tyr Val Ile Leu Ser Phe Glu Asn Asn Gly<br>              715                         720                       725 | 2391 |
| GAC TAC ATG GAC ATG AAG CAG GCT GAT ACT ACA CAG TAT GTC CCC ATG<br>Asp Tyr Met Asp Met Lys Gln Ala Asp Thr Thr Gln Tyr Val Pro Met<br>730                            735                         740                         745 | 2439 |
| CTA GAA AGG AAA GAG GTT TCT AAA TAT TCC GAC ATC CAG AGA TCA CTC<br>Leu Glu Arg Lys Glu Val Ser Lys Tyr Ser Asp Ile Gln Arg Ser Leu<br>                       750                         755                       760 | 2487 |
| TAT GAT CGT CCA GCC TCA TAT AAG AAG AAA TCT ATG TTA GAC TCA GAA<br>Tyr Asp Arg Pro Ala Ser Tyr Lys Lys Lys Ser Met Leu Asp Ser Glu<br>                765                         770                       775 | 2535 |
| GTC AAA AAC CTC CTT TCA GAT GAT AAC TCA GAA GGC TTT ACT TTA TTG<br>Val Lys Asn Leu Leu Ser Asp Asp Asn Ser Glu Gly Leu Thr Leu Leu<br>780                            785                         790 | 2583 |
| GAT TTG TTG AGC TTC ACC TAT CAA GTT GCC CGA GGA ATG GAG TTT TTG<br>Asp Leu Leu Ser Phe Thr Tyr Gln Val Ala Arg Gly Met Glu Phe Leu<br>     795                         800                       805 | 2631 |
| GCT TCA AAA AAT TGT GTC CAC CGT GAT CTG GCT GCT CGC AAC GTC CTC<br>Ala Ser Lys Asn Cys Val His Arg Asp Leu Ala Ala Arg Asn Val Leu<br>810                            815                         820                       825 | 2679 |
| CTG GCA CAA GGA AAA ATT GTG AAG ATC TGT GAC TTT GGC CTG GCC AGA<br>Leu Ala Gln Gly Lys Ile Val Lys Ile Cys Asp Phe Gly Leu Ala Arg<br>                830                         835                       840 | 2727 |
| GAC ATC ATG CAT GAT TCG AAC TAT GTG TCG AAA GGC AGT ACC TTT CTG<br>Asp Ile Met His Asp Ser Asn Tyr Val Ser Lys Gly Ser Thr Phe Leu<br>                       845                         850                       855 | 2775 |
| CCC GTG AAG TGG ATG GCT CCT GAG AGC ATC TTT GAC AAC CTC TAC ACC<br>Pro Val Lys Trp Met Ala Pro Glu Ser Ile Phe Asp Asn Leu Tyr Thr<br>            860                         865                       870 | 2823 |
| ACA CTG AGT GAT GTC TGG TCT TAT GGC ATT CTG CTC TGG GAG ATC TTT<br>Thr Leu Ser Asp Val Trp Ser Tyr Gly Ile Leu Leu Trp Glu Ile Phe<br>875                            880                         885 | 2871 |
| TCC CTT GGT GGC ACC CCT TAC CCC GGC ATG ATG GTG GAT TCT ACT TTC<br>Ser Leu Gly Gly Thr Pro Tyr Pro Gly Met Met Val Asp Ser Thr Phe<br>890                            895                         900                       905 | 2919 |
| TAC AAT AAG ATC AAG AGT GGG TAC CGG ATG GCC AAG CCT GAC CAC GCT<br>Tyr Asn Lys Ile Lys Ser Gly Tyr Arg Met Ala Lys Pro Asp His Ala<br>                   910                        915                       920 | 2967 |
| ACC AGT GAA GTC TAC GAG ATC ATG GTG AAA TGC TGG AAC AGT GAG CCG<br>Thr Ser Glu Val Tyr Glu Ile Met Val Lys Cys Trp Asn Ser Glu Pro<br>            925                         930                       935 | 3015 |
| GAG AAG AGA CCC TCC TTT TAC CAC CTG AGT GAG ATT GTG GAG AAT CTG<br>Glu Lys Arg Pro Ser Phe Tyr His Leu Ser Glu Ile Val Glu Asn Leu<br>               940                         945                       950 | 3063 |
| CTG CCT GGA CAA TAT AAA AAG AGT TAT GAA AAA ATT CAC CTG GAC TTC<br>Leu Pro Gly Gln Tyr Lys Lys Ser Tyr Glu Lys Ile His Leu Asp Phe<br>955                            960                         965 | 3111 |

-continued

```
CTG AAG AGT GAC CAT CCT GCT GTG GCA CGC ATG CGT GTG GAC TCA GAC      3159
Leu Lys Ser Asp His Pro Ala Val Ala Arg Met Arg Val Asp Ser Asp
970                 975                 980                 985

AAT GCA TAC ATT GGT GTC ACC TAC AAA AAC GAG GAA GAC AAG CTG AAG      3207
Asn Ala Tyr Ile Gly Val Thr Tyr Lys Asn Glu Glu Asp Lys Leu Lys
                990                 995                 1000

GAC TGG GAG GGT GGT CTG GAT GAG CAG AGA CTG AGC GCT GAC AGT GGC      3255
Asp Trp Glu Gly Gly Leu Asp Glu Gln Arg Leu Ser Ala Asp Ser Gly
            1005                1010                1015

TAC ATC ATT CCT CTG CCT GAC ATT GAC CCT GTC CCT GAG GAG GAG GAC      3303
Tyr Ile Ile Pro Leu Pro Asp Ile Asp Pro Val Pro Glu Glu Glu Asp
        1020                1025                1030

CTG GGC AAG AGG AAC AGA CAC AGC TCG CAG ACC TCT GAA GAG AGT GCC      3351
Leu Gly Lys Arg Asn Arg His Ser Ser Gln Thr Ser Glu Glu Ser Ala
    1035                1040                1045

ATT GAG ACG GGT TCC AGC AGT TCC ACC TTC ATC AAG AGA GAG GAC GAG      3399
Ile Glu Thr Gly Ser Ser Ser Ser Thr Phe Ile Lys Arg Glu Asp Glu
1050                1055                1060                1065

ACC ATT GAA GAC ATC GAC ATG ATG GAC GAC ATC GGC ATA GAC TCT TCA      3447
Thr Ile Glu Asp Ile Asp Met Met Asp Asp Ile Gly Ile Asp Ser Ser
                1070                1075                1080

GAC CTG GTG GAA GAC AGC TTC CTG TAACTGGCGG ATTCGAGGGG TTCCTTCCAC     3501
Asp Leu Val Glu Asp Ser Phe Leu
                1085

TTCTGGGGCC ACCTCTGGAT CCCGTTCAGA AAACCACTTT ATTGCAATGC GGAGGTTGAG   3561

AGGAGGACTT GGTTGATGTT TAAAGAGAAG TTCCCAGCCA AGGGCCTCGG GGAGCGTTCT   3621

AAATATGAAT GAATGGGATA TTTTGAAATG AACTTTGTCA GTGTTGCCTC TTGCAATGCC   3681

TCAGTAGCAT CTCAGTGGTG TGTGAAGTTT GGAGATAGAT GGATAAGGGA ATAATAGGCC   3741

ACAGAAGGTG AACTTTGTGC TTCAAGGACA TTGGTGAGAG TCCAACAGAC ACAATTTATA   3801

CTGCGACAGA ACTTCAGCAT TGTAATTATG TAAATAACTC TAACCAAGGC TGTGTTTAGA   3861

TTGTATTAAC TATCTTCTTT GGACTTCTGA AGAGACCACT CAATCCATCC TGTACTTCCC   3921

TCTTGAAACC TGATGTAGCT GCTGTTGAAC TTTTTAAAGA AGTGCATGAA AAACCATTTT   3981

TGAACCTTAA AAGGTACTGG TACTATAGCA TTTTGCTATC TTTTTTAGTG TTAAAGAGAT   4041

AAAGAATAAT AAG                                                      4054
```

(2) INFORMATION FOR SEQ ID NO:36:

(i) SEQUENCE CHARACTERISTICS:
        (A) LENGTH: 1089 amino acids
        (B) TYPE: amino acid
        (D) TOPOLOGY: linear (ii) MOLECULE TYPE: protein (xi) SEQUENCE DESCRIPTION: SEQ ID NO:36:

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
                20                  25                  30

Asn Glu Asn Glu Lys Val Val Gln Leu Asn Ser Ser Phe Ser Leu Arg
            35                  40                  45

Cys Phe Gly Glu Ser Glu Val Ser Trp Gln Tyr Pro Met Ser Glu Glu
        50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
```

```
                        85                  90                  95
Leu Tyr Thr Cys Tyr Tyr Asn His Thr Gln Thr Glu Glu Asn Glu Leu
                100                 105                 110
Glu Gly Arg His Ile Tyr Ile Tyr Val Pro Asp Pro Asp Val Ala Phe
            115                 120                 125
Val Pro Leu Gly Met Thr Asp Tyr Leu Val Ile Val Glu Asp Asp Asp
        130                 135                 140
Ser Ala Ile Ile Pro Cys Arg Thr Thr Asp Pro Glu Thr Pro Val Thr
145                 150                 155                 160
Leu His Asn Ser Glu Gly Val Val Pro Ala Ser Tyr Asp Ser Arg Gln
                165                 170                 175
Gly Phe Asn Gly Thr Phe Thr Val Gly Pro Tyr Ile Cys Glu Ala Thr
            180                 185                 190
Val Lys Gly Lys Lys Phe Gln Thr Ile Pro Phe Asn Val Tyr Ala Leu
        195                 200                 205
Lys Ala Thr Ser Glu Leu Asp Leu Glu Met Glu Ala Leu Lys Thr Val
210                 215                 220
Tyr Lys Ser Gly Glu Thr Ile Val Thr Cys Ala Val Phe Asn Asn
225                 230                 235                 240
Glu Val Val Asp Leu Gln Trp Thr Tyr Pro Gly Glu Val Lys Gly Lys
                245                 250                 255
Gly Ile Thr Ile Leu Glu Glu Ile Lys Val Pro Ser Ile Lys Leu Val
            260                 265                 270
Tyr Thr Leu Thr Val Pro Glu Ala Thr Val Lys Asp Ser Gly Asp Tyr
        275                 280                 285
Glu Cys Ala Ala Arg Gln Ala Thr Arg Glu Val Lys Glu Met Lys Lys
    290                 295                 300
Val Thr Ile Ser Val His Glu Lys Gly Phe Ile Glu Ile Lys Pro Thr
305                 310                 315                 320
Phe Ser Gln Leu Glu Ala Val Asn Leu His Glu Val Lys His Phe Val
                325                 330                 335
Val Glu Val Arg Ala Tyr Pro Pro Arg Ile Ser Trp Leu Lys Asn
            340                 345                 350
Asn Leu Thr Leu Ile Glu Asn Leu Thr Glu Ile Thr Thr Asp Val Glu
        355                 360                 365
Lys Ile Gln Glu Ile Arg Tyr Arg Ser Lys Leu Lys Leu Ile Arg Ala
    370                 375                 380
Lys Glu Glu Asp Ser Gly His Tyr Thr Ile Val Ala Gln Asn Glu Asp
385                 390                 395                 400
Ala Val Lys Ser Tyr Thr Phe Glu Leu Leu Thr Gln Val Pro Ser Ser
                405                 410                 415
Ile Leu Asp Leu Val Asp Asp His His Gly Ser Thr Gly Gly Gln Thr
            420                 425                 430
Val Arg Cys Thr Ala Glu Gly Thr Pro Leu Pro Asp Ile Glu Trp Met
        435                 440                 445
Ile Cys Lys Asp Ile Lys Lys Cys Asn Asn Glu Thr Ser Trp Thr Ile
    450                 455                 460
Leu Ala Asn Asn Val Ser Asn Ile Ile Thr Glu Ile His Ser Arg Asp
465                 470                 475                 480
Arg Ser Thr Val Glu Gly Arg Val Thr Phe Ala Lys Val Glu Glu Thr
                485                 490                 495
Ile Ala Val Arg Cys Leu Ala Lys Asn Leu Leu Gly Ala Glu Asn Arg
            500                 505                 510
```

```
Glu Leu Lys Leu Val Ala Pro Thr Leu Arg Ser Glu Leu Thr Val Ala
        515                 520                 525

Ala Ala Val Leu Val Leu Val Ile Val Ile Ile Ser Leu Ile Val
    530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
                580                 585                 590

Leu Val Leu Gly Arg Val Leu Gly Ser Gly Ala Phe Gly Lys Val Val
                595                 600                 605

Glu Gly Thr Ala Tyr Gly Leu Ser Arg Ser Gln Pro Val Met Lys Val
        610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
                660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
        690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
                740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
        770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
                820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
        850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
                900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
        930                 935                 940
```

```
His Leu Ser Glu Ile Val Glu Asn Leu Leu Pro Gly Gln Tyr Lys Lys
945             950             955             960

Ser Tyr Glu Lys Ile His Leu Asp Phe Leu Lys Ser Asp His Pro Ala
            965             970             975

Val Ala Arg Met Arg Val Asp Ser Asp Asn Ala Tyr Ile Gly Val Thr
            980             985             990

Tyr Lys Asn Glu Glu Asp Lys Leu Lys Asp Trp Glu Gly Gly Leu Asp
        995             1000            1005

Glu Gln Arg Leu Ser Ala Asp Ser Gly Tyr Ile Ile Pro Leu Pro Asp
        1010            1015            1020

Ile Asp Pro Val Pro Glu Glu Glu Asp Leu Gly Lys Arg Asn Arg His
1025            1030            1035            1040

Ser Ser Gln Thr Ser Glu Glu Ser Ala Ile Glu Thr Gly Ser Ser Ser
                1045            1050            1055

Ser Thr Phe Ile Lys Arg Glu Asp Glu Thr Ile Glu Asp Ile Asp Met
                1060            1065            1070

Met Asp Asp Ile Gly Ile Asp Ser Ser Asp Leu Val Glu Asp Ser Phe
            1075            1080            1085

Leu
```